(12) United States Patent
Tomblin et al.

(10) Patent No.: US 10,285,844 B2
(45) Date of Patent: May 14, 2019

(54) RAPID SETTING COMPOSITE ARTICLE

(71) Applicants: Wichita State University, Wichita, KS (US); Commercial Chemistries, LLC, Cottonwood Heights, UT (US)

(72) Inventors: John S. Tomblin, Wichita, KS (US); Thomas Aldag, Wichita, KS (US); William T. McCarvill, Cottonwood Heights, UT (US); Kimberly M. Reuter, Wichita, KS (US); Joel D. White, Wichita, KS (US); Andrea C. Meyer, Bel Aire, KS (US)

(73) Assignees: Wichita State University, Wichita, KS (US); Commercial Chemistries, LLC, Cottonwood Heights, UT (US)

( * ) Notice: Subject to any disclaimer, the term of this patent is extended or adjusted under 35 U.S.C. 154(b) by 298 days.

(21) Appl. No.: 15/027,984

(22) PCT Filed: Oct. 6, 2014

(86) PCT No.: PCT/US2014/059294
§ 371 (c)(1),
(2) Date: Apr. 7, 2016

(87) PCT Pub. No.: WO2015/054128
PCT Pub. Date: Apr. 16, 2015

(65) Prior Publication Data
US 2016/0270945 A1     Sep. 22, 2016

Related U.S. Application Data

(60) Provisional application No. 62/021,501, filed on Jul. 7, 2014, provisional application No. 61/887,604, filed on Oct. 7, 2013.

(51) Int. Cl.
*A61F 13/04* (2006.01)
*A61F 5/058* (2006.01)
(Continued)

(52) U.S. Cl.
CPC ............ *A61F 5/05825* (2013.01); *A61F 5/01* (2013.01); *A61F 5/0585* (2013.01);
(Continued)

(58) Field of Classification Search
CPC .... A61F 5/05825; A61F 5/01; A61F 5/05841; A61F 5/0585; A61F 13/04; A61L 15/08; A61L 15/12; A61L 15/125; A61L 15/14
See application file for complete search history.

(56) References Cited

U.S. PATENT DOCUMENTS 3,613,675 A    10/1971  Larsen et al.
3,874,376 A     4/1975  Dart et al.
(Continued)

FOREIGN PATENT DOCUMENTS

EP    0639361 A1    2/1995
WO    94/23679 A1   10/1994

OTHER PUBLICATIONS

International Search Report and Written Opinion issued in Corresponding PCT/US2014/059294 dated Jan. 28, 2015 (15 pages).
(Continued)

*Primary Examiner* — Ophelia A Hawthorne
(74) *Attorney, Agent, or Firm* — Hovey Williams LLP

(57) ABSTRACT

A fiber-reinforced composite article useful in supporting or immobilizing an injured body part is disclosed. The composite is a multi-layer, flexible precursor including fiber reinforcement plies, which can be rapidly cured into a rigid body using a thermosetting resin. Methods of making and using the same are also disclosed, along with kits containing such composite articles.

12 Claims, 33 Drawing Sheets

(51) Int. Cl.
*A61L 15/12* (2006.01)
*A61F 5/01* (2006.01)
*A61L 15/14* (2006.01)
*A61L 15/08* (2006.01)

(52) U.S. Cl.
CPC .......... *A61F 5/05841* (2013.01); *A61F 13/04* (2013.01); *A61L 15/08* (2013.01); *A61L 15/12* (2013.01); *A61L 15/125* (2013.01); *A61L 15/14* (2013.01)

(56) References Cited

U.S. PATENT DOCUMENTS

| | | | |
|---|---|---|---|
| 3,881,473 A | | 5/1975 | Corvi et al. |
| 3,985,128 A | | 10/1976 | Garwood et al. |
| 4,341,302 A | * | 7/1982 | Baker .................. B65D 75/326 206/219 |
| 4,512,340 A | | 4/1985 | Buck |
| 4,676,233 A | | 6/1987 | Scheinberg |
| 5,171,208 A | * | 12/1992 | Edenbaum .............. A61F 13/04 602/58 |
| 5,354,821 A | | 10/1994 | Huver et al. |
| 5,496,295 A | | 3/1996 | Wilfong et al. |
| 5,766,724 A | * | 6/1998 | Tailor ........................ A61F 5/01 156/213 |
| 6,490,730 B1 | | 12/2002 | Lyden |
| 6,552,140 B1 | | 4/2003 | Kneafsey et al. |
| 6,613,006 B1 | * | 9/2003 | Asherman .............. A61F 13/04 602/20 |
| 6,681,403 B2 | | 1/2004 | Lyden |
| 7,003,803 B1 | | 2/2006 | Lyden |
| 7,314,457 B2 | | 1/2008 | Reaux |
| 8,030,227 B2 | | 10/2011 | Nakasugi et al. |
| 8,343,082 B2 | | 1/2013 | Evans et al. |
| 2006/0051402 A1 | | 3/2006 | Bogardus et al. |
| 2007/0004993 A1 | | 1/2007 | Coppens et al. |
| 2008/0262400 A1 | | 10/2008 | Clark et al. |
| 2008/0319362 A1 | | 12/2008 | Joseph |
| 2011/0224590 A1 | * | 9/2011 | Jensen ..................... A61F 5/01 602/8 |
| 2012/0073584 A1 | | 3/2012 | Parssinen |

OTHER PUBLICATIONS

3M Material Safety Data Sheet 3M(TM) Scotch-Weld(TM) Plastics & Rubber Instant Adhesive PR5 (formerlly sold as Rite-Lok™ Engineering Grade Instant Adhesive PR5-28 & PR5-454) May 6, 2011 (8 pages).

3M Scotch-Weld Surface Insensitive Instant Adhesives SI5—SI40—SI100—SI1500—SI Gel, Technical Data, Mar. 2010 (4 pages).

Resinlab L.L.C. Material Safety Data Sheet Resinlab Cynergy CA6200 Series Products May 6, 2011 (3 pages).

Permabond Engineering Adhesives, MSDS Material Safety Data Sheet Permabond 101, Jan. 1, 2004 (5 pages).

Permabond Engineering Adhesives, MSDS Material Safety Data Sheet Permabond 910 FS, Jan. 1, 2004 (5 pages).

Fitch, Michael T., et al., Basic Splinting Techniques, The New England Journal of Medicine 359;26, Dec. 25, 2008 (5 pages).

\* cited by examiner

Exothermic Responses

RAPID SETTING COMPOSITE ARTICLE

CROSS-REFERENCE TO RELATED APPLICATIONS

The present application is the National Stage of International Patent Application No. PCT/US2014/059294, filed Oct. 6, 2014, which claims the priority benefit of U.S. Provisional Patent Application Ser. No. 61/887,604, filed Oct. 7, 2013, entitled RAPID SETTING COMPOSITE ARTICLE, and U.S. Provisional Patent Application Ser. No. 62/021,501, filed Jul. 7, 2014, entitled RAPID SETTING COMPOSITE ARTICLE, each of which is incorporated by reference in its entirety herein.

FEDERALLY SPONSORED RESEARCH OR DEVELOPMENT

This invention was made with government support under #W81XWH-11-1-0688, awarded by the United States Army Medical Research and Materiel Command. The United States government has certain rights in the invention.

BACKGROUND OF THE INVENTION

Field of the Invention

The present invention relates to rapid-setting composite articles useful in a variety of fields, including the use in supporting and immobilizing injured limbs or other body parts.

Description of Related Art

Various devices for supporting or immobilizing injuries are known. However, they suffer from many drawbacks. For example, splinting devices currently used by military medics provide less than ideal fracture stabilization, which causes increased soft tissue damage during field extraction. Battlefield injuries present a complexity of medical problems in a hostile environment, often at considerable distance from trauma care. Orthopedic injuries constitute a majority of the combat casualties in recent U.S. military conflicts. Extremity injuries account for 71% of combat casualties, and of these injuries, 19% are fractures. Military medics frequently use the SAM splint or wire mesh splint for fracture stabilization, and these products provide less than ideal fracture stabilization. An improved device is needed to provide better stabilization while maintaining low weight, compact size, and ease of use.

SUMMARY OF THE INVENTION

The present invention is broadly concerned with a fiber-reinforced composite article useful in supporting or immobilizing an injured body part. The article comprises a multi-layer body having opposing first and second major surfaces. The multi-layer body generally comprises a fiber reinforcement layer, an encapsulating film adjacent the fiber reinforcement layer, and an insulating barrier adjacent the encapsulating film. The fiber reinforcement layer is impregnated with a thermosetting resin that can be rapidly cured to yield a rigid body suitable for immobilizing and supporting the injured body part. A resin distribution system can be included to achieve rapid delivery and distribution of the resin throughout the fiber reinforcement. In one or more embodiments, the multi-layer body comprises at least one ply of fiber reinforcement (e.g., first and second fiber reinforcement layers), two plies of encapsulating film (e.g., first and second encapsulating films), and one or two plies of insulating barrier (e.g., first and second insulating barriers). A first layer of encapsulating film is adjacent the first fiber reinforcement ply and a second layer of encapsulating film is adjacent the second fiber reinforcement ply, such that the fiber reinforcement plies are "sandwiched" between the two encapsulating films. When present, the distribution system can be between the first and second fiber reinforcement layers or another position. The fiber reinforcement plies can also be pre-impregnated with the resin to form a prepreg compartment encased by the encapsulating film. The insulating barrier can be first and second exterior layers that correspond to the outermost layers of the multi-layer body. In other words, the outermost layers of the multi-layer body correspond to the first and second insulating barriers respectively, which are positioned adjacent the encapsulating films or other layers in the stack.

A method of rapidly supporting or immobilizing an injured body part is also provided. The method comprises providing a flexible, multi-layer body (composite precursor) having opposing first and second major surfaces as described above. The flexible, multi-layer body is arranged around or next to and in conformance with the injured body part with the insulating barrier adjacent to the body part. A thermosetting resin is introduced into the multi-layer body, which impregnates the fiber reinforcement layer(s). Advantageously, the resin cures in less than about 10 minutes after being introduced into the article, to yield a rigid lamellar body, thereby supporting or immobilizing the injured body part. Slower cure times may be useful in other applications.

A further method of rapidly supporting or immobilizing an injured body part is also described herein. The method comprises providing a flexible, multi-layer body (composite precursor) having opposing first and second major surfaces as described above, except that the fiber reinforcement layer(s) is pre-impregnated with a thermosetting resin. The prepreg body is arranged around or next to and in conformance with the injured body part with the insulating barrier adjacent to the body part. The thermosetting resin is exposed to a catalyst (either actively or passively), and thereafter cures in less than about 10 minutes, to yield a rigid lamellar body, thereby supporting or immobilizing the injured body part.

Also described herein is a further method of rapidly supporting or immobilizing an injured body part. The method comprises providing a flexible, multi-layer body (composite precursor) having opposing first and second major surfaces as described above, except that the fiber reinforcement layer(s) is pre-impregnated with a photo-curable resin. The resin is exposed to a light, and thereafter cures in less than about 10 minutes, to yield a rigid lamellar body, thereby supporting or immobilizing the injured body part. In some embodiments, a source of light can be integrally formed as part of a layer in the multi-layer body, A kit for rapidly supporting or immobilizing an injured body part is also described herein. The kit comprises a composite precursor comprising a flexible, multi-layer body having opposing first and second major surfaces as described herein, a thermosetting resin; and instructions for use thereof. The thermosetting resin can be provided in a separate container, or the precursor can be a prepreg with the resin pre-impregnated into the fiber reinforcement.

DETAILED DESCRIPTION

The present invention is concerned with a moldable, fiber-reinforced composite article comprising a thermosetting resin or polymer matrix distributed throughout a fiber reinforcement. Additional components that can optionally be included in the composite article include a resin distribution system, an encapsulating film, and/or an insulating barrier. The composite is initially provided as a precursor that can be molded or formed into (and around) a variety of shapes and then rapidly cured into a rigid composite form. The "precursor" composite refers to the article before curing of the resin. Thus, the precursor is moldable, flexible, bendable, rollable, and/or foldable before being cured into the rigid composite article, which is non-moldable, non-flexible, non-bendable, non-rollable, and/or non-foldable. Advantageously, the composite article can be cured without the need for water, heat, or stirring of ingredients.

In one or more embodiments, the composite article is useful for temporary or semi-permanent immobilization and/or support of injured body parts. For example, the composite article is useful as a temporary or semi-permanent splinting member, cast, brace, and the like, for supporting and/or immobilizing broken, fractured, or otherwise damaged/injured body parts. The term "body parts" includes any part of the body that may need to be supported and/or immobilized, including without limitation, limbs, fingers, toes, neck, back, torso, and the like, including any portions thereof (e.g., specific joints, such as knees, elbows, wrists, ankles, etc.), as well as combinations thereof (e.g., neck and back, head-to-toe/whole body, etc.).

Figure 1:
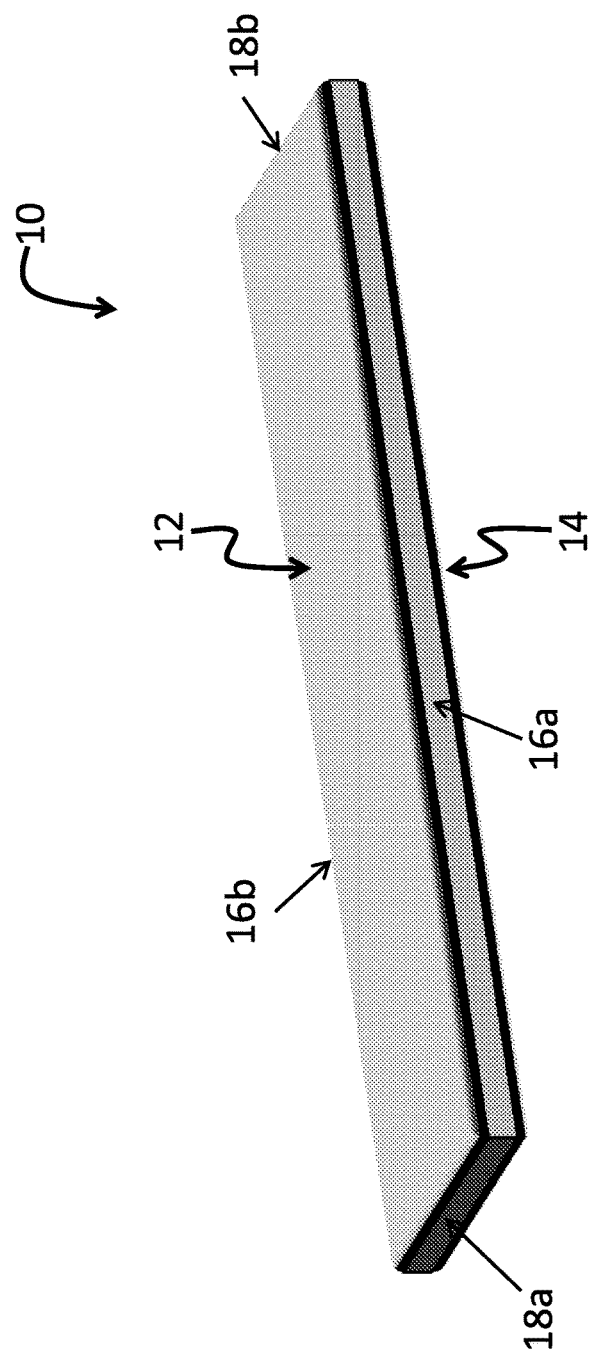
FIG. 1 is a perspective view (line drawing) of a multi-layer sheet in accordance with one aspect of the invention.
Figure 2:
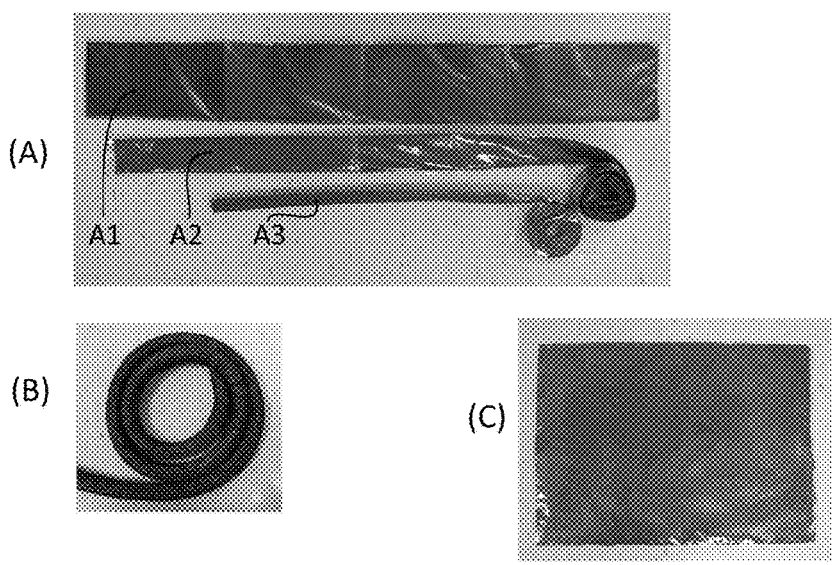
FIG. 2 illustrates a summary of various formats the composite article could be used as (A) Tape widths; (B) Rope; (C) Sheet; and (D) estimated dimensions and weight, not including resin or insulating barrier.
Figure 3:
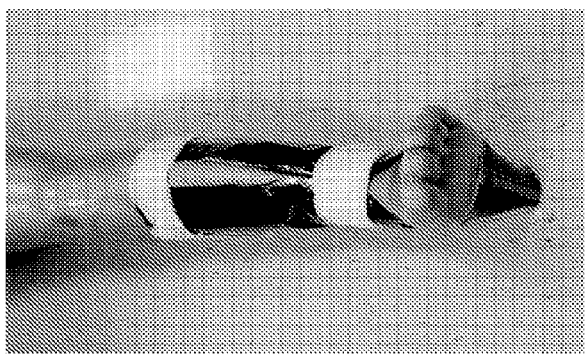
FIG. 3 shows photographs of the composite article used as a wide tape for splinting a leg or ankle injury.
Figure 3:
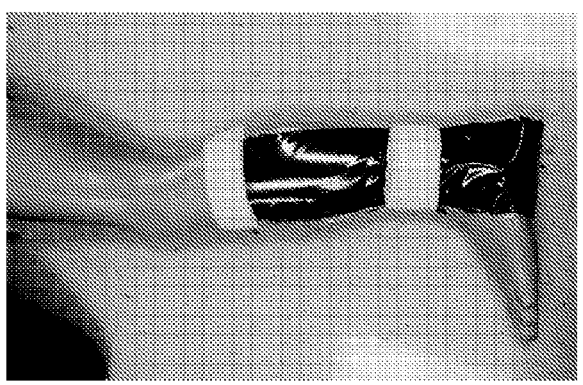
Figure 3:
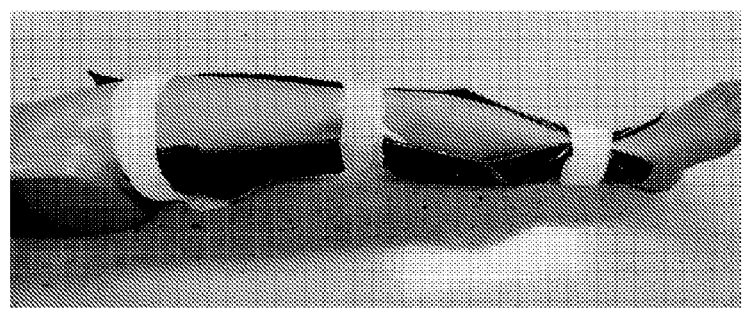
Figure 3:
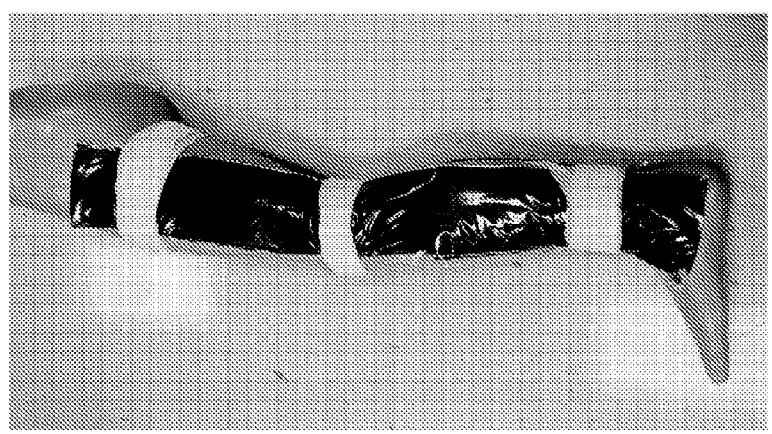
Figure 4:
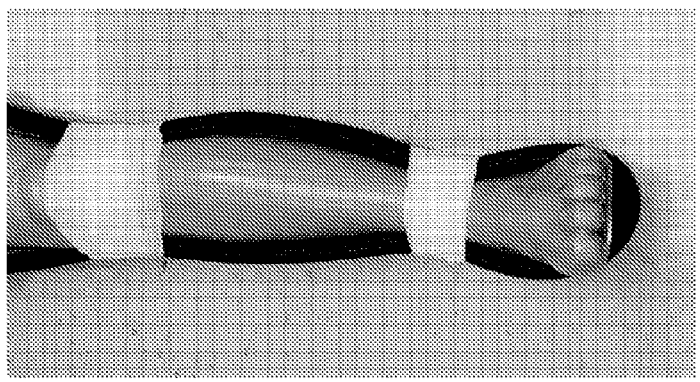
FIG. 4 shows photographs of the composite article used as a rope for splinting a leg with and without tape for securing the article to the leg.
Figure 4:
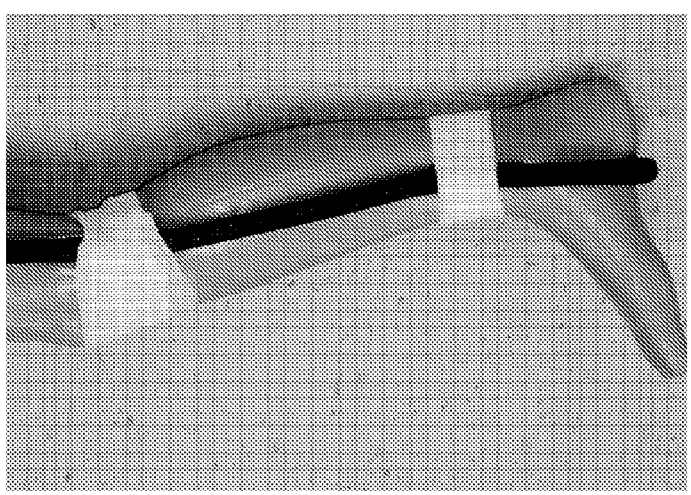
Figure 4:
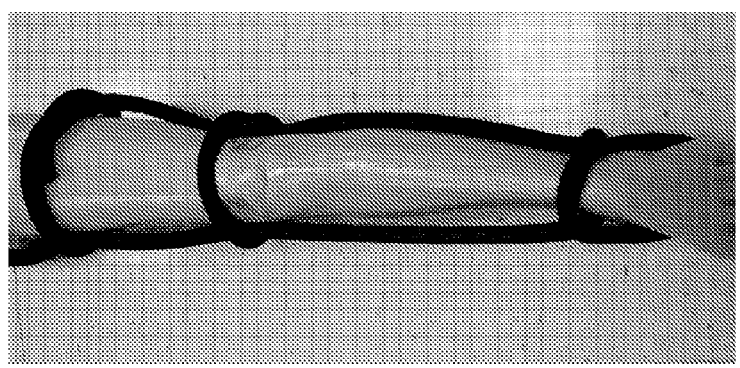
Figure 4:
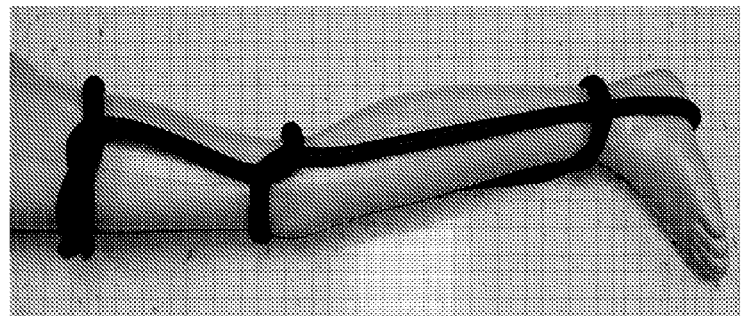
Figure 5:
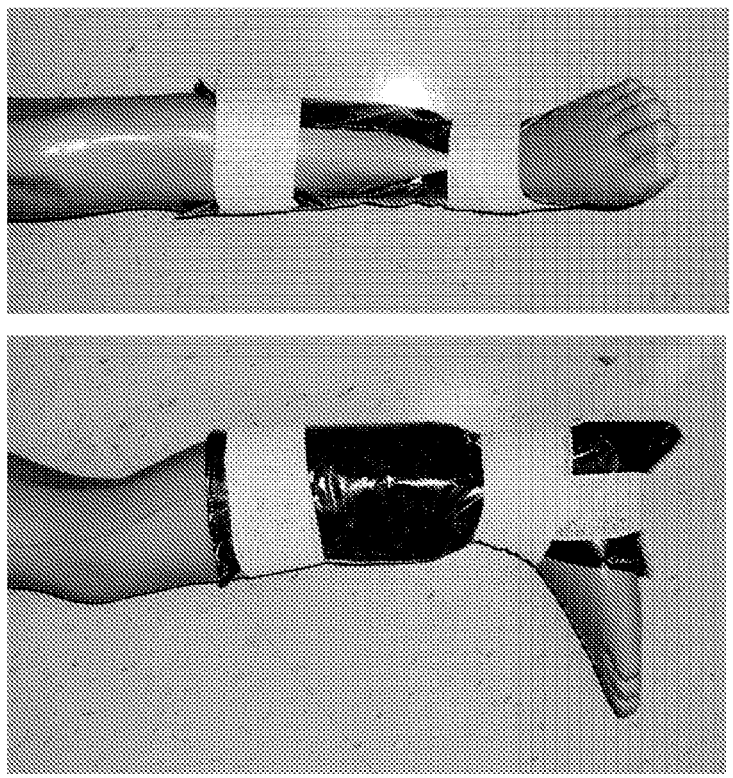
FIG. 5 shows photographs of the composite article used as a sheet for splinting a leg or ankle injury.
Figure 5:
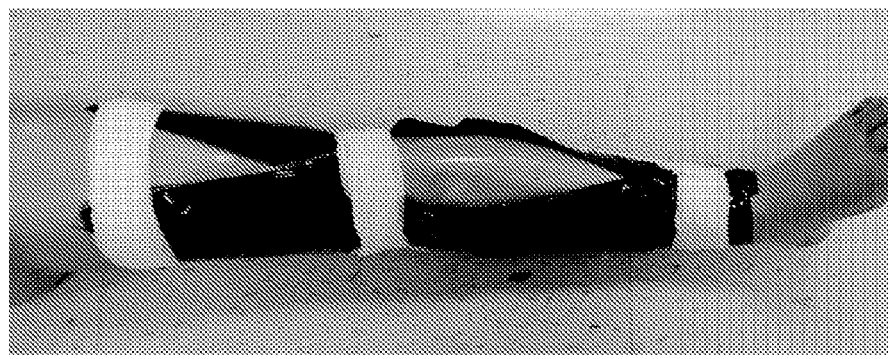
Figure 5:

Referring to FIG. 1, in one or more embodiments, the composite article is a multi-layer or multi-ply body 10. In FIG. 2, the body 10 can be in the form of a sheet, strip, ribbon, or tape, where the term "sheet" will be used hereinafter to refer both to sheets as well as elongated strips, ribbons, and/or tapes of differing widths (A1, A2, A3). Referring back to FIG. 1, the body 10 in the form of a sheet comprises opposing first and second major surfaces 12, 14, referred to herein as a front (or upper) surface 12 and a back (or lower) surface 14, respectively. The sheet 10 also has a pair of laterally-spaced longitudinal side edges 16a, 16b, and a pair of laterally spaced transverse ends 18a, 18b. The body 10 could also be in the form of an elongated rope. Various photographs of the body 10 in different configurations are shown in FIGS. 2-5.

Figure 6A:
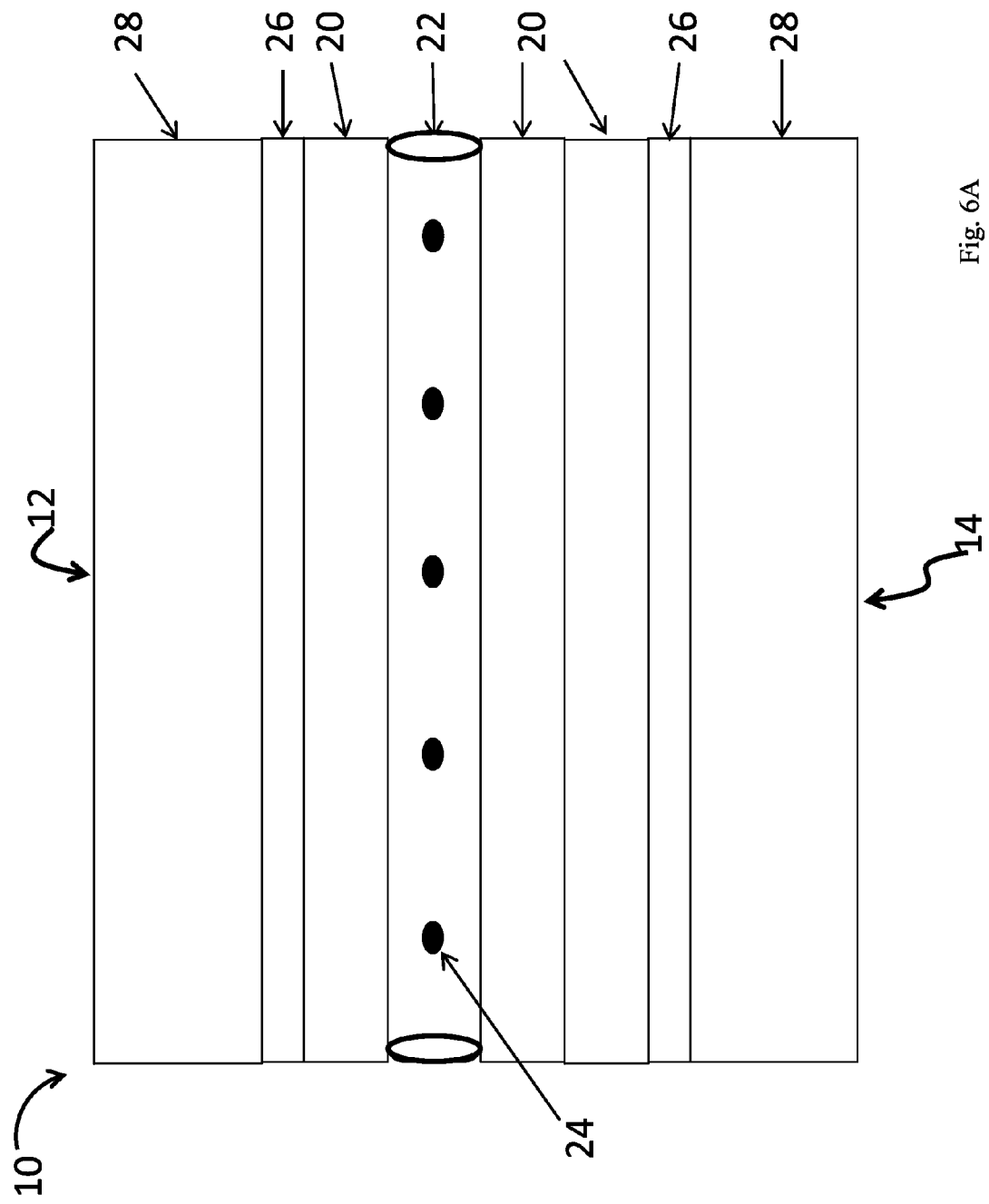
FIG. 6A is a longitudinal cross-section of a multi-layer sheet embodiment.

FIG. 6A shows a longitudinal cross-section of a sheet in accordance with one aspect of the invention to facilitate viewing of the layers, as well as the resin distribution system and holes, discussed below. As noted above, the composite article comprises a fiber reinforcement impregnated with a thermosetting polymer matrix. As depicted in FIG. 6A, the article 10 preferably comprises one or more layers or plies of fiber reinforcement 20, more preferably from about 2 to about 10, and even more preferably from about 2 to about 4 plies. It will be appreciated that the plies can each be made of the same type of fiber reinforcement. Alternatively, each ply can be individually selected, such that different types of fiber reinforcement could be used for each layer. The fiber reinforcement can comprise any suitable fibrous material or fabric, and may be selected from the group consisting of wovens, nonwovens, and combinations thereof. The fiber reinforcement may comprise continuous or discontinuous fibers, filaments or threads. Various types of fiber reinforcements are known in the art, with preferred reinforcement materials including fiberglass, carbon fiber, polyaramid, or natural fiber, as unidirectional, wovens, or nonwovens. The fiber reinforcement can include reactive fiber finishes or sizings commonly found on commercially-available fibers, such as those compatible with epoxies, amines, and the like. In some embodiments, it may be desirable to de-size or de-finish the fiber before its use in the invention, for example, by heat cleaning. That is, it has been found that un-sized/de-sized and/or unfinished/de-finished fiber reinforcements are particularly preferred for some embodiments of the invention.

A wide variety of fiber reinforcements are suitable for use in the invention depending upon the final desired characteristics. Fiber reinforcements are generally characterized according to their fill count, warp count, warp %, weave or tow, weight, fiber diameter, and thickness. The fill refers to the number of fibers running the width of the roll or bolt and perpendicular to the warp. The fill count for suitable fiber reinforcements will generally range from about 6 to about 450, and preferably from about 10 to about 150. It is noted that different types of yarns can be used for either the fill or the warp depending upon the material. The warp refers to the number of fibers running the length of the roll or bolt and perpendicular to the fill. The warp count for suitable fiber reinforcements will generally range from about 6 to about 450, and preferably from about 10 to about 150. The warp % refers to the percentage of the total number of fibers running in the warp direction. The warp % will preferably be greater than about 70%, preferably greater than about 85% and more preferably greater than about 90%.

The "weave" refers to the configuration of the individual threads or fibers. For example, a "plain" weave means the warp and fill threads cross alternately. This is the most common weave. "4 Harness" (4 HS Satin or crowfoot) weave means the fill thread floats over three warp threads, then under one warp thread. This weave is more pliable than the plain weave, therefore conforms to complex curves more easily. "8 Harness" (8 HS Satin) weave means the fill thread floats over seven warp threads, then under one warp thread. This weave is the most pliable of the standard fiberglass weaves. "2×2 Twill" weave means the fill thread floats over two warp threads, then under two warp threads. This weave is found most commonly in carbon fabrics and is more pliable than plain weave. A variety of other weave types are also known and available, including the mock leno, which is a more open weave having a lattice-like look made to resemble a leno weave, but without that weave's pairs of warp yarns. Mock leno can be beneficial in some applications because its open structure makes it easier to wet out. Unifabrics such as unidirectional carbon fabrics can also be used instead of weaves. The "tow" refers to the bundle of individual carbon filaments used to weave carbon fabric. A 50 k tow means that from about 48,000-50,000 carbon filaments in the tow. Smaller tow (i.e., 12 k, 24 k, etc.) are manufactured to the desired tow count. It will be appreciated that certain characteristics of the selected fiber reinforcement will affect or can be compensated by other components of the composite article. For example, fiber reinforcements having more fibers running longitudinally (warp) will increase the strength of the composite article. However, a lack of warp fibers can be compensated for by using more resin in the composite article. Thus, it will be appreciated that the various components of the composite article can be selected in relation to the characteristics of the other components used to achieve the most appropriate balance of desired properties, such as flexibility, light weight, and low volume in the precursor, with suitable stiffness and strength in the cured composite.

The weight of the fiber reinforcement is estimated in ounces per square yard, and will preferably range from about 4 to about 18 ounces per square yard. The fiber diameter is typically measured in microns, and will preferably range from about 4 to about 13, and more preferably from about 5 to about 9. The thickness of the fiber reinforcement is typically measured in fractions of an inch. It will be appreciated that in addition to the number of plies, the thickness of the fiber reinforcement will determine the amount of resin required to fill the fabric or weave. The thickness will preferably range from about 0.003" to about 0.05", and preferably from about 0.01" to about 0.03". In one or more embodiments, the fiber reinforcement is preferably pretreated with an accelerant to adjust or control the curing time for the thermosetting resin discussed below. In one or more embodiments, the accelerant is first dissolved in a suitable solvent with a low boiling point (for fast evaporation) such as acetone or naphtha before being applied to the fiber reinforcement, and preferably coating the individual fibers. The accelerant can also be applied to other surfaces such as the inner side of the encapsulating films. It will be appreciated that the type of accelerant used will depend largely upon the particular resin used. Non-limiting examples of suitable accelerants include water, diethylol-p-toluidine, N,N-dimethyl-p-toluidine, oxyalkylenated polyamines (e.g., tetrahydroxypropylethylendiamine, or a mixture of dipropylenetriamine, polyamine with epichlorohydrine and laurylamine, ethoxylated), and the like. The accelerant will preferably have a shelf life of at least about 6 months, and even more preferably at least about 24 months. The "shelf life" refers to the ability of the accelerant to retain a sufficient level of reactivity/activity after application to the fiber reinforcement. In other words, the accelerant must maintain a sufficient ability to induce or catalyze curing of the thermoset resin even when stored over a period of time.

Figure 6B:
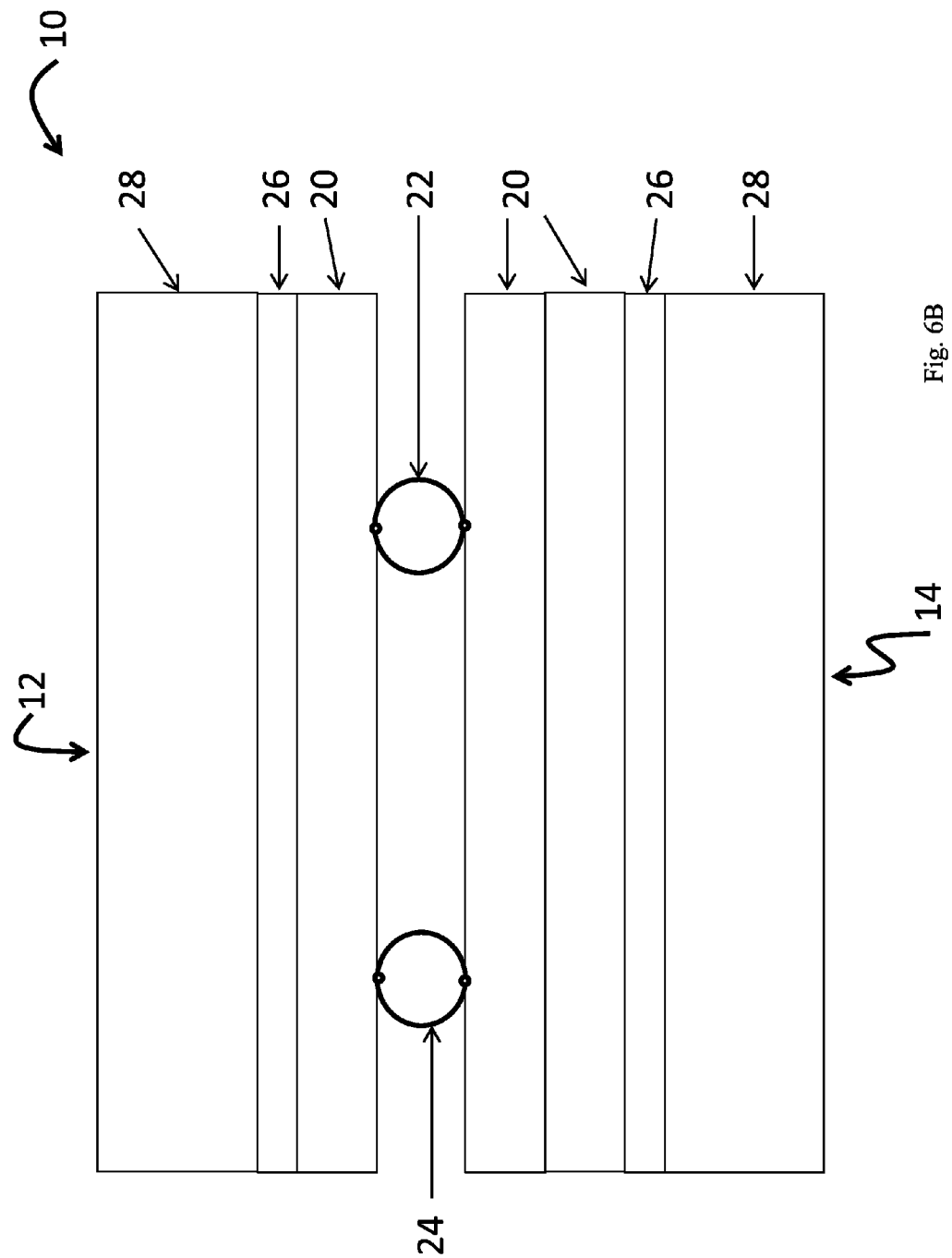
FIG. 6B is a transverse cross-section of a multi-layer sheet embodiment.
Figure 9:
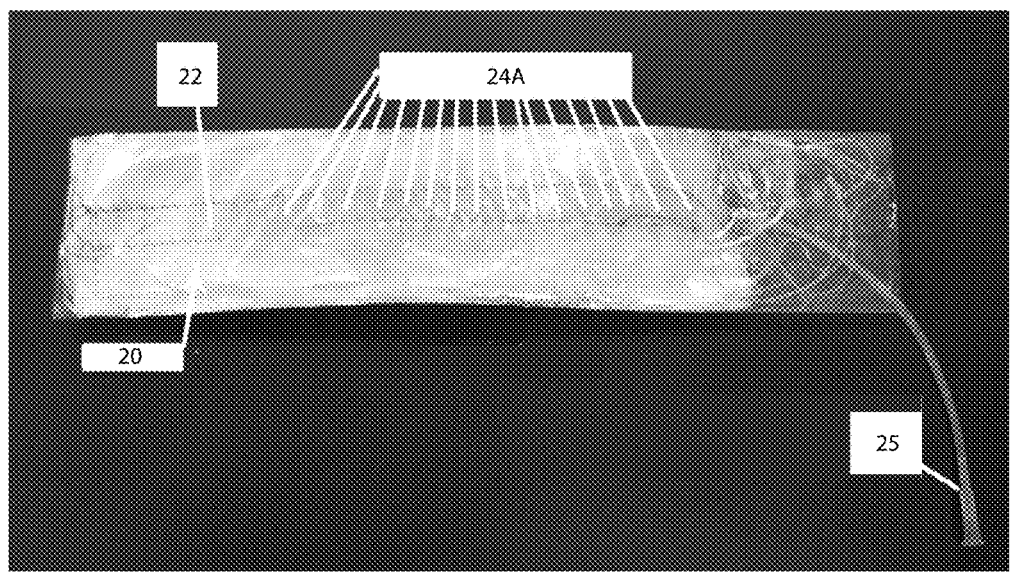
FIG. 9 is a close-up photograph of a resin distribution tube in accordance with an embodiment tested in Example 1.

In one or more embodiments, the composite article further comprises a resin distribution system. Various resin distribution concepts are discussed in the working examples herein. Any suitable system for delivering and distributing the resin throughout the fiber reinforcement plies could be used in the invention. In one or more embodiments, the resin distribution system comprises a tube 22 for delivering the thermosetting resin into the fiber reinforcement plies 20. In one or more embodiments, the resin distribution tube presents a generally elongated hollow body having a peripheral wall defining a substantially enclosed interior cavity. As depicted in the Figures, the resin distribution tube 22 presents a radial peripheral wall and a substantially radially enclosed cavity operable to receive (i.e., to be filled with) and to retain the resin. Thus, as shown in FIG. 6B, the radial peripheral wall presents a substantially circular axial cross section. It is noted, however, that alternate shapes (e.g., polygonal cross sections) are possible without departing from the teachings of the present invention. Thus, it will be readily apparent to one of ordinary skill in the art that the term "radial," as used herein with respect to the peripheral wall, is not limited to substantially circular cross sections and encompasses polygonal cross sections or cross sections presenting other geometric shapes (e.g., oval or elliptical cross sections). Thus, the shape of the tube is not as important as meeting the other parameters discussed below. In any event, the resin distribution tube 22 comprises a plurality of distribution holes 24 extending through the radial peripheral wall, and through which the resin will exit the distribution tube 22 and enter the fiber reinforcement plies 20. The distribution holes 24 will generally be spaced out along the length of the tube body to facilitate even distribution of the resin throughout the fiber reinforcement. In one or more embodiments, the distribution tube 22 extends substantially the full length of the composite body 10. A variety of materials are suitable for use as the resin distribution tube. The material should be flexible, pliable, and bendable without kinking or collapsing, which would obstruct the flow of resin; and therefore, must still have a certain degree of self-sustaining rigidity and not deform merely due to its own internal forces. The material must also be compatible with the thermosetting resin selected for use, meaning that it will not unfavorably react with or be degraded by the thermosetting resin. In one or more embodiments, the resin distribution tube will also be radiolucent. Exemplary materials include polyurethane, polyethylene, polypropylene, polyamide, silicone rubber, fluorinated ethylene propylene, polytetrafluoroethylene, ethylene-propylene-diene monomer rubber, polyethylene/vinyl acetate, and the like. The size of the tubing can vary depending upon the final intended use of the composite, but will generally have a maximum cross-section dimension of from about 0.01 to about 0.20 inches, and preferably from about 0.04 to about 0.10 inches. The maximum cross-section dimension refers to the largest dimension of a cross-section of the interior cavity of the tube. For example, in the case of generally radial tubing, the maximum cross-section dimension would be the interior diameter of the tubing. In one or more embodiments, illustrated by FIG. 9, the resin distribution tube 22 will also comprise a port 25 for introducing the thermosetting resin into the tube (not shown). It will be appreciated that any number of ports, fittings, or connectors can be used to facilitate introduction of the thermosetting resin into the tube. Examples include luer lock adapters, barbed fittings, push-to-connect fittings, quick disconnect fittings, quick turn fittings, rupture-able membranes, puncture-able membranes, and the like.

In general, the resin distribution system will be situated between two fiber reinforcement plies 20. In one or more embodiments, the composite article further comprises a tackifier to adhere the fiber reinforcement plies together (not shown). Not only does this facilitate holding the resin distribution system in place, but has also been found to facilitate wicking and distribution of the resin when injected by preventing gapping and maintaining contact between the plies and with the resin distribution system. Any suitable tackifier could be used, with spray adhesives and hot melt web adhesives being particularly preferred. In one or more embodiments, the resin distribution system 22 is in the form of a resin distribution tube 22. Depending on the size of the composite article, it may be desirable to have more than one resin distribution tube 22 running along the length of the multi-layer body 10. This is depicted in the transverse cross-section image in FIG. 6B, where the tube(s) are situated equidistant from the midline and perimeter of the composite body. The distribution tubes 22 could be separate tubes with separate, individual ports, or they can be presented as a continuous loop having a shared port for introducing the resin into the tube(s). For example, a Y-connector could be used to secure first and second ends of the same tube creating a loop formation, as described in the working Examples below. The Y-connector would then be connected to the appropriate port for introducing the resin into the looped tube. At the appropriate time, the resin is then injected via the port into the distribution tube 22, where it fills the tube and exits out the distribution holes 24 into the adjacent plies of fiber reinforcement. Illustrated in FIGS. 7 and 9, it will be appreciated that the distribution holes 24 do not necessarily need to be circular holes, but could be any type of suitable opening in the sidewall of the tube 25 through which resin 30 can exit the tube such as slits, cuts, porous tube walls, and the like (24A-24F). It will also be appreciated that other techniques could be used in lieu of or in addition to the resin distribution tube to facilitate distribution and manipulate the resin throughout the fiber reinforcement. Examples of such alternative resin distribution systems include manual distribution by hand or with a tool such as a squeegee, use of resin distribution systems that could be made with heat sealed channels in the encapsulating layers, tubing channels, or with perforated holes or slits cut into a surface barrier. Other alternatives include the use of a vacuum system to aid in resin distribution, storing the resin in small breakable capsules which are located adjacent to the fiber, separating the resin and fabric with a semi-permeable membrane which the resin can be forced across to impregnate the fabric, and the like.

In one or more embodiments, the composite article 10 further comprises an encapsulating film 26 operable to constrain and contain the resin within the layers of fiber reinforcement 20 during and/or after injection. It also provides some back pressure to force and distribute the resin into the entire volume and surface area of the fiber reinforcement. Thus, the encapsulating film 26 will be present as one or more layers adjacent the fiber reinforcement plies 20. The encapsulating film 26 also helps isolate the fiber reinforcement (and resin) from the environment, protecting it from moisture, dirt, heat, light, and loss of resin before and during resin distribution and cure, and the like. In one or more embodiments, the encapsulating film 26 is immediately adjacent its respective fiber reinforcement ply 20. In one or more embodiments, an intermediate layer of phase change material could be present between the encapsulating film 26 and fiber reinforcement ply (not shown). In one or more embodiments, the encapsulating film is also operable to contain the odor produced during curing of the thermosetting resin. As noted above, each "layer" of the encapsulating film can itself be multi-layer or multi-ply. Various materials can be used for the encapsulating film so long as they meet the characteristics described herein, and do not inhibit the flexibility and/or mold-ability of the precursor article. Semi-permeable and impermeable films which are particularly useful include plastic films (e.g., nylon, polyethylene, polypropylene, polyester), metal foils (e.g., aluminum, aluminized polymer films), and multi-layer or multi-ply combinations thereof. The thickness of the encapsulating film will preferably range from about 0.0005 to about 0.01 inches, and more preferably from about 0.001 to about 0.005 inches. In one or more embodiments, as depicted in FIG. 6B, the composite article comprises a first (upper) encapsulating film 26 adjacent a first (upper) fiber reinforcement ply 20, and a second (lower) encapsulating film 26 adjacent a second (lower) reinforcement ply 20 and opposite of the first encapsulating film 26, with the first and second fiber reinforcement plies 20 being situation in-between the first and second encapsulating films 26. Accordingly, the outer perimeter or edges of the first and second encapsulating films 26 can be sealed together, thereby sealing the first and second fiber reinforcement plies (and phase change layer(s), if present) therebetween.

In one or more embodiments, the composite article 10 further comprises an insulating barrier 28. In one or more embodiments, the composite article 10 comprises a first (upper) layer of insulating barrier 28 adjacent the upper encapsulating film 26 and a second (lower) layer of insulating barrier 28 adjacent the lower encapsulating film 26. Thus, the insulating barrier 28 can also be thought of as the outermost layer of the composite article 10, with the external surface of the barrier 28 corresponding to the front surface 12 and back surface 14 of the article, respectively. The insulating barrier 28 is operable to shield and isolate the exothermic reaction during curing of the resin, but also provide padding and cushioning bony prominences or pressure points, and increasing comfort for skin contact. Thus, suitable materials will not only be able to prevent the transmission of heat, but also cushion the injured limb or body part from the rigid composite once cured. Thus, open- or closed-cell foams, rubbers, ceramics, fabrics, the like, and combinations thereof are suitable for use in the invention as flexible and lightweight insulating barriers 28. Particularly preferred materials include closed-cell polyethylene foam, flexible polyurethane foam, flexible polyvinyl chloride foam, polyethylenevinylacetate foam, silicone foam, neoprene foam, expanded polyethylene foam, polyimide foam, aerogel, ethylene-propylene-diene monomer, epichlorohydrin, and the like. In some embodiments, the insulating barrier is primarily for patient comfort, rather than preventing the transmission of heat. In such instances, preferred materials may include cotton fabrics, polyester fabrics, paper fabrics, fabric blends thereof, and the like. The thickness of the insulating barrier 28 will generally range from about 0.001 to about 0.5 inches, and more preferably from about 0.01 to about 0.2 inches. As a practical matter, particularly for use in supporting injured limbs and body parts, it is also desirable that the average exterior surface temperature of the device not exceed 120° F.

In one or more embodiments, phase change materials can be included in the composite article to absorb some of the energy from the exothermic curing reaction of the resin (discussed below). For example, films, sheets, liquids, powders, beads, or flakes which will melt upon reaching a certain temperature in the curing reaction can be used. The position of the phase change material can vary widely. For example, as noted above, a layer comprising phase change material(s) can be present between the fiber reinforcement and encapsulating film. Alternatively, the phase change material can be used in lieu of an insulating barrier (e.g., on one or both sides of the composite major surfaces). The phase change material could also be used in addition to the insulating barrier between the encapsulating film 26 and the insulating barrier 28 (e.g., on one or both sides of the composite major surfaces) (not shown). Exemplary phase change materials include liquids that vaporize between 110° F. and 180° F. and polymers or waxes that melt between 110° F. and 180° F., such as polycaprolactone, beeswax, paraffin wax, and the like.

In one or more embodiments exemplified by FIGS. 30-34, a source of light 230 can be included to catalyze and cure the resin 212. For example, LEDs in various arrangements such as individual LEDs, flexible strips, and flashlights, electroluminescent panels, electroluminescent wires, chemiluminescence devices, UV-light, incandescent lamps, halogen lamps, and fiber optics could be used to provide the light required to cure a light or photo-catalyzed resin in certain embodiments. The light source 230 may be placed above, below, along the edge, or within the prepreg compartment 220. In one or more embodiments, the light source may be in a removable compartment such that it can be separated from the splint after the composite has cured. Since some light sources may be visible on x-rays, having a removable light source will reduce obstructions during x-ray imaging of patients. Furthermore, the removable light source may be used to cure multiple splints and thus reduce waste. A power source 234 and switch 232 for the lights may also be included. Example power sources include a battery or batteries, capacitor or ultra-capacitor, power converter, voltage multiplier, solar cells, and the like.

In one or more embodiments, a spacer 222, diffuser, and/or reflective material 224 may be used to promote the spreading of light. Preferable spacers are flexible and lightweight. In some cases, such as when top emitting LEDs are used as the light source 230, the spacer 222 may need to be translucent. Example spacers include tubes, corrugated materials, an array of posts, foam, and poly film with encapsulated pockets of gas, liquid, or gel. Preferable diffusers are flexible, lightweight, and spreads light which passes through it. Example diffusers include clear plastic sheets or films with a scratched or etched surface, translucent materials, liquids or gels containing refractive or reflective particles, and the like. Preferable reflective materials are flexible, lightweight, and reflect visible light. Example reflectors include Mylar film, metal foils, laminated films with metal foils, glass beads, titanium dioxide powder, reflective paint, reflective tape, and the like. Both smooth and textured reflectors are suitable for use in the invention. In some cases, a single component may serve as both a reflector and an encapsulating film, such as heat sealable laminated foil. Furthermore, in some cases, a single component may serve as both a spacer and a reflector, such as corrugated foil.

As noted above, the precursor article is flexible, bendable, and conformable before curing. The layers in the multi-layer article can be initially held together using any suitable technique, including adhesives, glues, tapes, mechanical fasteners, such as staples or thread, and the like. This improves the distribution of the resin by reducing gapping between the reinforcement plies and gapping between the resin distribution tube and the reinforcement. Spray-on adhesives and bonding agents are particularly useful in the invention.

Suitable resins for use in the invention will be thermosetting resins capable of rapidly and irreversibly curing (aka polymerizing or crosslinking) in under about 10 minutes, preferably in less than about 5 minutes, more preferably in less than about 3 minutes, and even more preferably from about 15 second to about 3 minutes to a substantially rigid form. Low viscosity, thermosetting resins (and preferably very low viscosity resins) are particularly preferred to facilitate full wet out of the fiber reinforcement when the resin is introduced into the composite article through the distribution process. For example, resins having a viscosity of less than about 100 cps, and preferably less than about 10 cps at 70° F. can be used in the invention. Such resins are often referred to as "wicking grade" adhesives for their ability to wick through and fully wet out the substrate to which they are applied. For the prepreg variation, a higher range of viscosity is preferred with a minimum of 100 cps at 70° F.

In one or more embodiments, the thermosetting resin is a cyanoacrylate-based resin system. Cyanoacrylate resins cure and polymerize rapidly via inherent reactions with the fiber reinforcement, or through the aid of the accelerant or moisture on the fiber reinforcement surfaces. Exemplary cyanoacrylate resins for use in the invention include methyl cyanoacrylates, ethyl cyanoacrylates (super glue), butyl cyanoacrylates, octyl cyanoacrylates, and combinations thereof, with ethyl cyanoacrylate being particularly preferred. Various rapid setting cyanoacrylate-based resin systems are commercially available, with several resin systems discussed in the working Examples. Cyanoacrylates can be used alone or in combination with other polymers (e.g., polyacrylates or polymethacrylates) or fillers. Fillers will reduce the amount of resin required to wet out the entire volume and surface area of the fiber reinforcement, and include alumina, calcium carbonate, talc, and the like. In one or more embodiments, the fillers can also act as phase change materials, such as plastic or wax beads, powders, or flakes included in the resin composition, which will melt with the resin upon reaching a certain temperature in the curing reaction.

In one or more embodiments, the thermosetting resin is an oxygen-sensitive resin system (aka air catalyzed resin). Exemplary systems include beta diketone-activated systems, aromatic tertiary amine-activated systems, and the like. These systems rely on the activator that reacts with oxygen in the air to catalyze a series of reactions that eventually results in the polymerization of vinyl monomers. These systems will generally comprise a polymerizable monomer (e.g., ethylenically unsaturated monomers, such as acrylates), a metal salt, a weak acid, the oxidizable activator, and an optional free radical stabilizer. Thus, these systems can also be characterized as air-catalyzed polyacrylate systems. A weak acid is defined as an acid that only partially dissociates in a solution, such that both the acid and the conjugate base are present in solution at equilibrium. Exemplary ingredients for each system are listed in the working examples below. Examples of acrylates or methacrylates include methylmethacrylate, methylacrylate, hydroxypropylmethacrylate, di-acrylates or di-methacrylates including ethyleneglycoldimethacrylate, diethyleneglycoldiacrylate, tri- and tetra-acrylate and methacrylate monomers. Examples of metal salts include cupric, cobalt and iron naphthenates, cupric, cobalt and iron acetylacetonates, and other soluble or partially soluble transition metals. Examples of weak acids include saturated acids such as acetic, chloroacetic acid, and dichloroacetic acid and unsaturated acids such a methacrylic acid. Air oxidizable beta diketones include methyl 2-oxocyclopentane carboxylate (MOC), 2-methyl-1,3-cyclohexanedione (CHD), 2,2-dimethyl-1,3 dioxane-4,6-dione, 3-methyl-2,4-pentadione, 2-methyl-1,3-cyclopentanedione, and 2-acetyl-1,3-cyclohexanedione. Examples of air oxidizable tertiary amines include N,N dimethylaniline and 4,N,N trimethylaniline. Examples of free radical stabilizers include 4-amino-2,2,6,6 tetramethyl-1-piperidinyloxy (amino-TEMPO), 4-hydroxy-2,2,6,6 tetramethyl-1-piperidinyloxy (OH-TEMPO), 2,2,6,6-tetramethyl-1-piperidinyloxy (TEMPO), phenothiazine (PTZ), methyl hydroxybenzoate (MHB), and tributyl phosphite (TBP).

In one or more embodiments, the thermosetting resin is a photo-catalyzed (aka photo-curable) resin. Preferably, the photo-curable resins are ones that are catalyzed by light energy, such as visible, blue, UV, near-UV, and the like. More specifically the selected resins are ones cured by light energy having a wavelength between about 350 and about 500 nanometers, more preferably between about 450 and about 495 nanometers, and even more preferably about 470 nanometers. Exemplary photo-curable resins include single component/one-part resins systems, such as resin systems with vinyl unsaturated compounds that cure by free radical or ionic polymerization, including acrylates, methacrylates, vinyl esters, polyesters, and the like. Photo-curable resins are commercially-available, including RCT 01 1065 UV from Rapid Cure Technologies, RBCX-15-82-1 from RBC Industries Inc., and 733984 from Sunrez Corporation.

Figure 30:
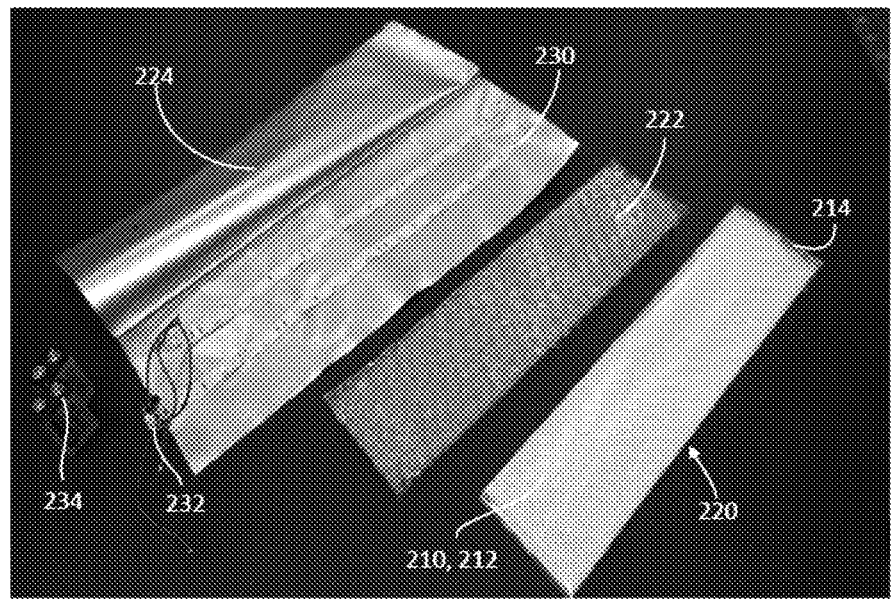
FIG. 30 is a photograph of the disassembled components of the photo-cured composite article.
Figure 31:
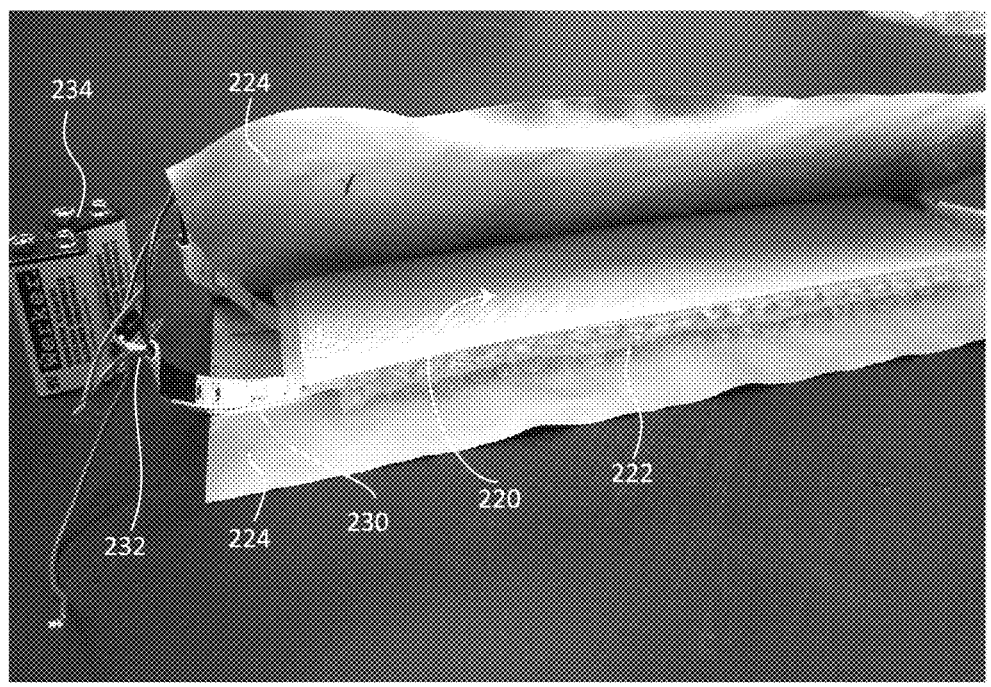
FIG. 31 is a photograph of the inner components of the photo-cured composite article as assembled in one embodiment.
Figure 32:
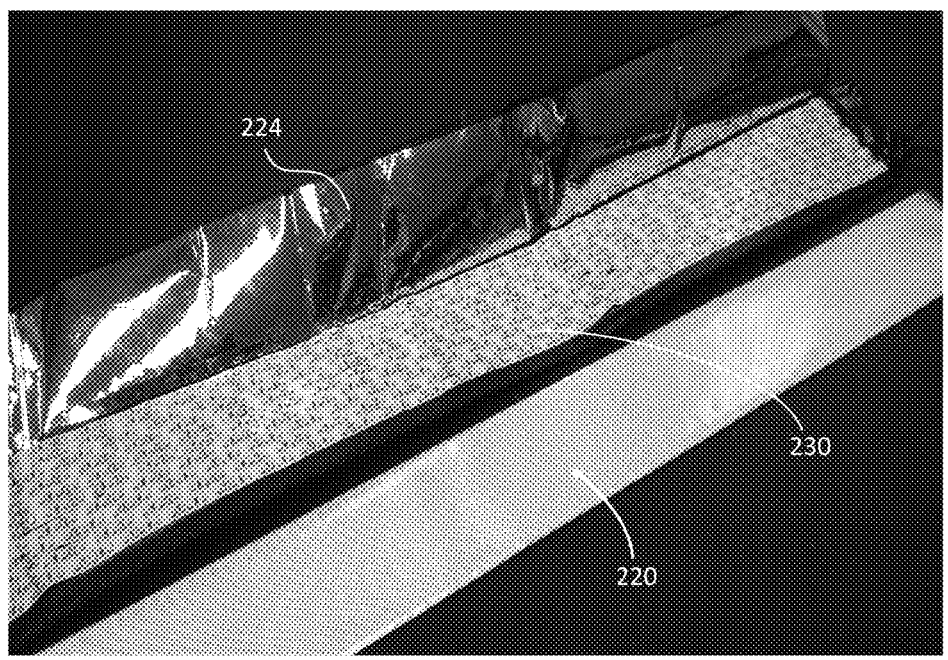
FIG. 32 is a photograph of an alternative light source arrangement, including a reflector.
Figure 33:
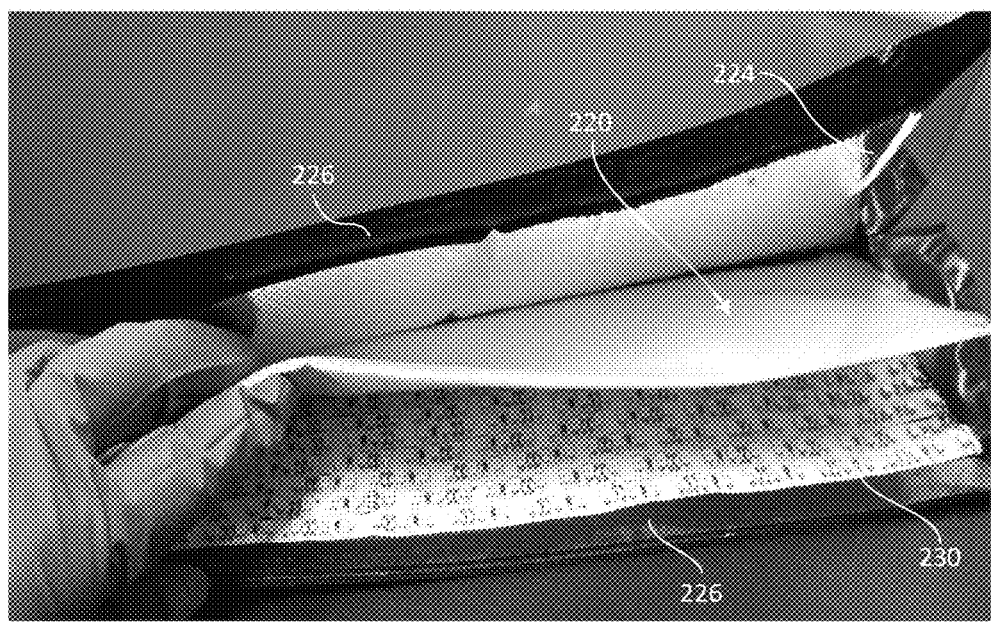
FIG. 33 is a photograph of an assembled multi-ply photo-cured composite article according to an embodiment.
Figure 34:
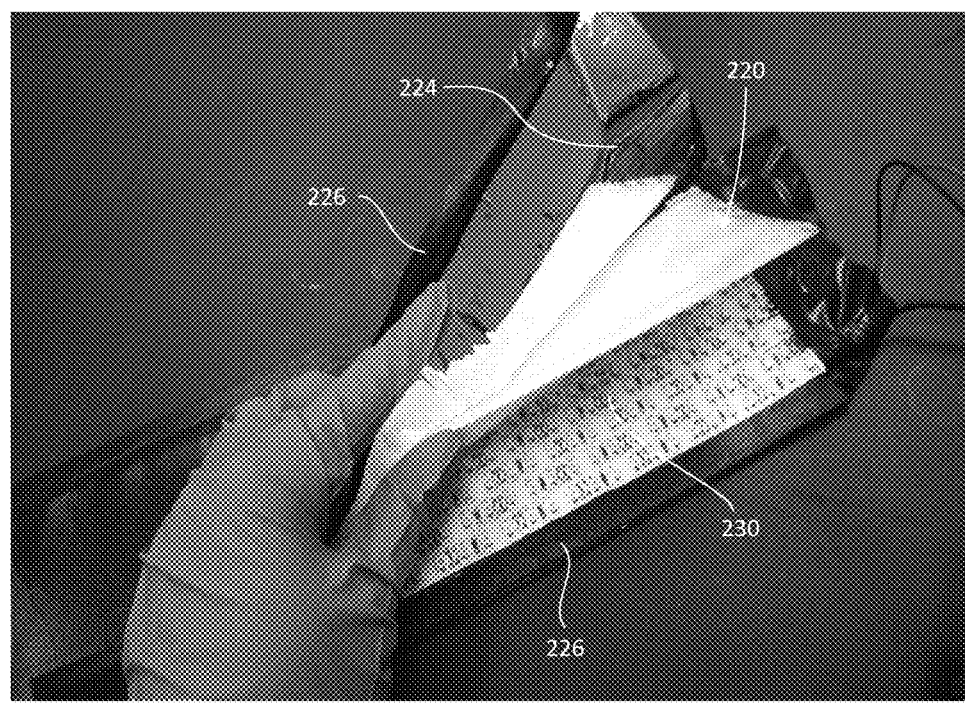
FIG. 34 is a photograph of an alternative view of the multi-ply photo-cured composite article.

Shown in FIG. 30, photo-curable resins 212 are preferably provided as part of an encapsulated fiber compartment 220, with the resin 212 pre-infused into the reinforcement plies 210 in an encapsulating film 214 to form a multi-layer, prepreg, composite precursor body. Thus, the multi-layer body will also include a light source 232 and appropriate power source 234, along with optional spacers 222, diffusers, and/or reflectors 224 as described above to facilitate dispersion of the light for full curing of the composition article throughout the precursor body. Additionally, shown by FIGS. 33 and 34, the aforementioned elements of the multi-layer body may be enclosed within an insulating barrier 226.

Additional types of resins requiring an external catalyst could also be used, provided they supply the required rapid curing and the desired rigidity upon curing. For example, these resins can be exposed to the selected catalyst, such as by injection, submersion, breaking or puncturing catalyst filled containers such as pouches or spheres, release of a pressurized gas or liquid from a cartridge in the composite, or by more passive techniques (e.g., simply exposing to ambient environment).

Figure 6C:
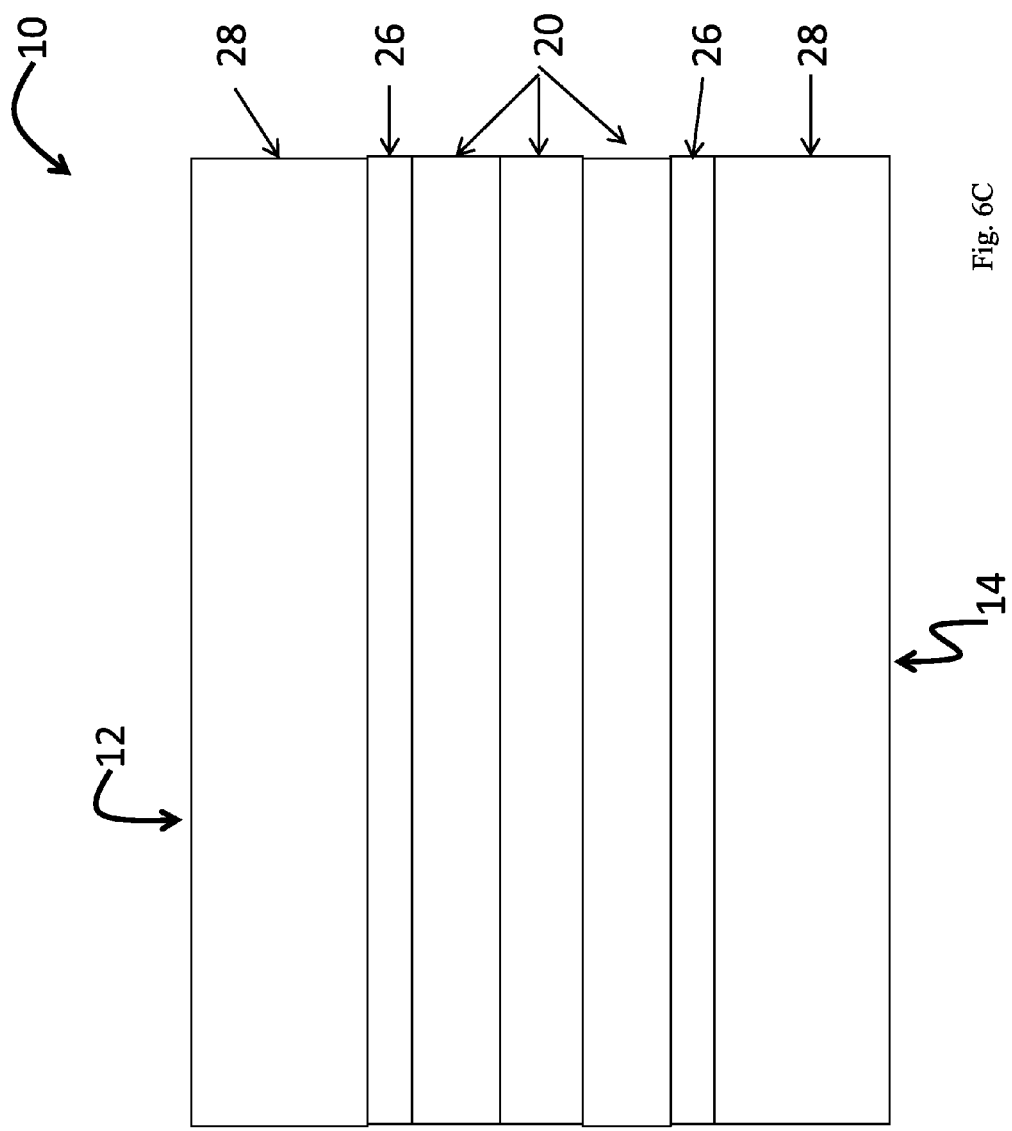
FIG. 6C is a longitudinal cross-section of a multi-layer sheet in accordance with an alternative embodiment of the invention.

It will be appreciated that in these activated systems, the composite article can be provided as a prepreg with the uncured resin 212 already infused into the fiber reinforcement plies 210 in a separate and sealed compartment 214, exemplified by FIGS. 30-34, thus forming an encapsulated fiber compartment 220. The article can be stored under inert conditions (away from the catalyst and/or light) in a sealed container until use. Thus, in one or more embodiments, as shown in FIG. 6C, as well as in FIGS. 30-34, the distribution tube is not included in the article. Alternatively, the distribution tube as depicted in FIGS. 6A and 6B may still be present and used to inject the catalyst into the article to further facilitate rapid curing.

In use, the composite precursor can be shaped to conform to the injured limb or body part, for example, by wrapping the composite precursor around the injured body part (e.g., as in a traditional circumferential cast), or otherwise placing the precursor next to and in conformance with the injured body part, but not circumferentially wrapping the body part (e.g., as in a sugar-tong splint, or whole-body immobilization board). The composite precursor will generally be placed with the back surface of the article adjacent the body part (e.g., skin or tissue of the injured part). Various techniques for supporting and immobilizing injured body parts include the volar splint, ulnar gutter splint, thumb spica splint, long arm splint, sugar-tong splint, and stirrup splint. In any event, the composite precursor is preferably shaped such that it provides some degree of compression to immobilize and support the injury. Compression can be achieved using the composite precursor itself, alternatively in combination with additional tapes, bandages, straps, or combinations thereof.

The thermosetting resin can then be injected into the precursor via the resin distribution tube (or alternatively, is already present in a precursor prepreg embodiment), and allowed to cure according to the appropriate curing mechanism for the selected resin. The multi-ply precursor cures in a laminar unitary structure having sufficient rigidity to support and/or immobilize the injured body part. As noted above, the resin will preferably cure to a rigid cured composite article in less than about 10 minutes, preferably in less than about 5 minutes, more preferably in less than about 3 minutes, and even more preferably from about 15 seconds to about 3 minutes. The rigid composite article is a lamellar body, with the fiber reinforcement plies being laminated together to form a substantially unitary fiber-reinforced core structure that is resistant to delamination.

The cured composite article can be further affixed or secured to the injured body part using any suitable method, such as adhesive tapes, elastic bandages or wraps (e.g., ACE), straps, and the like, which can be fastened using adhesive, metal clips, hook and loop fastener, and the like. In one or more embodiments, the securement devices can be integral (attached or affixed) to the composite article itself, instead of being provided as separate devices. In one or more embodiments, the article can be used to support the whole body or substantially the whole body. For example, the precursor can be sized to extend from head to waist, head to toe, or around the torso of the patient. The patient can be placed or laid onto a flexible sheet of the precursor article. The precursor could be cured in this flat form, or it could be pulled up and even wrapped around towards the front of the patient to form a custom-shaped full body splint. It will be appreciated that numerous variations of this embodiment exist, such that the article may not be a full wrap from head to toe. As such, an advantage of the inventive article is the ability customize the size, shape, and/or configuration of the article before curing, depending upon the situation, the injury, and other constraints. The shape of the precursor can include wide strips that could be placed over certain sections of the body, such as the upper chest, waist, thighs, and/or ankles to restrain the patient once cured. The precursor could also be cured on a substantially flat surface to create an immobilization board, before placing the patient onto the cured article. This embodiment of the invention could be used in place of or along with a standard spine board. Typically a patient is strapped to a spine board while laying on the ground. Once strapped to the board, they are then placed atop a stretcher and strapped to the stretcher. The full body splint could be strapped to the spine board, or it could replace the spine board and be strapped to the stretcher.

When cured, the formed composite article will have an average (median) maximum flexural load of at least about 10 lbs., preferably at least about 20 lbs., and more preferably from about 60 to about 80 lbs. The cured composite article will also have an average (median) stiffness of at least about 50 lbs./in., preferably at least about 75 lbs./in., and more preferably from about 100 to about 200 lbs./in. The maximum flexural load and stiffness are determined by performing a four-point bend test of an 18" specimen with a support span of 14" and a loading span of 3". The specimens are formed to a 4" diameter curvature along its length as it would have in normal practice. Support fixtures have matched 4" diameter curvature to hold the specimen during testing. Matched fixtures are not used on the load points on the loading span fixture. This test procedure is based on ASTM Test Standard D7249 Standard Test Method for Facing Properties of Sandwich Constructions by Long Beam Flexure.

In one or more embodiments, the composite article is preferably substantially radiolucent, so that the body part can be imaged and examined using x-rays without having to remove the article. It will be appreciated that this provides an advantage of continuously supporting the injured body part through the imaging process. This is particularly important in the case of spinal injuries. For example, in one or more embodiments, x-ray images are taken before removing the patient from the immobilization board or full body splint. It will be appreciated that in the case of the photo-curable composite, certain light sources used to cure the composite will be visible on x-ray images. Therefore, it would be best for such a light source to be removable and re-usable. In this case, the insulated/encapsulated precursor would be placed on top of the light source. The light source would be flexible and conformable, so that it could be wrapped up and around the patient with the precursor. Once cured, the light source is no longer needed, and it can be unwrapped while the cured composite remains with the patient. The patient can then be lifted up and off the light source, while the cured composite maintains support on the injured body part. Since the cured composite is radiolucent, it will not interfere with the x-ray images.

As it will be appreciated, since the precursor article is extremely pliable and flexible before curing, it can be molded and shaped into many different configurations before curing. It can also be folded or rolled for storage and portability. Thus, it provides a lightweight and rapid solution for supporting and/or immobilizing any number of different parts, shapes, and anatomies of the body or injuries. As used herein, the terms "injury," "injuries," "injured" and the like, include bone or soft tissue damage, such as breaks, fractures, sprain, strains, as well as "intentional" injuries such as from surgery. Thus, the composite precursor is generally provided as part of a kit for physicians, nurses, first responders, military personnel, and the like, or even as part of a first aid kit for use by various individuals (e.g., in the home, for sporting events, outdoor activities, etc.). The kit will include the composite precursor, preferably in a sealed package, along with the thermosetting resin, and an instruction manual for their use. Depending upon the embodiment, the thermosetting resin will be provided in a container separate from the composite precursor, or it can already be present in the packaged precursor as a prepreg in a separate compartment. In one or more embodiments, the thermosetting resin can be provided in a container, such as a syringe, pouch, or bottle suitable for delivering the thermosetting resin to the composite precursor. Additional bandages, tapes, etc. can also be included in the kit, or integrally attached to the precursor, as noted above. Other first aid supplies such as antibiotic ointment, straps, gauze, and combinations thereof can also be included in the kit.

Various kits can be configured to be specific to certain body parts or types of injuries, based upon the size and/or shape of the composite precursor and amount of thermosetting resin provided. Exemplary sizes in which the composite precursor can be provided include strips, ropes, or sheets having a width or diameter ranging from 0.5 inch to 16 inch, more preferably from 1 inch to 4 inch, and a length ranging from 2 inch to 60 inch, more preferably from 12 inch to 40 inch.

The present invention provides several additional advantages over conventional splinting materials. For example, the rapid setting resin does not require water or the use of any additional components to achieve sufficient rigidity and/or stiffness. This provides a distinct advantage for use in emergency situations where water, for example, may not be available. The rigidity and stiffness of the composite article also does not rely on extraneous physical reinforcement such as by metal or metallic reinforcements, such as metal or metallic rods, stiffeners, ribs, flanges, and the like, further decreasing the weight associated with the composite. That is, the rigidity of the composite article is achieved solely by the multi-layer composite cured resin and fiber reinforcement. In one or more embodiments, except where potentially present as a metallic foil in the encapsulating film (which provide little to no rigidity), the composite is preferably essentially free of any metals. The composite is more preferably essentially free of any metal reinforcements, which refers to metal or metallic components that are responsible for the strength and rigidity of the article (i.e., contribute to more than 50% of the rigidity of the composite). In one or more embodiments, metal plies can be included in the composite to increase rigidity of the cured resin. In contrast to previous metal-based supports, however, thin metal plies would be used to support and/or increase the rigidity of the multi-layer composite, but would not be the sole or primary source of rigidity in the device. The metal plies would include either solid thin sheets, or mesh/screen (i.e., permeable) plies of metal that would be encapsulated with the encapsulating film along with the fiber reinforcement to further increase the rigidity of the cured article.

The cured composite is sufficiently rigid, while maintaining low weight and volume. For example, in one or more embodiments, the cured composite has a weight of less than about 500 grams, preferably from about 50 to about 500 grams, more preferably from about 75 to about 400 grams, and event more preferably from about 85 to about 300 grams for a 3"×36" sized composite article, not including external packaging materials or a resin injection device. The kit as a whole, including the packaging and resin injection device (e.g., syringe), will weigh less than about 750 grams, preferably less than about 500 grams, and more preferably from about 50 to about 500 grams, depending upon the size of the composite article itself. The density of the cured composition ranges from about 0.463 g/in.$^2$ to 4.63 g/in.$^2$ (0.001021 lbs./in.$^2$ to 0.01021 lbs./in.$^2$).

It will be appreciated that although the disclosure herein focuses primarily on use of the composite for immobilization and/or support of injured limbs and/or other body parts in humans and animals, the composite article also finds usefulness in a number of unrelated areas where a rapid-setting rigid article may be needed, including as a general purpose stick, patch, stiffener, support, etc., which could be used to prop up a car hood or a tent, etc. The article may also be used to make shelters or tents, sleds, orthotics, prosthetics, external fixation devices, snow shoes, or body armor, shields, or guards for protection during a variety of activities, including industrial work, sports, combat, and the like.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Resin Distribution Systems

Figure 7:
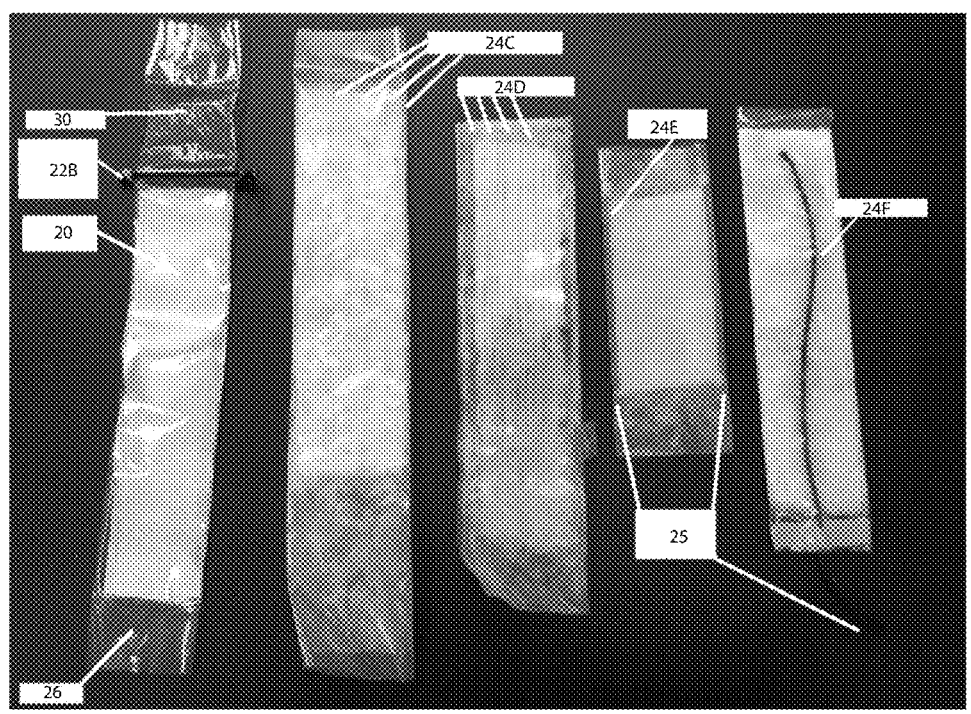
FIG. 7 is a photograph of the various resin distribution systems tested in Example 1.
Figure 8:
FIG. 8 is a photograph showing the resin distribution experiments using a vacuum-based resin distribution system.

This example describes testing of various resin distribution system concepts and additional development testing of one particular concept. The function of the resin distribution system is to evenly distribute the resin throughout the reinforcement so that even wet out is consistently achieved. Multiple concepts for distributing resin to fabric were tested. In general, the system concepts involved storing resin in a pouch or enclosed container that would allow stable storage of the resin and a physically controllable method of release to distribute the resin to a separately sealed package containing the reinforcement fabric. Multiple methods were investigated to accomplish this: passive resin wicking into the fabric; using hand or squeegee to manually force or palpate resin into the fabric; resin distributed onto the fabric through a surface barrier perforated with holes or slits; resin forced through a tube with either holes, longitudinal cuts, spiral cuts, or periodic slits along its length; resin distribution systems integrated into the packaging by heat sealing; channels or tubes with longitudinal slits placed over the edge of the reinforcement; resin distribution aided by vacuum packaging the fiber containment system and/or by actively pulling a vacuum on the system during resin infusion; and resin diffused and/or forced across a semi-permeable membrane. FIG. 7 and FIG. 8 show examples of some of these concepts. All of these concepts underwent prototype trials.

A packaging system that encapsulated both the resin and the fiber reinforcement was constructed that keeps the two in separate compartments, but then allowed a barrier to be removed. Once the barrier was removed, a tool was used to manually squeegee the resin along the length of the specimen, simultaneously impregnating the fabric with resin and consolidating the plies.

Active resin distribution systems were investigated in multiple formats. Resin distribution channels were formed into the packaging enclosures using a heat sealer, leaving open spaces in the channels to allow resin to leave the channels and impregnate the fabric. Channels were heat formed into the plastic encapsulating film along the full length of the product at its centerline, along its two long edges, and at one-third and two-thirds across its width. Barrier films with holes and/or slits to allow controlled resin distribution were also examined. Multiple heat sealed distribution and film distribution patterns were investigated, but more consistent results were found when resin distribution tubes were used.

Systems that employed a syringe injecting resin through a plastic tube(s) perforated with holes generated the most promising results. Additional trials with perforated tubes were conducted to investigate placement of the tube (on top or between plies); methods of securing the tube (straight and zigzag longitudinal stitching on either side of the tube with the tube between plies, periodic stitches across the tube, putty-like tape, and spray adhesive); the number of tube(s) and interconnections; the length of tube(s); and the position of tubes (zigzag; branching, parallel, and looped).

Resin distribution systems using tubes of internal diameters varying from 0.025 inch to ⅛ inch were tested with small diameter (0.0059 inch to 0.05 inch) holes punched or drilled throughout their length. Fiberglass fabric samples of size 2.5" in width, 9" long, and 3 plies thick were prepared. Small diameter tubes, with length of 12 inches were sewn between the three plies. The fabric and tube constructs were then placed in sealed plastic packages with a few inches of the tube extending out from one of its ends. A luer-lock adapter was attached to the tube's inlet, and using a syringe, 10 mL of cyanoacrylate was injected into the tube. (FIG. 9) When the resin was injected into the tube, it exited through the holes along the tube and wicked through the fiberglass, immediately impregnating the reinforcement and curing to a stiff composite.

Figure 10:
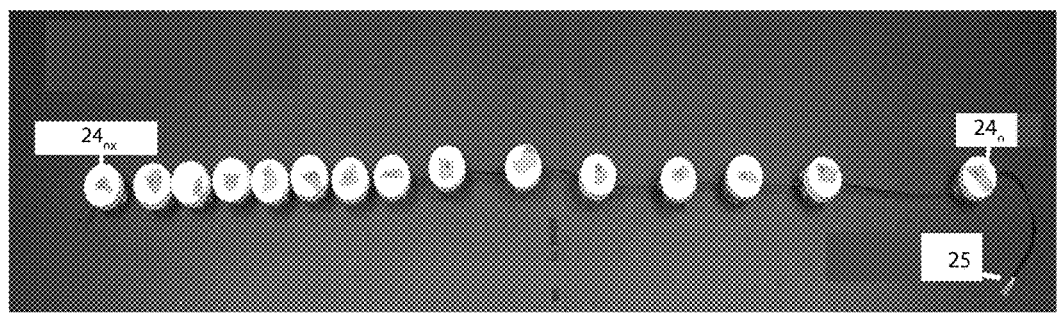
FIG. 10 is a photograph of the set-up used to evaluate resin distribution through a perforated tube, using water as proxy for the resin.

While there were many variables associated with the tube, the distribution system trials focused primarily on the effects of tube diameter as well as the size, spacing, number of holes, and manufacturing methodology on uniformity of resin distribution. At each designated hole spacing, varying sizes of were cut out on both sides of the tube. Methodologies used to create these holes included cutting with different gauges of needles, punching, manual drilling, laser drilling, and computed numerically controlled machining. Through these trials, it was discovered that for this specific construct, hole spacing of increasingly smaller distances were required at the far end of the tube to produce a more even distribution along the length of the fabric. Trials also showed that the product had more consistent resin distribution when a higher number of holes with smaller diameters was used than when holes of larger diameter were used. It was also found that the resin distribution system has to be re-evaluated when the materials, orientation, or scale of the product changes. Further testing was conducted to investigate the flow characteristics of full length tubes (3 ft. long). Initial trials used water in place of cyanoacrylate because water has a viscosity very close to low viscosity cyanoacrylate, is easier to handle, and is readily available. The water trials were conducted without fabric so that the volume of water ejected at each hole along the length of the tube could be collected and recorded. FIG. 10 shows the test setup for one resin distribution configuration. The measured water amounts were used to compare distribution characteristics of different tube diameters, hole diameters, and hole spacing.

Figure 11:
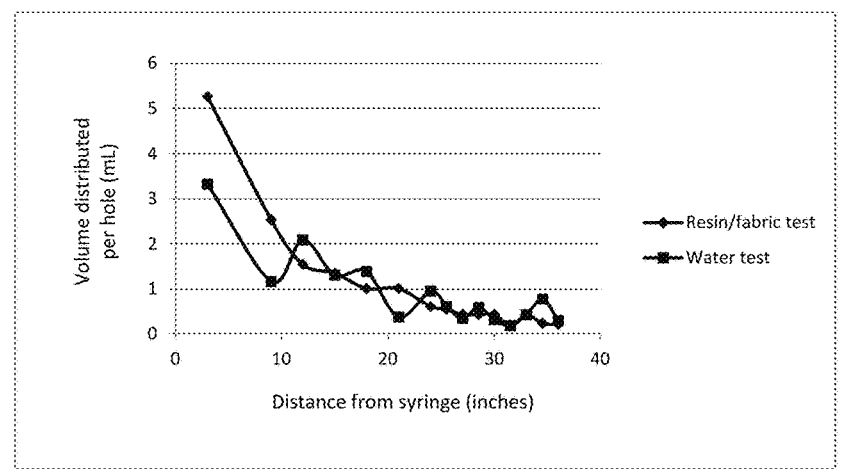
FIG. 11 is a graph of the results showing that water could be used to approximate the flow of resins, based upon fluid distributed per hole (water versus resin)

In order to verify the validity of the water distribution model, a comparative full scale resin test was run with the same hole spacing. (FIG. 11) Although some discrepancy was seen, this comparison shows that substituting water for the low viscosity cyanoacrylate resin provided a good approximation of resin distribution across the length of the tube and was a suitable means for rapidly testing design variations.

The testing methods thus far yielded some insights into a prototype design. A prototype consisting of two to three tubes with each tube providing the resin to cure a 1 to 1.5 inch width section was preferred. It was found that many of the smaller tubes do not kink as easily, ensuring a more robust and versatile system. The use of multiple tubes also creates redundancy in the product, making it less prone to failure if one of the resin distribution tubes kinks or clogs.

Full scale testing with fiberglass, a low viscosity cyanoacrylate, and accelerant was commenced using a trial and error empirical approach, starting with the distribution design based on the simulated model. For the first round of trials, specimens (36 inch long and 3 inch wide) were tested on a flat surface. Those with the most uniform distribution were selected to continue to the next round of testing. The splint was applied to an artificial leg and the resin was injected in order to emulate the proper three-dimensional orientation and formation of the prototype. Working iteratively through these steps yielded prototypes that provide acceptable resin distribution.

Example 2

Cyanoacrylate Based Splint

The following is an overview of the cyanoacrylate composite splint. The first topic covered is the construction of the splint. This is included to provide an understanding of how the individual components of the product come together. This is followed by descriptions of testing on the various components.

1. Cyanoacrylate Splint Construction

Example components of a cyanoacrylate based splint are listed in Table 1.

TABLE 1

Components of a cyanoacrylate based splint

| Component | Product | Size/Amount per Splint |
|---|---|---|
| Resin | Wicking grade cyanoacrylate | 64 ml |
| Accelerant | Diethylol-p-toluidine | 27 ml of diethylol-p-toluidine in acetone |
| Reinforcement fiber | Fiberglass - Carolina Narrow Fabric 751524 | 3 plies, each 3" × 36" |
| Distribution Tube | 1/16" ID polyurethane tube | 75" of tubing with 1 barbed Y 1 barbed luer lock connector |
| Encapsulating film | Aluminized nylon film (heat sealable) | 2 sheets, each 4" × 38" Or 38" of 3" wide lay-flat tube |
| Insulating barrier | Polyethylene foam with adhesive backing | 2 pieces, each 3" × 36.5" |
| Tackifier | 3M Super 77 adhesive spray | Light spray coat on each ply of fiberglass and the encapsulating film |

Figure 12:
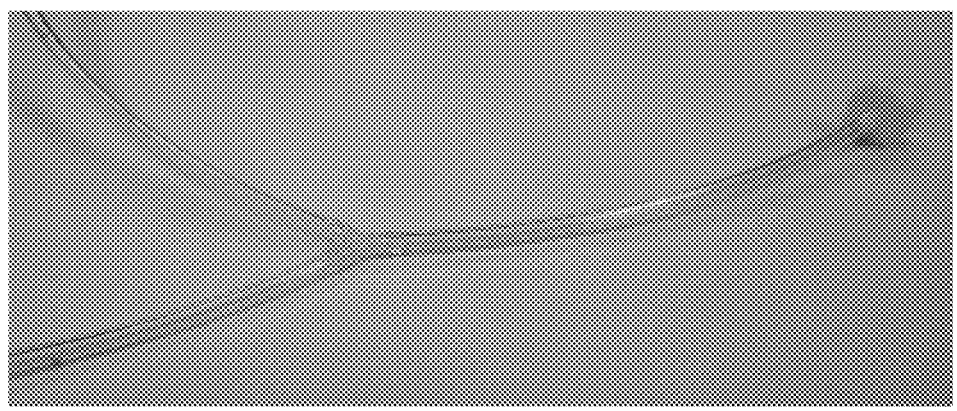
FIG. 12 is a photograph of the distribution tube used in Example 2, showing the barbed Y with drilled tube attached at exit ports and short tube with luer lock adapter at entry port.
Figure 13:
FIG. 13 is a photograph showing the distribution tube (clear tube under thumb and pointer finger) being placed onto a ply of fiber reinforcement.
Figure 14:
FIG. 14 is a photograph of the distribution tube placement in the composite with the looped end of the tube at top of the photograph and the Y end with luer lock at the bottom of the photograph.
Figure 15:
FIG. 15 is a photograph showing placement of additional plies of fiber reinforcement on top of the distribution tube.
Figure 16:
FIG. 16 is a photograph showing the placement of the encapsulating film over the fiber reinforcement plies to seal the plies between the films.
Figure 17:
FIG. 17 is a photograph of the splint applied to a dummy limb; black material is the insulating barrier; white straps are Ace Bandage used to secure the splint to the limb; straps may be included as an integral part of the final product.

The following describes how cyanoacrylate splint prototypes have been constructed.
1. The cut fiberglass was treated with the accelerant in solution. The solvent was allowed to evaporate.
2. The resin distribution tube (FIG. 12) was made as follows.
   a. Holes were drilled along 72" length of tubing. Spacing between holes was 0.5".
   b. The ends of the drilled tube were connected to the 'exit' legs of a three pronged barbed Y. On the remaining leg of the Y was placed a 3" long tube.
   c. A luer-lock connector was inserted on the open end of the 3" long tube.
3. The reinforcement package was assembled as follows.
   a. The reinforcement fibers and encapsulating film were laid on a table and coated with the tackifier.
   b. One ply of reinforcement fiber was placed on top of a sheet of encapsulating film and pressed in place.
   c. The resin distribution tube was then laid on top of the reinforcement fiber ply. (FIG. 13) The distribution tube consisted of a long loop with a Y at one end. Each side of the loop was approximately half way between the mid-line and edge of the reinforcement fiber ply. The short tube on the Y extended past the end of the reinforcement fiber ply. (FIG. 14)
   d. One at a time two plies of reinforcement fiber ply were placed on top of the distribution tube. After each ply was laid in place, it was pressed to adhere it to the ply below it. (FIG. 15)
   e. The reinforcement fiber plies were topped with a sheet of encapsulating film and pressed to adhere. (FIG. 16)
   f. The excess edges of the encapsulating film were trimmed. If the adhesive did not sufficiently seal the encapsulating film, the film could be heat sealed.
   g. The insulating barrier was adhered to each side of the reinforcement package.
   Note: At this point, the reinforcement package is conformable. It can be placed on the shelf and saved for use at a later date.
4. Depending on the evaluation, the reinforcement was placed either: (a) flat on a table top, (b) around a dummy limb (FIG. 17), or (c) curved on a 4" diameter cylinder. If testing required, thermocouple probes were placed on the outer surface of the insulating barrier (to get skin contact temperatures) and/or between the encapsulating film and insulating barrier (to get the composite's temperature profile during curing).
5. A large syringe was filled with cyanoacrylate, and connected to the barbed luer-lock connecter on the end of the distribution tube. Resin was then injected into the reinforcement package.
6. Within 90 seconds, the resin cured and the reinforcement package was a stiff and protective construct.

2. Resin Testing

Figure 18:
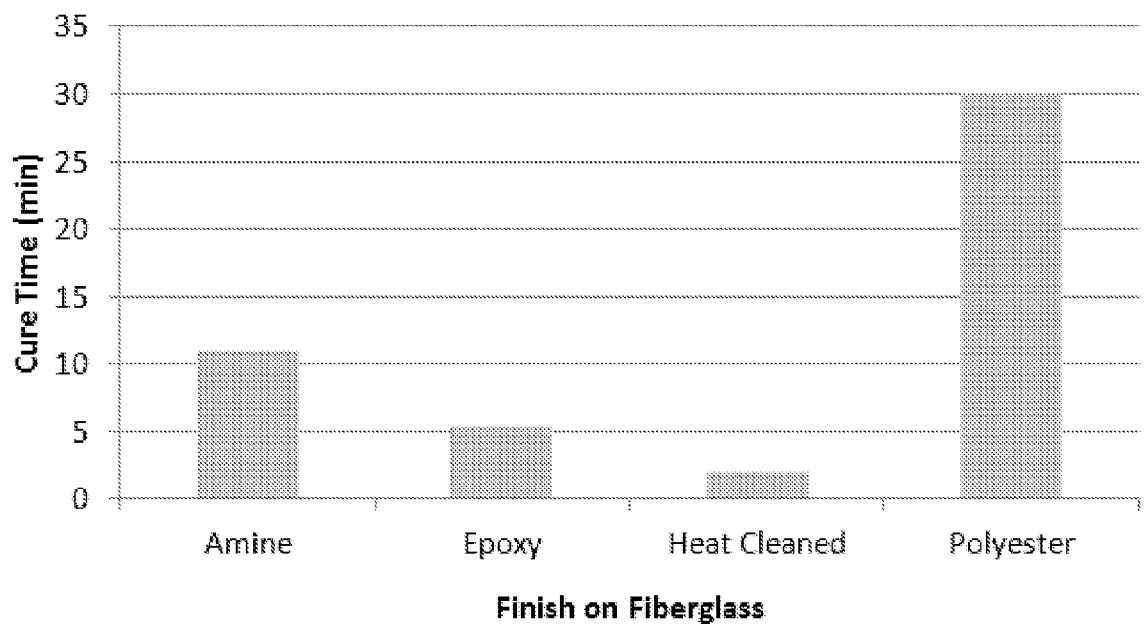
FIG. 18 is a graph showing the cure time of cyanoacrylate resin on fiberglass without accelerant.
Figure 19:
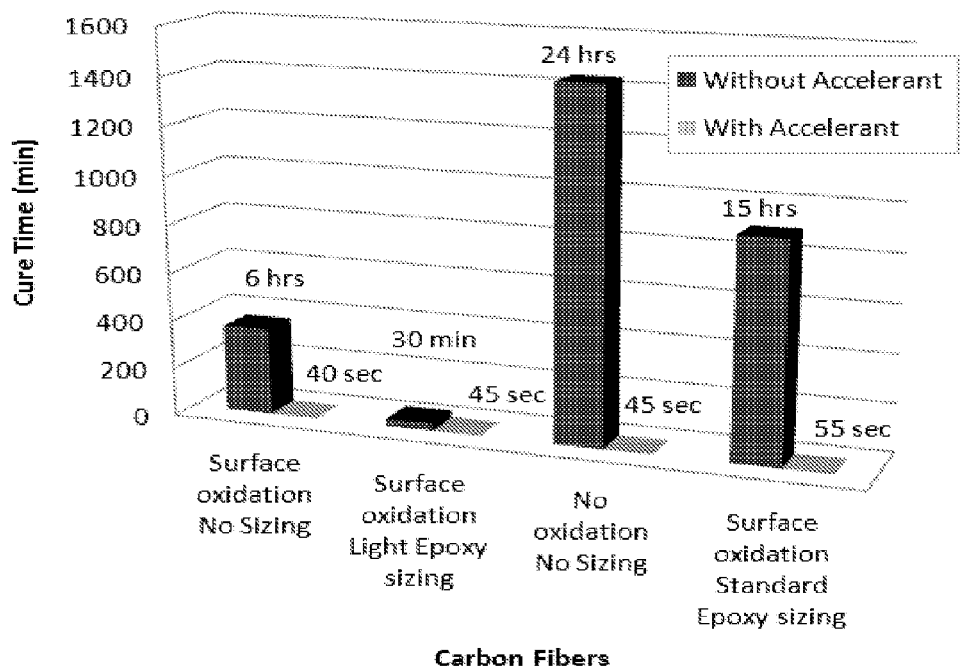
FIG. 19 is a graph showing the cure time of cyanoacrylate resin on carbon with and without accelerant.

In the following, cure time was a hand measurement of the point at which maximum stiffness of the composite was achieved. To conduct the test, 2"×2" swatches of reinforcement fabric were impregnated with cyanoacrylate resins and then evaluated by hand in terms of increased stiffness. The following generalizations were observed:

Cure times were different, but consistent, for each combination of cyanoacrylate, reinforcement fabric, and accelerant. Of the combinations evaluated, and the following cure time ranges were determined.
  Without Accelerant:
    40 seconds to 13 minutes on fiberglass
    30 minutes to 20 hours on carbon
  With Accelerant:
    20 seconds to 3 minutes on both fiberglass and carbon
The finish on fiberglass affected the cure time, and the fastest cure times are seen on fiberglass with no finish. (FIG. 18)
Variation in cure time can be reduced by adding an accelerant. (FIG. 19)
The concentration of the accelerant was indirectly related to the cure time. Thus, higher concentrations of accelerant produced shorter cure time. However there was a point at which the cure times were no longer reduced by additional accelerant. (Table 4)
Cure time was indirectly related to room temperature; as the room temperature was increased, cure time was decreased. (Table 6)

Figure 20:
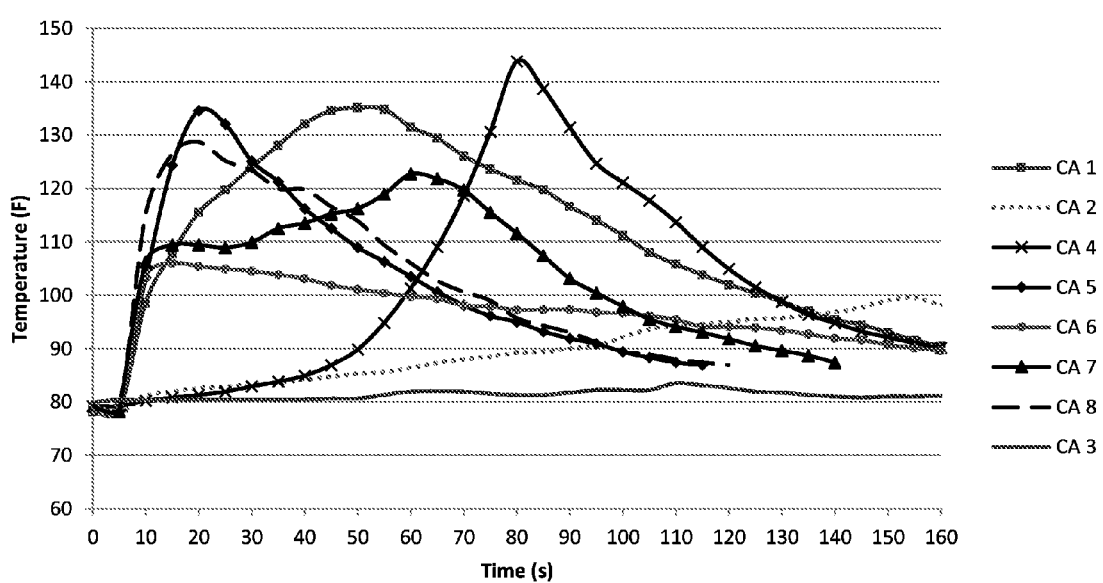
FIG. 20 is a graph of the exothermic response of eight different cyanoacrylate resins on fiberglass tested in Example 2.

Heat is produced during curing, and just as the cure time varies between the different cyanoacrylates, so does the thermal profile. FIG. 20 illustrates the curing temperature profiles for eight different cyanoacrylates. The peak temperatures on fiberglass without accelerant range from 90° F. to 145° F. while the time it takes to reach that peak temperature ranges from 7 seconds to 9 minutes. The peak temperatures on carbon treated with accelerant range from 105° F. to 185° F. while the time it takes to reach that peak temperature ranges from 11 seconds to 65 seconds. The accelerant reduces the variation in cure time between the cyanoacrylates, but it also increases the peak temperature.

Figure 21:
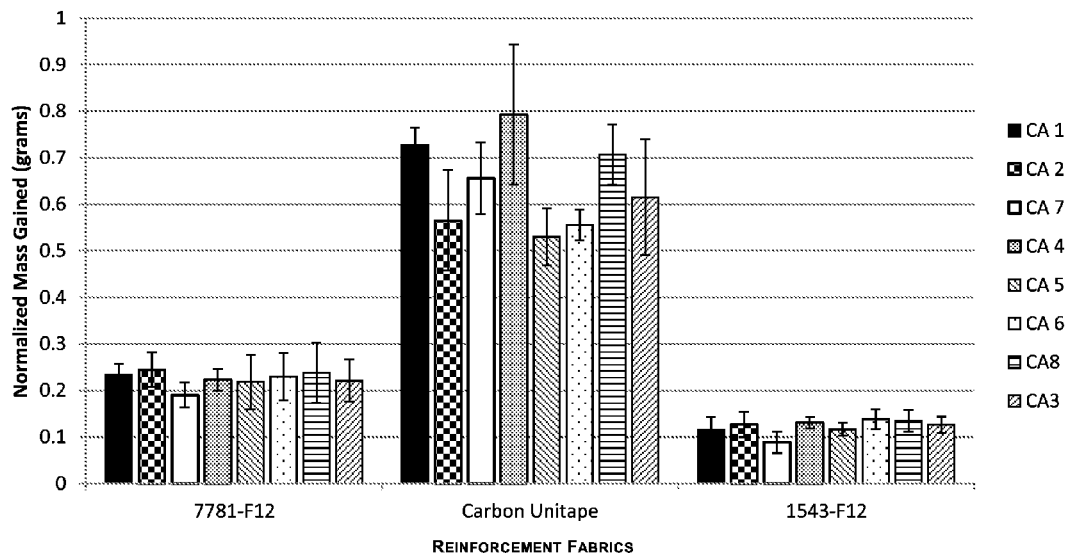
FIG. 21 is a graph showing the normalized resin gain during the wicking tests in Example 2.
Figure 22:
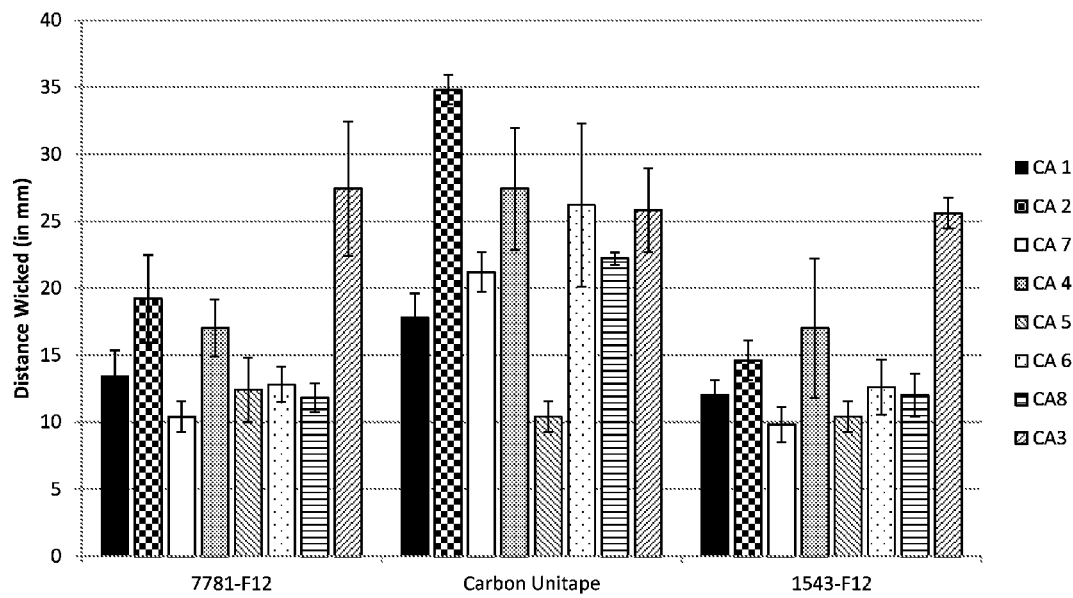
FIG. 22 is a graph showing the wicking distance from Example 2.

The ability of the resin to move or wick through the reinforcement is affected by both resin and fabric properties. To evaluate the wicking characteristics of various cyanoacrylates and fabrics, the edge of a fabric swatch (1 inch by 6 inch) was dipped into a small pool of resin and held for 30 seconds. Upon removal, the resin weight gain and the distance wicked were documented. Eight low viscosity cyanoacrylates were tested on three reinforcement fabrics, listed in Table 2. The volume of resin needed for a fiberglass composite is different than that of a carbon composite in order to achieve the same fiber to resin ratio; therefore, the weight of resin wicked by each specimen was normalized by dividing it by the weight of resin that would be required to achieve the same fiber/resin ratio. Results are presented in FIG. 21 and FIG. 22

TABLE 2

Reinforcement fabrics for wicking test

| ID | Material | Weave | Weight (grams/sq meter) | Warp to Fill Ratio |
|----|----------|-------|-------------------------|---------------------|
| FG3 | Fiberglass | 8 Harness Satin | 301 | 50/50 |
| FG5 | Fiberglass | 4 Harness Satin | 289 | 90/10 |
| CF6 | Carbon | Stitched Unitape | 194 | 100/0 |

3. Accelerant Testing

Accelerants may be applied to reinforcement fabrics to reduce cure time and reduce variability of cure times. To apply accelerants to reinforcement, a measured amount of accelerant is dissolved in a fast evaporating solvent, such as acetone or naphtha, and then a measured volume is distributed on the reinforcement fabric. The solvent evaporates and the accelerant remains evenly distributed on the fabric. Five accelerants, listed in Table 3, were evaluated in regards to their ability to initiate the curing and remain active for an extended period of time. Most of these were found to be volatile and were no longer active several hours after being applied to the reinforcement.

TABLE 3

Cyanoacrylate accelerants

| ID | Accelerant | Shelf Life | Cure Initiation |
|----|------------|------------|-----------------|
| A1 | N,N-dimethyl-p-toluidine | <1 day | Excellent |
| A2 | Tetrahydroxypropylethylendiamine | >1 day | Poor |
| A3 | Diethylol-p-toluidine | >1 day | Excellent |
| A4 | mixture of dipropylenetriamine, polyamine with epichlorohydrine and laurylamine, ethoxylated* | >1 day | Good |
| A5 | Water | >1 day | Good |

*Commercially-available as Dehyquart H81.

Figure 23:
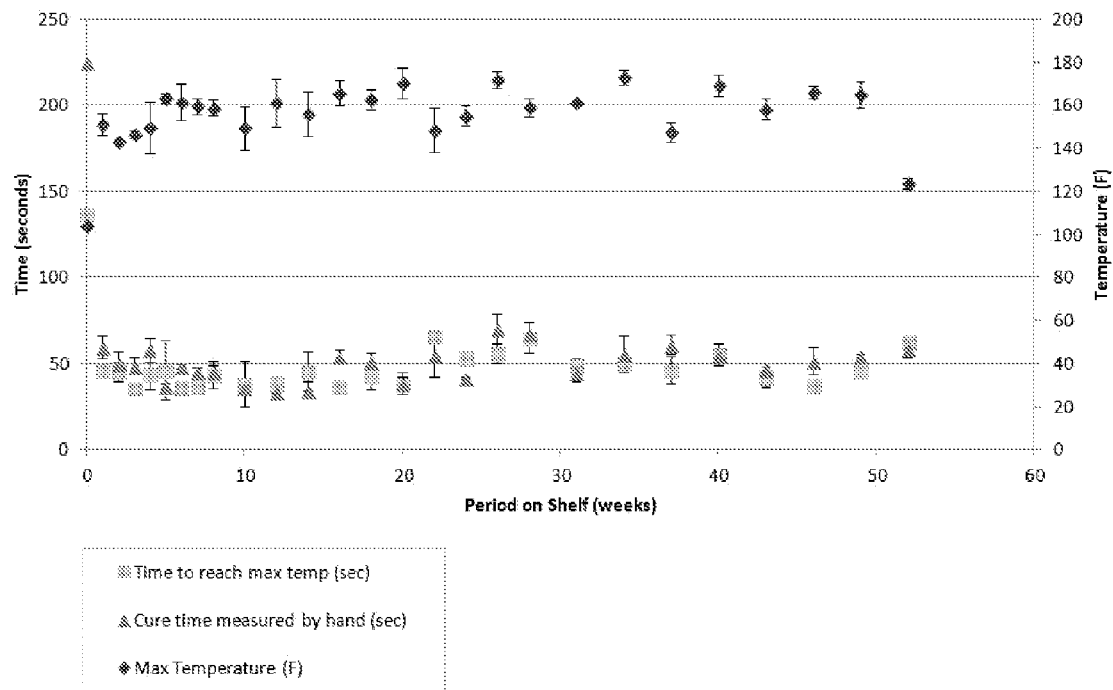
FIG. 23 is a graph showing the shelf-life on fiberglass of one of the accelerants (diethylol-p-toluidine) tested for use in the invention; Note: Data points on Week 0 represent fabric that was not treated with diethylol-p-toluidine.
Figure 24:
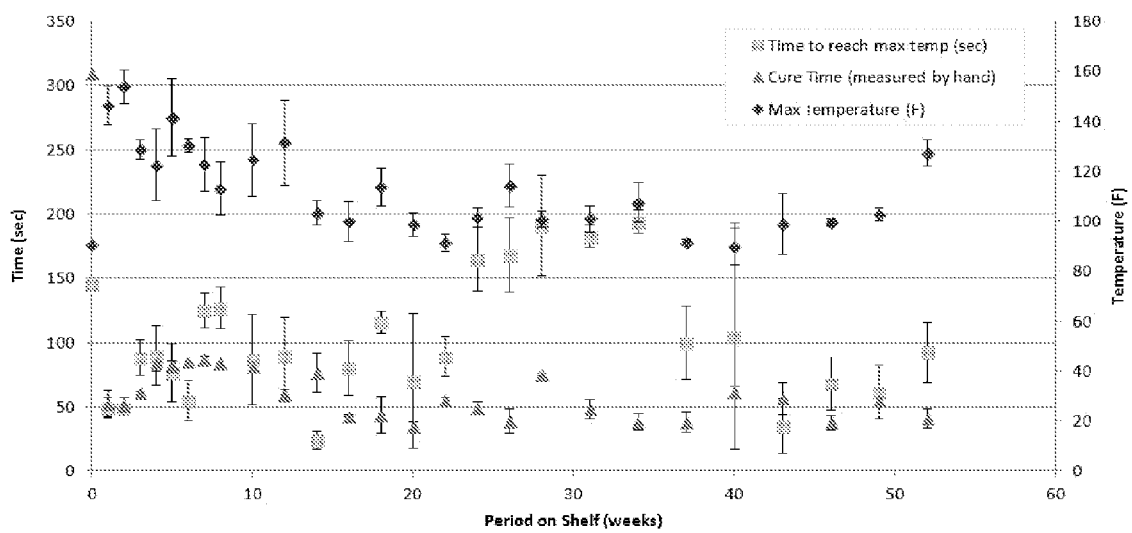
FIG. 24 is a graph showing the shelf-life in carbon of one of the accelerants (diethylol-p-toluidine) tested for use in the invention; Note: Data points on Week 0 represent fabric that was not treated with diethylol-p-toluidine.

Accelerant A3, diethylol-p-toluidine, was more effective at reducing cure time and less volatile than the other accelerants tested. To verify the long term viability of A3, shelf life testing was conducted on both carbon and fiberglass specimens treated with accelerant. A large number of specimens (3 plies, 1 inch by 2 inch) were treated with A3, and batches were progressively tested for exothermic response and cure time. Exothermic response was measured with a thermocouple datalogger while cure time was a hand measurement of the point at which maximum stiffness was achieved. FIGS. 23 and 24 display the exothermic and curing results obtained on accelerant treated specimens as well as the negative control values without accelerant.

The effectiveness of diethylol-p-toluidine was also evaluated in a cold environment. Reinforcement specimens (2 inch×2 inch) were held for 2 hours in a walk in freezer at −10° F. (+/−5 degrees), and then cure time was evaluated by hand in the cold environment. (Table 4)

TABLE 4

Cold environment cure time with varied amount of diethylol-p-toluidine

| Mass of diethylol-p-toluidine on reinforcement --> | 0 g | 0.006 g | 0.007 g | 0.009 g |
|---|---|---|---|---|
| Reinforcement | | | | |
| FG12 | 500 | 90 | 75 | 68.5 |
| FG6 | | 94 | 85 | 75 |
| FG8 | 240 | 121.5 | | 97.5 |
| FG7 | | 150 | 125 | 115 |
| FG9 | | 186.5 | 127.5 | 107.5 |
| FG9 | | 90.5 | | |
| FG11 | | 185 | 142.5 | 122.5 |
| FG11 | | 122.5 | 82.5 | 72 |
| FG10 | 900 | 102 | | |

4. Fiber Reinforcement Testing

Several different fiberglass fabrics were evaluated with cyanoacrylate in regards to cure time and maximum cure temperature at hot, cold, and room temperature. Table 5 provides information about the reinforcement candidates. Table 6 contains cure time and temperature of various reinforcements combined with cyanoacrylate resin in hot, cold, and room temperature environments. All specimens were 2 inch by 2 inch and treated with diethylol-p-toluidine. Hot environment testing was conducted at 120° F. (+/−5 degrees), cold temperature was at −10° F. (+/−5 degrees), and room temperature was at 72° F. (+/−5 degrees).

Furthermore, combinations of different cyanoacrylate and reinforcement candidates were evaluated in terms of flexural strength per ASTM D790 Standard Test Methods for Flexural Properties of Unreinforced and Reinforced Plastics and Electrical Insulating Materials. Results are presented in Table 7.

TABLE 5

Fiber Reinforcement Candidates

| ID | Material | Weave | Warp Count | Fill Count | Weight (oz/sqyd) | Thickness |
|----|----------|-------|------------|------------|------------------|-----------|
| FG1 | fiberglass | 8-harness satin | 57 | 54 | 8.81 | 0.0087 |
| FG2 | fiberglass | 8-harness satin | 57 | 54 | 8.81 | 0.0087 |
| FG3 | fiberglass | 8-harness satin | 57 | 54 | 8.81 | 0.0087 |
| FG4 | fiberglass | stitched uni-tape | | | 19.32 | 0.0083 |
| FG5 | fiberglass | 4-harness satin | 49 | 30 | 8.69 | 0.0078 |
| FG6 | fiberglass | 8-harness satin | 54 | 48 | 16.08 | 0.0157 |
| FG7 | fiberglass | Plain Weave | 16 | 14 | 10 | 0.014 |
| FG8 | fiberglass | Plain Weave | 18 | 16 | 7.91 | |
| FG9 | fiberglass | Plain Weave | 28 | 17 | 11.2 | 0.013 |
| FG10 | fiberglass | Plain Weave | 31 | 16 | 12.5 | 0.015 |

TABLE 5-continued

Fiber Reinforcement Candidates

| ID | Material | Weave | Warp Count | Fill Count | Weight (oz/sqyd) | Thickness |
|---|---|---|---|---|---|---|
| FG11 | fiberglass | Plain Weave | 24 | 9 | 28.9 | 0.015 |
| FG12 | fiberglass | Plain Weave | 35 | 18 | 19 | 0.020 |
| FG13 | fiberglass | Mock Leno | 40 | 21 | 19.86 | 0.0248 |
| FG14 | fiberglass | 8-harness satin | 54 | 48 | 16.08 | 0.0157 |
| FG15 | fiberglass | Knit | | | | |
| FG16 | fiberglass | Knit | | | | |
| C1 | carbon | Non woven 24K tow | | | | |
| C2 | carbon | Non woven 12K tow | | | | |
| C3 | carbon | Non woven 12K tow | | | | |
| C4 | carbon | Non woven 12K tow | | | | |
| C5 | carbon | Plain Weave | | | | |
| C6 | carbon | stitched uni-tape | | | | |
| C7 | carbon | 5-harness satin | | | | |
| C8 | carbon | 5-harness satin | | | | |
| C9 | carbon | Plain Weave | 12 | 12 | 5.8 | |

TABLE 6

Evaluation of cure time and temperature of low viscosity cyanoacrylate on various reinforcements

| Reinforcement | # of plies | Volume of Resin (ml) | Peak temp during room temp cure (° F.)[1] Under foam | Peak temp during room temp cure (° F.)[1] Outside foam | Cold Cure Time (seconds)[2] | Room Temp Cure Time (seconds)[2] | Peak temp during elevated temp cure (° F.)[1] Under foam | Peak temp during elevated temp cure (° F.)[1] Outside foam | "Skin" temp on full scale dummy at room temp (° F.) |
|---|---|---|---|---|---|---|---|---|---|
| FG3 | 3 | 2 | 190.6 | 123 | | 25 | | | |
| FG6 | 2 | 1.2 | 178 | 108 | 89 | 45 | 200 | 142 | 145 |
| FG8 | 3 | 1.2 | 174 | 110 | 110 | 42 | 202 | 137 | |
| FG12 | 2 | | 258 | 138 | 90 | | | | |
| FG7 | 3 | 1.2 | 202 | 126 | 150 | 51 | | | |
| FG9 | 3 | 1.2 | 174 | 112 | 90.5 | 57 | 206 | 145 | 117 |
| FG11 | 3 | 1.8 | 161 | 114 | 122.5 | 69 | | | |
| FG10 | 2 | 1.2 | 152 | 102 | 62.6 | 62 | 205 | 144 | 130 |

[1] With foam insulation
[2] Without foam insulation

TABLE 7

Results for cyanoacrylate composite three point bend flexural testing (ASTM D790)

| Reinforcement | # of Plies | Resin | Accelerant | Max Load Avg Max Load (lbs.) | Max Load Std. Dev. | Max Load Coefficient of Variation (%) | Flexural Strength Avg Flexural Strength (Ksi) | Flexural Strength Std. Dev. | Flexural Strength Coefficient of Variation (%) | Modulus Avg Modulus (Msi) | Modulus Std. Dev. | Modulus Coefficient of Variation (%) |
|---|---|---|---|---|---|---|---|---|---|---|---|---|
| FG3 | 3 | CA 1 | None | 15.60 | 0.70 | 4.49 | 26.62 | 1.61 | 6.03 | 1.55 | 0.04 | 2.36 |
| FG5 | 3 | CA 1 | None | 22.45 | 2.58 | 11.49 | 47.80 | 5.10 | 10.68 | 2.60 | 0.11 | 4.25 |
| FG5 | 3 | CA 1 | A3 (2.1%) | 17.30 | 0.80 | 4.57 | 40.65 | 1.86 | 4.57 | 2.91 | 0.10 | 3.56 |
| FG5 | 3 | CA 1 | A3 (2.9%) | 16.81 | 1.39 | 8.24 | 39.31 | 1.67 | 4.24 | 2.86 | 0.12 | 4.28 |
| FG5 | 3 | CA 1 | A5 (1.8%) | 14.48 | 0.56 | 3.85 | 33.01 | 2.06 | 6.24 | 2.58 | 0.08 | 3.09 |
| FG5 | 3 | CA 2* | None | 17.11 | 0.83 | 4.82 | 37.18 | 1.55 | 4.17 | 2.38 | 0.08 | 3.31 |
| FG5 | 3 | CA 4 | None | 27.84 | 1.98 | 7.12 | 74.47 | 5.90 | 7.92 | 3.15 | 0.09 | 2.86 |
| FG5 | 3 | CA 5 | None | 24.93 | 1.55 | 6.23 | 57.22 | 3.16 | 5.51 | 2.48 | 0.12 | 4.99 |
| FG5 | 3 | CA 6 | None | 21.54 | 1.90 | 8.82 | 52.30 | 5.26 | 10.06 | 2.65 | 0.11 | 4.24 |
| FG5 | 3 | CA 7* | None | 26.50 | 1.65 | 6.22 | 58.69 | 3.78 | 6.45 | 2.40 | 0.10 | 4.34 |
| FG6 | 2 | CA 6 | None | 14.32 | 1.78 | 12.41 | 29.70 | 3.72 | 12.52 | 1.21 | 0.07 | 6.02 |
| FG8 | 2 | CA 6 | None | 16.96 | 2.71 | 15.97 | 36.53 | 7.99 | 21.88 | 1.55 | 0.11 | 7.26 |
| FG9 | 2 | CA 6 | None | 8.55 | 1.15 | 13.48 | 20.80 | 3.44 | 16.52 | 1.35 | 0.09 | 6.68 |
| FG10 | 2 | CA 6 | None | 23.19 | 1.17 | 5.05 | 68.34 | 4.38 | 6.41 | 2.43 | 0.16 | 6.60 |
| SAM Splint | N/A | N/A | N/A | 1.50 | 0.12 | 7.81 | 17.86 | 1.23 | 6.89 | 8.92 | 1.16 | 13.04 |

*Tested with a 0.25" roller rather than a 10 mm roller designated by the ASTM

5. Distribution Tube Materials

Figure 25:
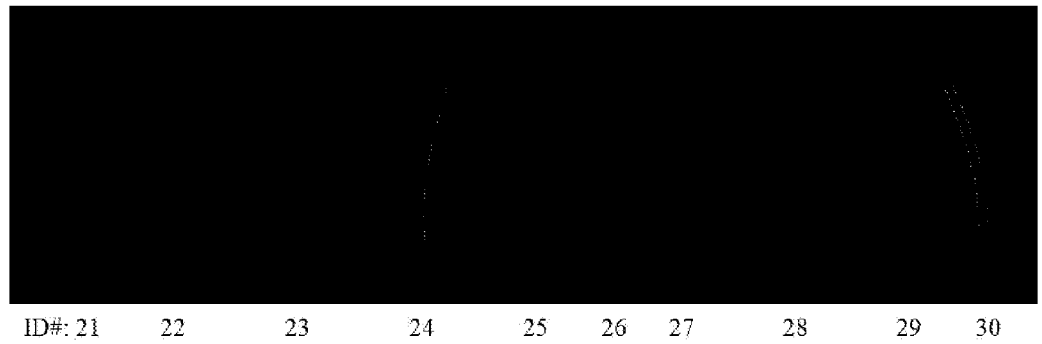
FIG. 25 is an image showing the radiolucency evaluation of various resin distribution tubes.

A variety of tube materials were evaluated for the resin distribution system. Table 8 shows the criteria used to down select the tubes. Scores were assigned to each criterion with 5 being the best performance and 0 being the worst. FIG. 25 shows one of the x-ray images used to evaluate the radiolucency of the tube candidates.

TABLE 8

Materials for the Resin Distribution Tube

| Material | ID | Ease of Bending | Resistance to Kinking | Radiolucency | Cyanoacrylate Compatibility | Ease of Drilling |
|---|---|---|---|---|---|---|
| Ethylene-propylene-diene monomer (EPDM) | 27 | 4 | 4 | 2 | 2 | 3 |
| Fluorinated ethylene propylene (FEP) | 11 | 0 | 5 | 2 | 5 | 5 |
| Polyethylene (PE) | 25 | 1 | 5 | 3 | 5 | 5 |
| Polytetrafluoroethylene (PTFE)-1 | 21 | 2 | 3 | 3 | 5 | 5 |
| Polytetrafluoroethylene (PTFE)-2 | 22 | 2 | 2 | 3 | 5 | 5 |
| Polyurethane (PU) -1 | 23 | 2 | 5 | 2 | 4 | 4 |
| Polyurethane (PU) -2 | 28 | 3 | 4 | 2 | 3 | 2 |
| Polyvinyl chloride (PVC)-1 | 24 | 3 | 2 | 0 | 1 | 4 |
| Polyvinyl chloride (PVC)-2 | 30 | 3 | 4 | 1 | 2 | 5 |
| Polyvinyl chloride (PVC)-3 | 12 | 4 | 5 | 1 | 0 | 3 |
| Silicon-1 | 26 | 4 | 4 | 1 | 4 | 3 |
| Silicon-2 | 29 | 5 | 1 | 4 | 4 | 1 |

6. Encapsulating Film/Foil

The encapsulating film encloses the reinforcement fabric and keeps the cyanoacrylate contained when it is injected into the fabric. Furthermore, it keeps the reinforcement isolated from dirt, moisture, oxygen, and light during storage and contains the odor produced by the cyanoacrylate during curing. Multiple film types have been investigated. Nylon film has good oxygen barrier properties and is transparent, which allows the distribution of the cyanoacrylate to be visible when it is injected into the fabric. Polyethylene film has good moisture barrier properties and is also transparent. A metalized multi layered film combines a foil and one or more plastic layers, giving it very good moisture, oxygen, and light barrier properties and allowing it to be heat sealed.

7. Insulating Barrier

Figure 26:
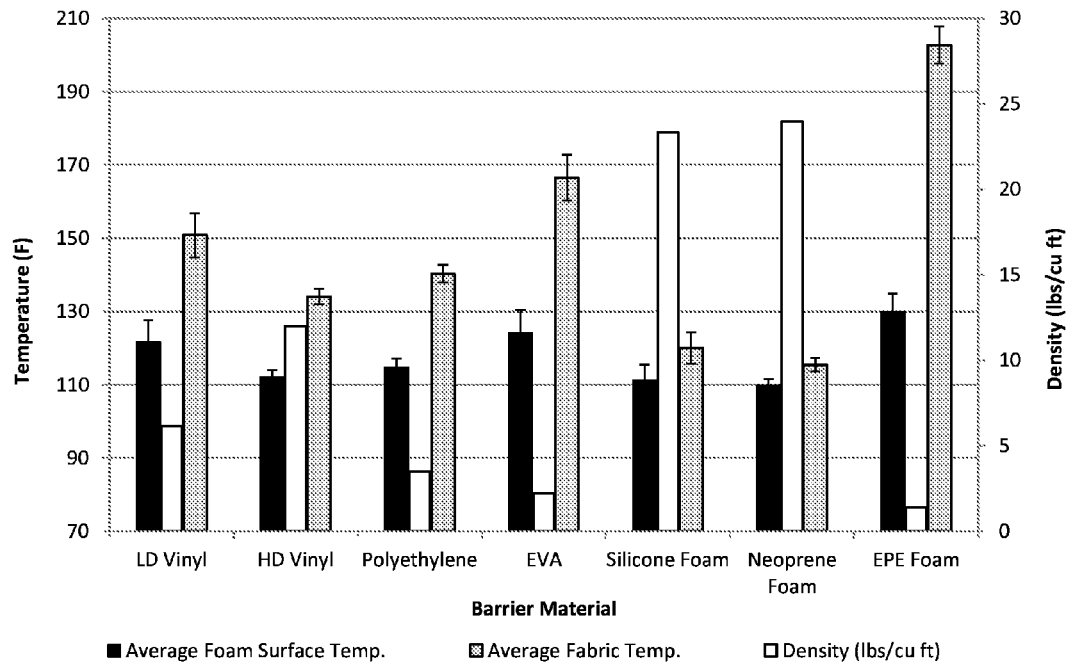
FIG. 26 is a graph of the evaluation of various insulating materials.

The insulating barrier isolates the exothermic reaction during curing and provides a soft cushion where the splint contacts the skin. In addition to having good insulating properties, the barrier also needs to be flexible, lightweight, thin, and acceptable for contact with the patent. To evaluate various materials for the insulating barrier, reinforcement specimens, 2 inch by 2 inch, were lined on either side with encapsulating film and barrier candidates. Temperatures were monitored on the outside surface of the insulating barrier and between the encapsulating film and the insulating barrier. These temperatures are denoted as outer and inner temperatures in Table 9. After small scale thermal trials, the list was narrowed down to seven top picks. Multiple thermal trials were run with these, and the results are shown in FIG. 26.

TABLE 9

Foams and rubbers considered for the insulating barrier

| Material | Outer Temperature (° F.) | Inner Temperature (° F.) | Density (lbs./cu ft) | Thickness (inch) |
|---|---|---|---|---|
| Buna-N | 112 | 128 | 10 | 0.15 |
| Ceramic Tape - thick | 137 | 165 | 12 | 0.06 |
| Ceramic Tape - thin | 136 | 160 | 12 | 0.03 |
| Espichlorohydrin (ECH) | 103 | 113 | 4 | 0.13 |
| Ethylene-propylene-diene monomer (EPDM)-1 | 94 | 99 | 30 | 0.11 |
| Ethylene-propylene-diene monomer (EPDM)-2 | 113 | 117 | 65 | 0.06 |
| Expanded Polyethylene (EPE) Foam - thick | 108 | 153 | 1 | 0.25 |
| Expanded Polyethylene (EPE) Foam - thin | 108 | 150 | 1 | 0.15 |
| Ethylene vinyl acetate (EVA)-1 | 103 | 120 | 2 | 0.12 |
| Ethylene vinyl acetate (EVA)-2 | 124 | 159 | 2 | 0.13 |
| Gum | 104 | 115 | 28 | 0.13 |
| Ionomer | 93 | 133 | 4 | 0.25 |
| Latex | 100 | 111 | 60 | 0.08 |
| Neoprene | 104 | 110 | 2 | 0.11 |
| Neoprene/EPDM/ Styrene-butadiene rubber (SBR) | 113 | 132 | 7 | 0.13 |
| Neoprene/Vinyl/Buna-N | 112 | 140 | 7 | 0.14 |
| Polyethylene (PE) | 118 | 146 | 3 | 0.13 |
| Polyethylene (PE)- open cell | 106 | 149 | 2 | 0.25 |
| Polyimide | 106 | 135 | <1 | 0.20 |
| Polyurethane (PU)- thick | 89 | 149 | 3 | 0.45 |
| Polyurethane (PU)- thin | 112 | 134 | 3 | 0.15 |
| Pyrogel Foam | 113 | 182 | 10 | 0.13 |

TABLE 9-continued

Foams and rubbers considered for the insulating barrier

| Material | Outer Temperature (° F.) | Inner Temperature (° F.) | Density (lbs./cu ft) | Thickness (inch) |
|---|---|---|---|---|
| Santoprene | 105 | 119 | 60 | 0.06 |
| Silicone | 99 | 105 | 7 | 0.13 |
| Vinyl | 103 | 134 | 10 | 0.14 |
| Vinyl/Buna-N | 114 | 136 | 6 | 0.14 |
| Viton | 111 | 127 | 17 | 0.11 |

8. Tackifier

A tackifier was incorporated to help hold the plies of fiberglass together. By reducing gaps between the plies of reinforcement and reducing gaps between the resin distribution tube and the reinforcement, the ability for the resin to move or wick through the reinforcement is improved. 3M Super 77 spray works well. Many other types including pressure sensitive and heat activated will also work.

Example 3

Comparison of Cyanoacrylate Rapid Setting Splint and SAM Splint Full Scale Mechanical Properties Full scale specimens were fabricated and formed with a 2" radius along their full lengths to simulate their form when applied to an injured limb. These 36" long specimens were cut in half so that two 18" test specimens were harvested from each product. Each specimen was tested in four point bending with matched lower curve supports with a support span of 14" and a loading span of 3". A displacement rate of 0.25 in/min was used and load and deflection data was collected at 10 Hz. Maximum load and stiffness data for each specimen were reported. (Table 10) The mechanical properties of the rapid setting composite splint can be tailored by changing the reinforcement.

TABLE 10

Four-Point Bend Test Results

| Test Specimen | Average Max Load [lb] | Std Error | Average Stiffness [lb/in] | Std Error |
|---|---|---|---|---|
| SAM Splint | 10.60 | 0.41 | 71.30 | 6.29 |
| 2 Ply Fiberglass | 13.50 | 1.06 | 32.20 | 1.71 |
| 2 Ply Carbon Plain Weave (PW) | 18.20 | 2.32 | 41.40 | 4.24 |
| 3 Ply Fiberglass | 26.90 | 4.34 | 64.50 | 7.97 |
| 3 Ply Carbon PW | 26.30 | 0.94 | 95.50 | 4.17 |
| 3 Ply Fiberglass/Carbon PW | 25.50 | 13.85 | 54.80 | 11.81 |
| 4 Ply Fiberglass | 25.90 | 1.53 | 117.40 | 6.00 |
| 4 Ply Carbon PW | 45.90 | 0.75 | 161.70 | 4.49 |
| 4 Ply Fiberglass/Carbon Uni-tape | 19.00 | 1.37 | 99.10 | 10.01 |

TABLE 10-continued

Four-Point Bend Test Results

| Test Specimen | Average Max Load [lb] | Std Error | Average Stiffness [lb/in] | Std Error |
|---|---|---|---|---|
| 4 Ply Fiberglass/Carbon PW | 47.40 | 8.56 | 80.00 | 1.76 |
| 5 Ply Fiberglass | 49.90 | 1.70 | 186.10 | 4.65 |
| 5 Ply Carbon PW | 72.10 | 2.86 | 193.70 | 24.04 |

Example 4

Air Catalyzed Polymerization

With air catalyzed polymerization, the stabilization device would be a composite of a reinforcement fabric pre-impregnated with an oxygen-sensitive resin ("prepreg"). The device would be packaged to isolate the prepreg from oxygen until the time of use. When the package is opened for use or air is injected into the package, the oxygen in air initiates the polymerization of the resin, which transforms the moldable prepreg into a strong stiff form for stabilization.

Known air-activated resins provided the starting point for developing a composition suitable for use in the invention. The chemistry generally involves oxygen in air reacting with an activator compound to form a hydroperoxide which is subsequently decomposed by a metal salt forming free radicals. These free radicals initiate the polymerization of ethylenically unsaturated monomers. The oxidation of the activator is facilitated by the use of an acid that is neither too weak nor too strong. Shelf life can be extended through the use of free radical stabilizers. The mixture generally includes a polymerizable monomer, oxidizeable activator, acid, a soluble metal salt, and a stabilizer.

1. Beta Diketone System

A known system involves the use of beta diketones such as methyl 2-oxocyclopentanecarboxylate (MOC) (see U.S. Pat. No. 6,552,140, incorporated by reference herein). One specific patent example uses, 0.1 g MOC, 0.5 g methacrylic acid, 8.4 g hydroxypropylmethacrylate, and 0.7 g 8% cobalt naphthenate in mineral oil. This mixture, when prepared in air, polymerized to a solid in 5 minutes.

Table 11 below shows the various components that were evaluated in the current invention.

TABLE 11

Ingredients for Beta Diketone System

| Polymerizable Monomer | Metal Salt | Weak acid | Activator (beta diketone) | Stabilizer | Co-activator |
|---|---|---|---|---|---|
| Hydroxypropyl-methacrylate | 6% Cobalt (II) naphthenate in | Methacrylic acid | Methyl 2-oxocyclo- | 4-amino-2,2,6,6 tetramethyl-1- | N,N-dimethylaniline |

TABLE 11-continued

Ingredients for Beta Diketone System

| Polymerizable Monomer | Metal Salt | Weak acid | Activator (beta diketone) | Stabilizer | Co-activator |
|---|---|---|---|---|---|
| (HPMA) | mineral oil (CoNAP) | (MAA) | pentane carboxylate (MOC) | piperidinyloxy (amino-TEMPO) | (DMA) |
| Ehthylene glycol dimethacrylate (EGD) Methyl-methacrylate (MMA) | Cobalt (II) acetylacetonate (CoAcAc) | | 2-methyl-1,3-cyclo-hexanedione (CHD) 2,2-dimethyl-1,3 dioxane-4,6-dione 3-methyl-2,4-pentadione 2-methyl-1,3-cyclo-pentanedione 2-acetyl-1,3-cyclo-hexanedione | | 4,N,N trimethylaniline (TMA) |

As mentioned above, free radical stabilizers can be used to increase shelf life. For example, 4-amino-2,2,6,6 tetramethyl-1-piperidinyloxy (amino-TEMPO) has been shown in the above patent to result in retention of air reactivity in the following formulation after 4 months of storage away from air at room temperature: 9.35 g polyethyleneglycol dimethacrylate, 0.3 g methacrylic acid, 0.1 g 8% Cobalt naphthenate in mineral oil, 0.25 g MOC, and 0.001 g amino TEMPO.

The solid CoAcAc was found to dissolve better in the mix than CoNAP. Of the many different beta diketones, MOC is liquid and soluble, which made it the easiest to use. However the MOC had some hydroperoxide contaminant already present which limits shelf life. It was also found that the MAA self-initiates polymerization when oxygen is removed as the typical quinone-based stabilizer needs oxygen to work. The di-functional monomer EGD was found to be much faster than the monomeric HPMA and MMA. With the beta diketone system, MAA only was evaluated as the acid component.

A preferred formulation developed through testing includes: 0.0520 g CoAcAc, 12.4 mL EGD, 4.0 mL MAA, 4.6 mL MOC "bulk", and 0.4 mL DMA. For the "bulk", a ratio of about 0.13 g CoAcAc for every 10 mL MOC was used. This was to react out the MOC hydroperoxide with cobalt. MOC was used as is from the supplier, hydroperoxide free MOC would eliminate the need for the "bulk" mix. The formulation was used to create composite prepreg specimens (2 inch by 2 inch). It is noted that the air-catalyzed composite splint could include a tube described above. However, instead of delivering the resin, it could be used to deliver air, or any gas containing oxygen, to the prepreg to further facilitate curing. The delivery tube could also be omitted from this embodiment. When this prepreg cures, this composite had an average peak temperature of 108° F. and an average time to peak temperature of 123 seconds.

2. Experimental Protocol for Beta Diketone System

Resin ingredients were sparged with nitrogen to remove oxygen and moved to a glove box with a nitrogen atmosphere. In the low oxygen environment, the following were combined 0.052 g CoAcAc, 12.4 mL EGD, 4.0 mL MAA, 4.6 mL MOC "bulk", and 0.4 mL DMA in a 50 mL plastic vial with a lid. The vial was shaken vigorously to homogenize the mixture. Next, fiberglass fabric strips (FG13, 2 plies; 3"×12") were introduced into the box along with nylon bags. Two plies were put into the bag and heat sealed shut. Using a needle and syringe, 13.5 mL of resin was withdrawn from the vial and injected into a nylon bag containing the two plies of fiberglass. The resin was spread out until it fully wetted the reinforcement. The nylon bag was then passed into atmospheric conditions. Thermocouple probes were taped to cardboard, and then the specimen was placed on top of the probes with pressure rubber points lined up over the probes and a weight set on top. Next, 60 mL of air was injected into the bag and the data logger was started. Data was collected through the peak temperature was reached and until temperature readings were below 90° F. The average of four peak temperatures was 112° F. and the average time to peak temperature was 185 seconds.

3. Tertiary Aromatic Amine System

Other air-catalyzed resins using aromatic tertiary amines such as 4,N,N-trimethylanaline as the activator were also evaluated. A formula from U.S. Pat. No. 5,354,821 containing 5% acetic acid, 5% N,N-dimethyl-p-toluidine, 0.5% of a 6% cobalt naphthenate solution in gasoline, and the dimethacrylate of bis phenol A X 2EO was evaluated. The pot life was 1 minute when mixed in air. Table 12 below shows additional ingredients evaluated for use in the current invention.

TABLE 12

Ingredients for Aromatic Tertiary Amine System

| Polymerizable Monomer | Metal Salt | Weak Acid and pKA | Activator | Stabilizer |
|---|---|---|---|---|
| Ethylene glycol dimethacrylate (EGD) | Cobalt (II) naphthenate in mineral oil (CoNAP) | Methacrylic acid (MAA) 4.66 | 4,N,N-trimethylaniline (TMA) | 4-hydroxy-2,2,6,6 tetramethyl-1-piperidinyloxy (OH-TEMPO) |
| Methylmethacrylate (MMA) | Cobalt (II) acetylacetonate (CoAcAc) | Acetic acid (AA) 4.76 | | 2,2,6,6-tetramethyl-1-piperidinyloxy (TEMPO) |
| Diethyleneglycol-diacrylate (DGD) | | Monochloroacetic acid (MCA) 2.85 | | Phenothiazine (PTZ) |
| Hydroxypropyl-methacrylate (HPMA) | | Dichloroacetic acid (DCA) 1.48 | | Methyl hydroxybenzoate (MHB) |
| Diacrylate of bis phenol A ethoxylate X 2EO (BISADA) | | Methane sulfonic acid (MSA) −2.0 | | |
| Dimethacrylate of bis phenol A ethoxylate X15EO (BISA) | | Formic acid (FA) 3.75 | | |
| Styrene | Isobutyric acid (IBA) 4.84 | | | |
| Divinylbenzene (DVB) | 4-picoline 6.02 (4P) | | | |
| Di-trimethylolpropane tetraacrylate (SR355) | | Acetylacetone 4.76 (AcA) | | |
| Polyester diacrylate (SR606A) | | | | |

In this work, a range of acid strengths was explored, and it was determined that DCA was the fastest, but with a compromise in composite stiffness. Acetic acid was slower, but gave higher composite stiffness. As with the beta diketone systems, the EGD was found to be faster than monofunctional monomers, but also acrylate monomers were substantially faster than methacrylate monomers but were less stiff. Ingredient ratios were optimized for fastest time to peak temperature.

4. Experimental Protocol Aromatic Tertiary Amine System a. Neat Resin Trials

Into a 16 mL glass vial, 0.0267 g of CoAcAc or 0.1 mL 6% CoNap in mineral oil was measured, followed by adding 7.2 mL of monomer, and then acid (amounts vary with different acids). The vial was capped and shaken vigorously for 30 seconds. The vials were allowed to sit for at least one hour to see if the chemicals separated. Next, 0.4 mL of TMA was injected into the vial, and the data logger was started. The vial was capped and shaken for 2 seconds. The vial was then uncapped and the datalogger probe was inserted into neat resin. Data was collected on the entire temperature profile of neat resin curing. The maximum temperature and time to maximum temperature were then determined.

b. Fabric Trials

Liquid chemicals were sparged and dry chemicals were vacuumed prior to being transferred into a low oxygen environment. In a low oxygen environment, the same formulations used for the neat resin trials were prepared and then injected into an 8 mL vial. Next, 7 mL of resin was measured out using a syringe and injected onto a strip of 6"×3" fabric sealed in a bag. The bag was passed into atmosphere conditions, and injected with 10 mL of oxygen. The datalogger was started immediately. The oxygen was distributed around the fabric, which was then laid flat and fitted with four thermocouple probes equidistance apart. Data was collected on the entire temperature profile. The average time to maximum temperature, average maximum temperature, and time to gel for remainder of the mix in the vial were then determined.

5. Aromatic Tertiary Amine System Experimental Summary

Figure 27:
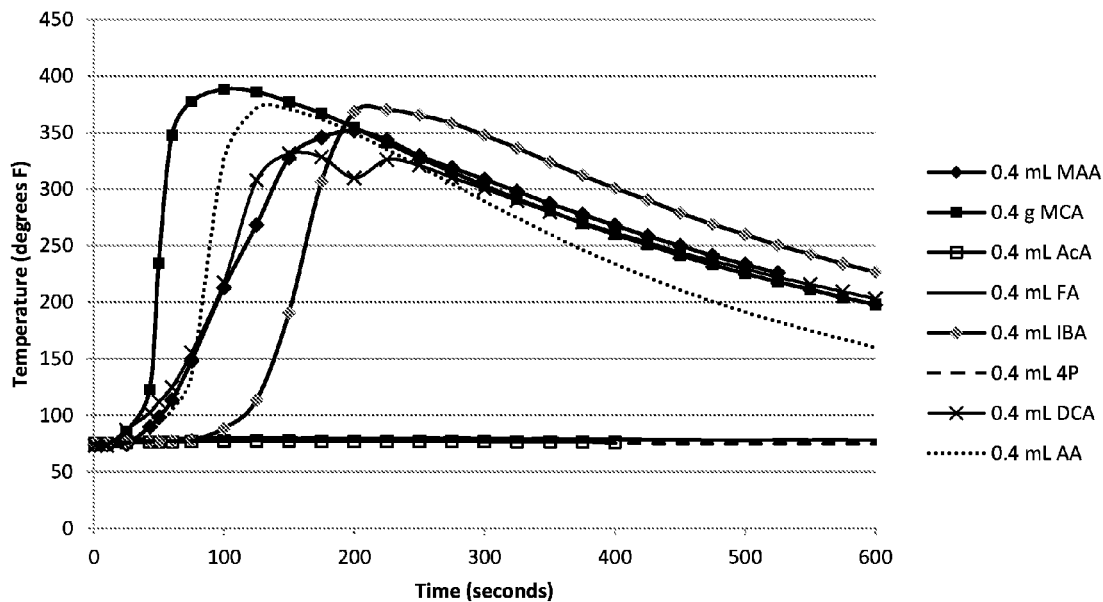
FIG. 27 is a graph of the different temperature profiles of various acids tested in Example 4.
Figure 28:
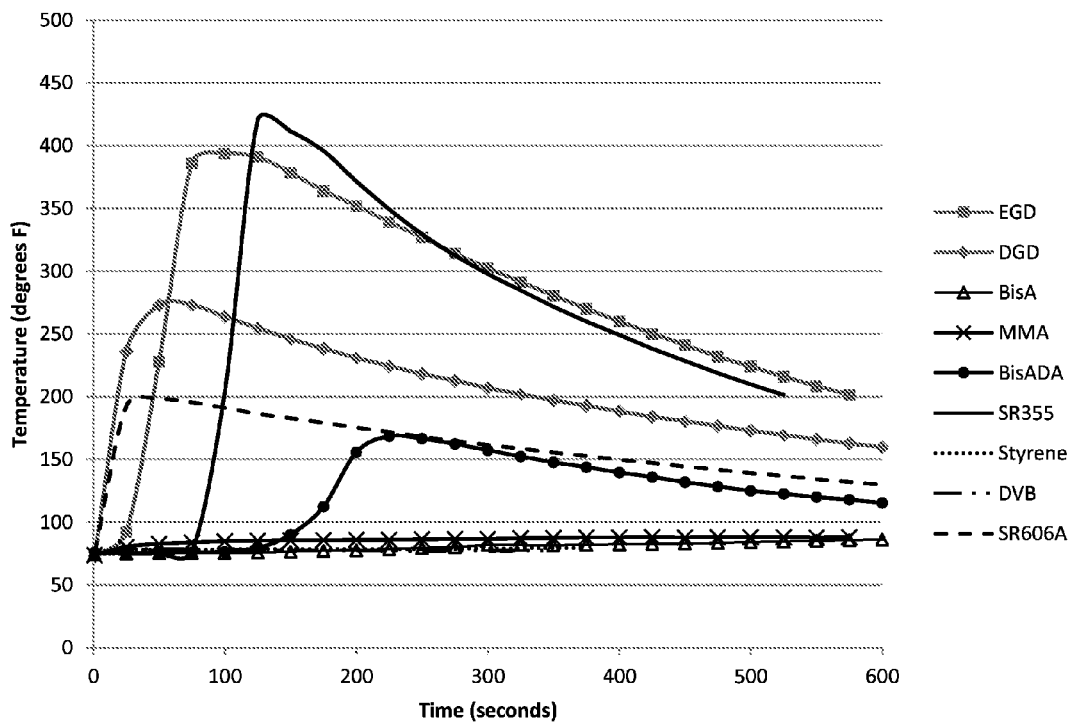
FIG. 28 is a graph of the different temperature profiles of the various monomers tested in Example 4.
Figure 29:
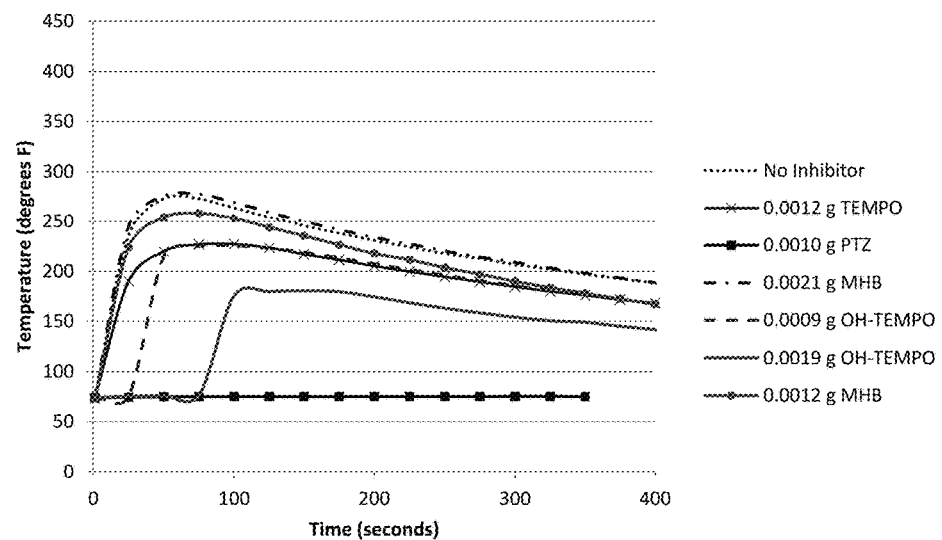
FIG. 29 is a graph of the different temperature profiles of the various inhibitors tested Example 4.

The effect of acid strength in various acids was evaluated with neat resin trials. Each of the various acids was combined with EGD, CoAcAc, and TMA. (FIG. 27) Reaction rate can be varied by the selection of the type and amount of acid. Use of various monomers was also evaluated with neat resin trials. Each of the various monomers was combined with CoAcAc, DCA, and TMA. (FIG. 28) Stabilizers, which slow down the reaction time of a free radical polymerization, were evaluated with neat resin trials. Stabilizers are incorporated for the purpose of increasing shelf life. Table 13 summarizes the various stabilizers and the amounts that were used. The choice of a stabilizer and amount can be tailored to keep reaction with air fast, but provide extended shelf life. Each of the various stabilizers was combined with DGD, CoAcAc, DCA, and TMA. (FIG. 29) Different reinforcements were also evaluated to see how they affect curing of the air-catalyzed resin. Reinforcements were prepared and tested as described in the Fabric Trials section, and results are shown in Table 14. Furthermore, air-catalyzed cured composites were evaluated in terms of flexural strength per ASTM D790 Standard Test Methods for Flexural Properties of Unreinforced and Reinforced Plastics and Electrical Insulating Materials. Results are presented in Table 15 and the resin recipes used for the test specimens are detailed in Table 16.

TABLE 13

Air-catalyzed resin stabilizers

| Stabilizers | Amount |
|---|---|
| Phenothiazine (PTZ) | 0.0010 g |
| TEMPO | 0.0015 g |
| OH-TEMPO | 0.0010 g |
| | 0.0020 g |
| | 0.0025 g |
| Methyl p-hydroxybenzoate (MHB) | 0.0010 g |
| | 0.0020 g |
| Tributyl Phosphite (TBP) | 1% solution |
| | 1 drop per 5 mL monomer |
| | 1 drop per 12 mL monomer |

TABLE 14

Fabric trials with air-catalyzed resin

| Reinforcement | Resin Volume (mL) | Cured Thickness (mm) | Max Temp (° F.) | Time to Max (seconds) |
|---|---|---|---|---|
| FG8 | 7.0 | 1.4 | 101 | 173 |
| FG5 | 7.0 | 1.2 | 96 | 188 |
| FG6 | 8.0 | 2.4 | 129 | 130 |
| FG14 | 8.5 | 2.3 | 115 | 189 |
| FG13 | 7.0 | 2.3 | 110 | 176 |
| FG3 | 7.0 | 1.2 | 103 | 167 |
| FG2 | 7.0 | 1.4 | 109 | 168 |
| FG1 | 7.0 | 1.3 | 104 | 145 |
| FG10 | 8.0 | 1.7 | 109 | 145 |
| FG15 | 11.0 | 3.0 | 164 | 92 |
| FG16 | 10.0 | 2.8 | 153 | 123 |
| C5 | 7.0 | 1.5 | 109 | 127 |
| C9 | 7.0 | 1.2 | 101 | 175 |
| C6 | 7.0 | 1.4 | 101 | 123 |

Example 5

Photo-Curable Resin

The following is an overview of the photo-cure composite splint. The first topic covered is the construction of the splint. This is included to provide an understanding of how the individual components of the product come together. This is followed by a description of testing conducted with various light sources.

1. Photo-Cure Splint Construction

Example components of a photo-catalyzed resin based splint are listed in Table 17.

TABLE 17

Components of a Photo resin based splint

| Component | | Size/Amount per Splint |
|---|---|---|
| Resin | Photo cure resin Rapid Cure Technologies RCT 01 1065 UV | 64 ml |
| Reinforcement fiber | Woven and/or unidirectional fiberglass fabric | 6 plies, each 3" × 36" |
| Encapsulating film | Heat sealable poly film - polyethylene or nylon | 2 sheets, each 4" × 38" Or 38" of 3" wide lay-flat tube |
| Insulating barrier | Polyethylene foam with adhesive backing | 2 pieces, each 3.5" × 36.5" |
| Light source | Flexible LED strip - blue or UV light | 2 strips, each 3 ft long |
| Power source | 9 V battery | 2 |
| Switch | Slide switch | 1 |
| Spacer | Bubble wrap | 2 plies, each 3" × 36" |
| Reflector | Mylar film | 2 plies, each 3" × 36" |

The following describes how photo-cure splint prototypes have been constructed.

1. Made the resin impregnated reinforcement compartment or prepreg compartment.

TABLE 15

Results for air-catalyzed composite three point bend flexural testing (ASTM D790)

| | | | Max Load | | | Flexural Strength | | | Modulus | | |
|---|---|---|---|---|---|---|---|---|---|---|---|
| Reinforcement | Number of Plies | Resin | Avg Max Load (lbs.) | Standard Deviation | Coefficient of Variation (%) | Avg Flexural Strength (Ksi) | Standard Deviation | Coefficient of Variation (%) | Avg Modulus (Msi) | Standard Deviation | Coefficient of Variation (%) |
| SAM Splint | N/A | N/A | 1.50 | 0.12 | 7.81 | 17.86 | 1.23 | 6.89 | 8.92 | 1.16 | 13.04 |
| FG3 | 3 | Autox 1 | 16.65 | 3.35 | 20.11 | 43.40 | 5.21 | 12.01 | 2.48 | 0.12 | 4.97 |
| FG3 | 3 | Autox 2 | 20.05 | 1.98 | 9.89 | 52.28 | 2.22 | 4.25 | 2.39 | 0.12 | 5.09 |
| FG13 | 2 | Autox 3 | 7.54 | 0.42 | 5.58 | 13.20 | 0.97 | 7.38 | 0.82 | 0.10 | 12.55 |

TABLE 16

Air-catalyzed resins for flexural testing

| Resin | HPMA | EGD | CoAcAc | MAA | MOC | CHD | TMA |
|---|---|---|---|---|---|---|---|
| Autox 1 | 12.4 ml | 4 ml | 0.023 g | 1 ml | 0.7 ml | — | — |
| Autox 2 | 12.4 ml | 4 ml | 0.023 g | 1 ml | — | 0.15 g | — |
| Autox 3 | — | 13.5 ml | 0.0525 g | 0.75 ml | — | — | 0.75 ml | a. The measured volume of resin was distributed on the pre-cut fiberglass fabric.
b. The fiberglass and resin were placed in a poly film bag and the openings were heat sealed.
c. A roller or scraper was used to spread the resin until it was evenly distributed on the fiberglass prepreg. The prepreg compartment was then set aside.
2. Assembled the flexible LED strips, batteries, and switch.
   a. The two flexible LED strips were placed parallel to each other approximately 1.5" apart.
   b. The strips were wired together in series.
   c. At one end of the LED strips, the switch and two 9V batteries were attached.
   d. The assembled unit (flexible LED strips, batteries, and switch) was set aside.
3. Assembled the reflector and insulating barrier.
   a. Each of the reflectors were centered and then applied to the adhesive side of the insulating barrier. The reflectors were smaller than the insulating barrier such that a 0.25" edge of adhesive remained exposed.
4. Using the adhesive backing on the flexible LED strips, the LED strips were attached to one of the two reflectors at a location 0.75" from the midline of the reflector and centered lengthwise.
5. The spacers were centered and placed on top of the lights.
6. The prepreg compartment was centered and placed on top of the spacers.
7. The remaining reflector/insulating barrier were centered and placed on top of the prepreg compartment such that the reflector was adjacent the prepreg compartment.
8. The adhesive edges on the insulating barriers were pressed together to enclose the lights, battery, spacer, prepreg compartment, and reflectors. The switch remained accessible.
9. Depending on the evaluation, the package was placed either: (a) flat on a table top, (b) around a dummy limb (FIG. 17), or (c) curved on a 4" diameter cylinder. If testing required, thermocouple probes were placed on the outer surface of the insulating barrier (to test skin contact temperatures) and/or between the encapsulating film and insulating barrier (to get the composite's temperature profile during curing).
10. The switch was turned to the ON position. Within 110 seconds, the resin cured and the reinforcement compartment was a stiff and protective construct.

2. Photo-Cure Splint—Light Source and Resin Trials

The cure time of the photo-cure prepreg is dependent upon selected resin and the light source to which it is exposed. Table 18 provides cure times achieved with various light sources and resins. Tests were carried out on 6-ply fiberglass specimens with a resin content of 40% by weight. The specimens were 3"×3" in size and cured at room temperature. The position of the light sources varied. Top emitting LEDs were evenly distributed on top of the specimen. Side emitting LEDs were placed along the edge(s) of the specimen. Side emitting fiber optics and electroluminescent wires were evaluated in two positions: 1) evenly distributed on top of the specimen and 2) sandwiched within the prepreg, in between reinforcement plies. Electroluminescent panels were placed on the top and bottom sides of the specimens.

TABLE 18

Cure time of photo-cure prepreg when exposed to different light sources

| | Light Source | Resin | Cure Time |
|---|---|---|---|
| Top Emitting LEDs | 5050 SMD - Blue<br>2 strips - 30 LEDs per meter | RCT[1] | 2 minutes |
| | 3528 SMD - Blue<br>4 strips - 60 LEDs per meter | RCT[1] | 2.5 minutes |
| | 3528 SMD - Blue<br>7 strips - 60 LEDs per meter | RCT[1] | 0.7 minutes |
| | 3528 SMD - UV<br>7 strips - 60 LEDs per meter | RCT[1] | 0.8 minutes |
| | 3528 SMD - UV<br>7 strips - 60 LEDs per meter | SunRez[3] | 2 minutes |
| | 3528 SMD - UV<br>7 strips - 60 LEDs per meter | RBC[2] | 1.5 minutes |
| Side Emitting LEDs | 5 mm DIP - Blue<br>1 strip - 96 LEDs per meter | RCT[1] | 1.5 minutes |
| | 335 SMD - Blue<br>2 strips<br>60 LEDs per meter | RCT[1] | 2 minutes |
| Side emitting fiber optics | 3 mm acrylic strands with ultra bright blue LED | RCT[1] | Not cured after 10 minutes. |
| | 0.25 mm acrylic strands with ultra bright blue LED | RCT[1] | |
| Electroluminescent (EL) | 2 EL panels, one on each side of the prepreg | RCT[1] | 6 minutes |
| | 1 EL wire | RCT[1] | 5 minutes<br>Cured a 0.5" wide strip along the length of the wire |

[1]Rapid Cure Technologies (RCT 01 1065 UV)
[2]RBC Industries Inc. (RBCX-15-82-1)
[3]Sunrez Corporation (733984)

Example 6

Comparison of Photo-Cure Rapid Setting Splint and SAM Splint Full Scale Mechanical Properties Full scale specimens were fabricated and formed with a 2" radius along their full lengths to simulate their form when applied to an injured limb. These 36" long specimens were cut in half so that two 18" test specimens were harvested from each product. Each specimen was tested in four point bending with matched lower curve supports with a support span of 14" and a loading span of 3". A displacement rate of 0.25 in/min was used and load and deflection data were collected at 10 Hz. Maximum load and stiffness data for each specimen were reported. (Table 19) The mechanical properties of the rapid setting composite splint can be tailored by changing the reinforcement.

TABLE 19

Four-point bend test results for Photo-cure resin

| Test Specimen | Average Max Load [lb] | Std Error | Average Stiffness [lb/in] | Std Error |
|---|---|---|---|---|
| SAM Splint | 10.60 | 0.41 | 71.30 | 6.29 |
| 5 Ply Photo-cured fiberglass | 21.4 | 4.4 | 102.7 | 17.7 |
| 6 Ply Photo-cured fiberglass | 31.1 | 0.6 | 133.7 | 21.3 |
| 7 Ply Photo-cured fiberglass | 58.0 | 4.3 | 231.7 | 19.3 |

Example 7

Hot and Cold Environment Testing

Since these devices may be used in a variety of environments, testing was conducted to determine if the three resin systems would cure under a range of ambient temperatures. The following describes the evaluation of the composites' cure time under hot, cold, and room temperatures.

Test Setup

All specimens were placed onto a ⅛ inch thick silicon rubber mat to simulate contact with human skin. A timer was started when each composite was activated. The composites evaluated included a low viscosity cyanoacrylate on fiberglass (FG8), a light activated resin (RCT 01 1065 UV) on fiberglass (FG8), and an aromatic tertiary amine air catalyzed resin with fiberglass (FG15). A subjective hand measured stiffness scale, seen in Table 20, was established and used to gauge each specimen in fifteen second intervals beginning at the start of activation and continued until the specimen was fully cured. This process was used for cold (−10° F.), hot (120° F.), and room (72° F.) temperature testing. All specimens were allowed to acclimate for at least four hours in each environment before testing.

TABLE 20

Hand Measured Stiffness Scale
Feel Stiffness Scale

Figure 35:
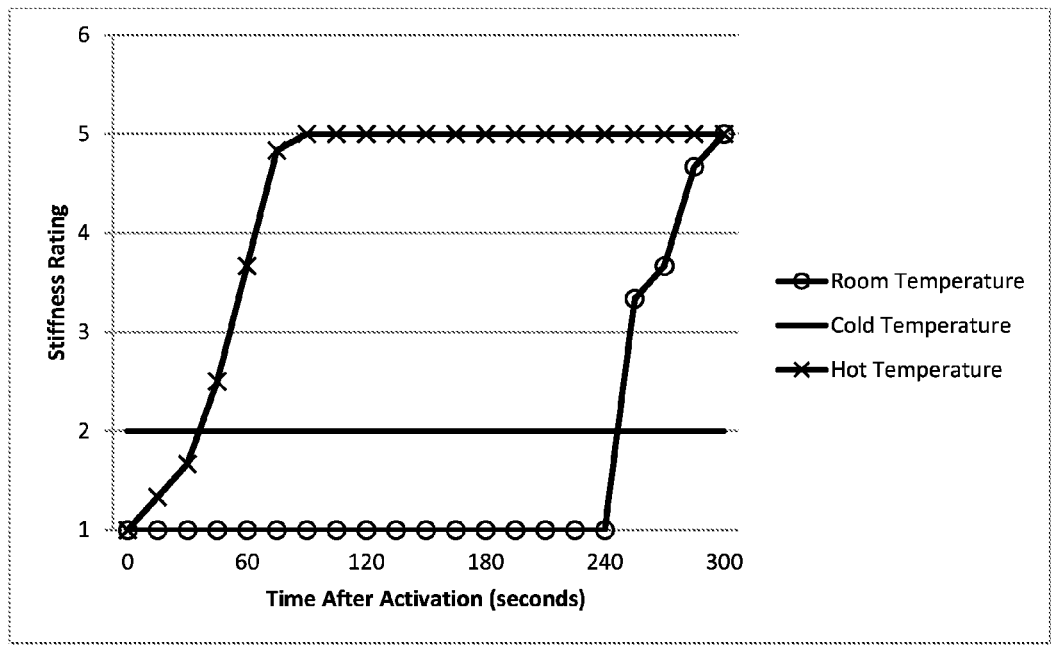
FIG. 35 is a graph of hand measured stiffness of the air catalyzed composite versus time.
Figure 36:
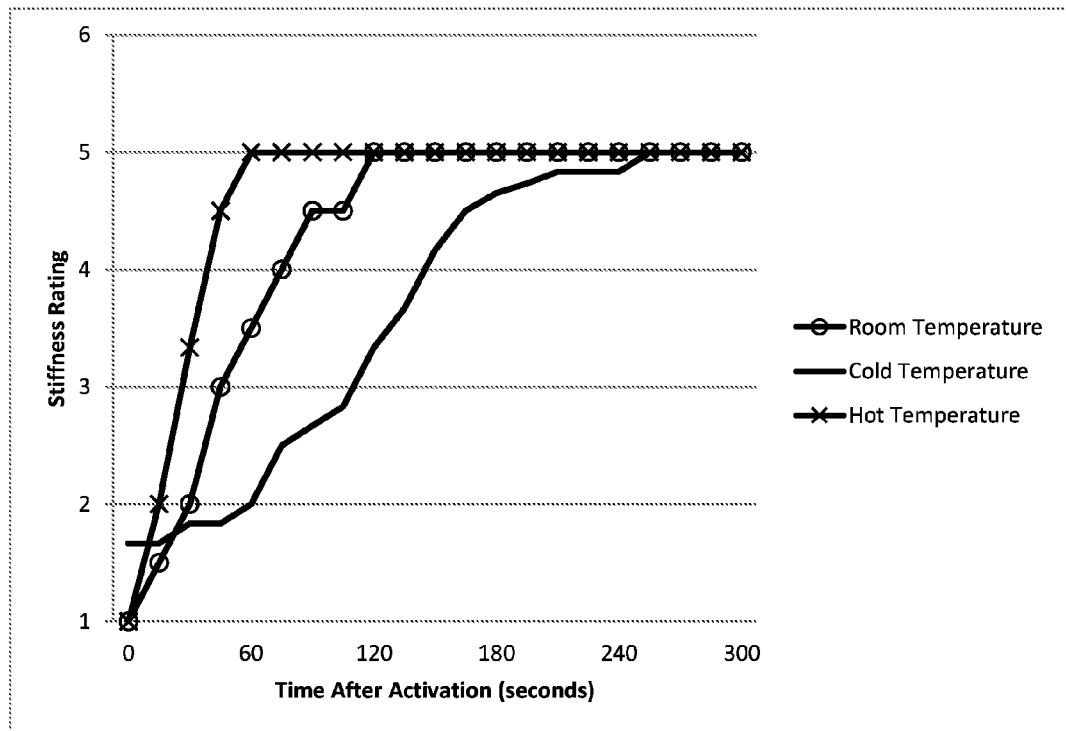
FIG. 36 is a graph of hand measured stiffness of the light activated composite versus time.
Figure 37:
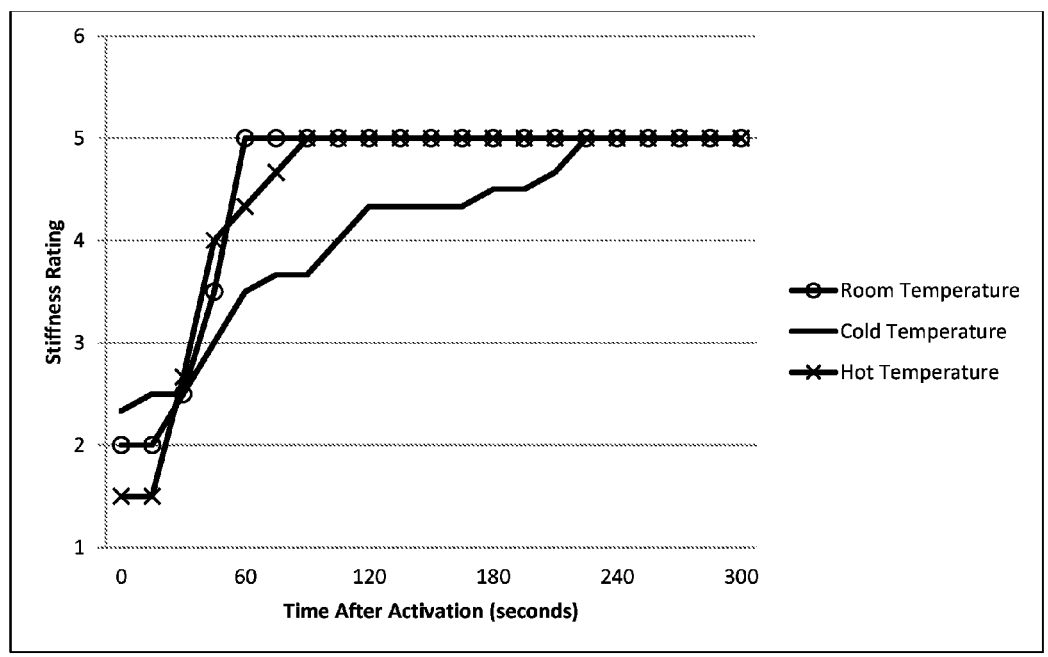
FIG. 37 is a graph of hand measured stiffness of the cyanoacrylate composite versus time.
Figure 38:
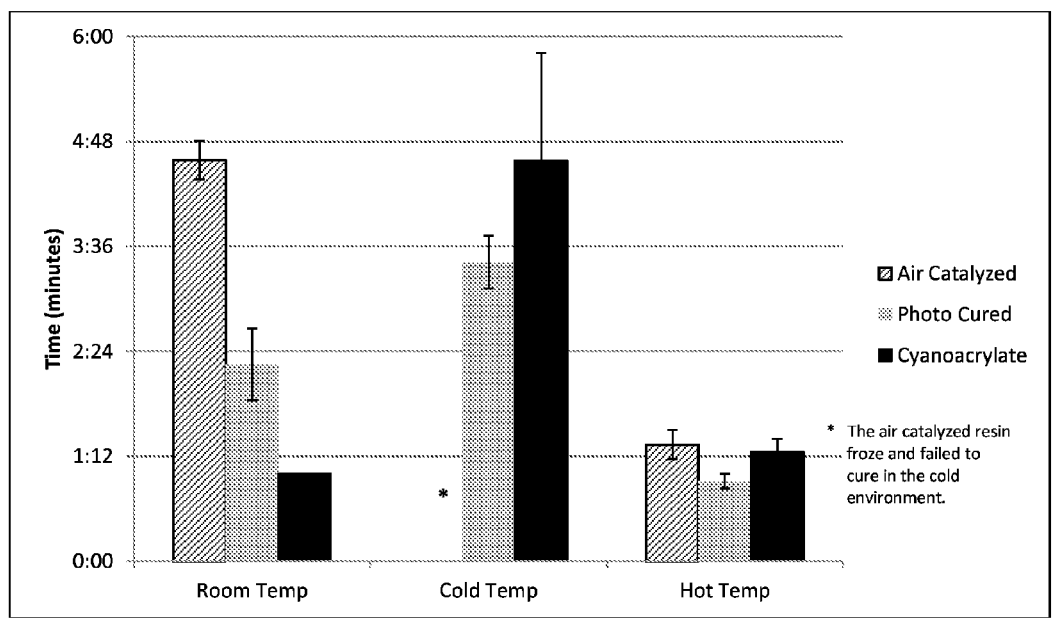
FIG. 38 is a graph of cure time based on hand measured stiffness of different resins at various temperatures.

1 No stiffness (paper)
2 Light to medium resistance (cardstock)
3 Medium stiffness (credit card)
4 Mostly stiff, slight bending
5 Extremely stiff, no bending Results Three specimens for each environment (room temperature, cold, and hot) for each resin were tested, for a total of nine specimens. Stiffness was measured by hand and used to determine the time it took for each specimen to cure. The averages of each composite in each environment were compiled and graphed against time in FIG. 35 for the air catalyzed resin, FIG. 36 for the light activated resin, and FIG. 37 for the cyanoacrylate. The time required to reach maximum stiffness is shown in FIG. 38. The cold temperature testing gave some variable results. The air catalyzed specimens never cured in the −10° F. environment; however, when moved to a warmer environment, room temperature, the specimens cured within thirty minutes. This is because the primary ingredient of the resin system, monomer EGD, has a freezing point of −4° F. As expected, each of the composites cured faster in the hot environment and slower in the cold environment.

Example 8

Hot Surface Skin Contact Testing

The three composites discussed all produce heat during curing, therefore testing was conducted in accordance with ASTM C1055 *Standard Guide for Heated System Surface Conditions that Produce Contact Burn Injuries* and ASTM C1057 *Standard Practice for Determination of Skin Contact Temperature from Heated Surfaces Using a Mathematical Model and Thermesthesiometer*. A thermesthesiometer was used for this testing to simulate the thermal response felt by a finger when placed against a heated surface. It has a temperature probe encased in silicone, which mimics the thermal conductivity of skin, and includes a heater to warm the silicone up to body temperature, 91.4° F.

Test Setup

A thermesthesiometer was constructed and calibrated in accordance with the thermesthesiometer engineering and construction manual. Per ASTM C 1055, testing was conducted at room temperature. Specimens were placed onto a ⅛ inch thick silicone rubber mat to simulate contact with human skin. After the thermesthesiometer was allowed to acclimate to 91.4° F. for at least fifteen minutes, it was placed in the center of the specimen. The composites evaluated included a low viscosity cyanoacrylate on fiberglass (FG8), a light activated resin (RCT 01 1065 UV) on fiberglass (FG8), and an aromatic tertiary amine air catalyzed resin with fiberglass (FG15). Three specimens were tested for each composite type (air catalyzed, light cured, and cyanoacrylate).

Results

Figure 39:
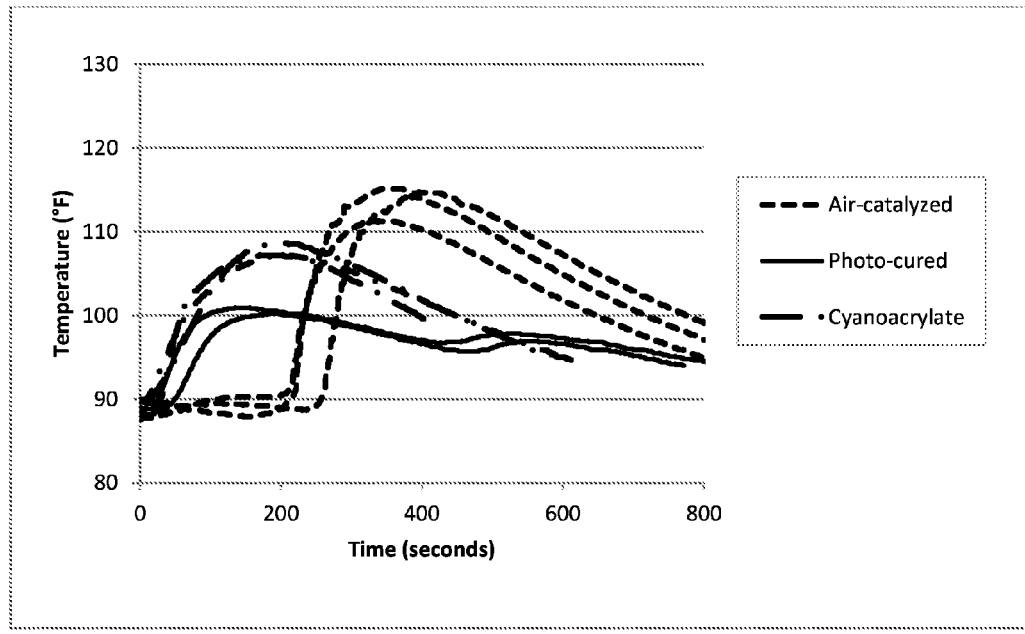
FIG. 39 is a graph of thermesthesiometer temperature measurement of composite curing using different resins.
Figure 40:
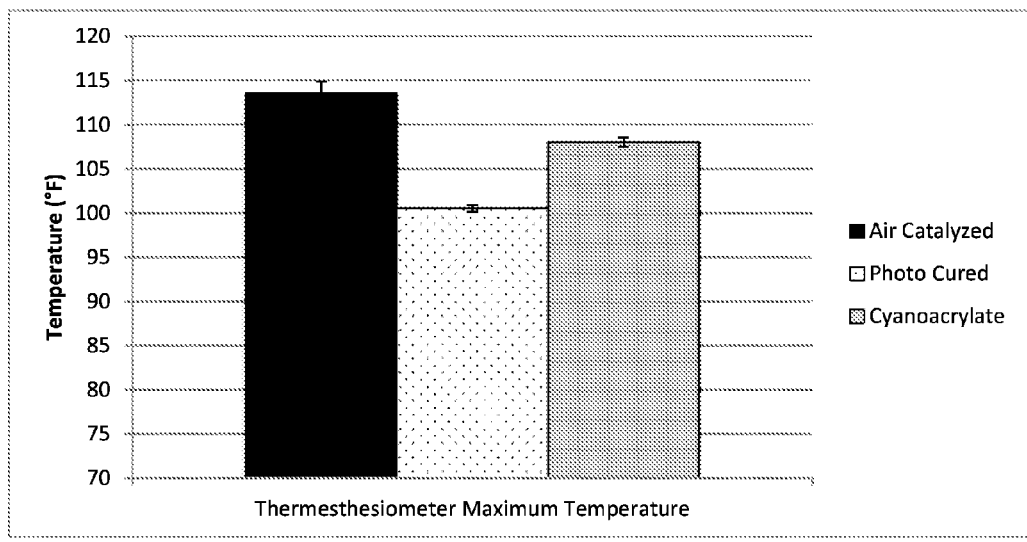
FIG. 40 is a graph of thermesthesiometer maximum temperature measurement of composite curing using different resins.
Figure 41:
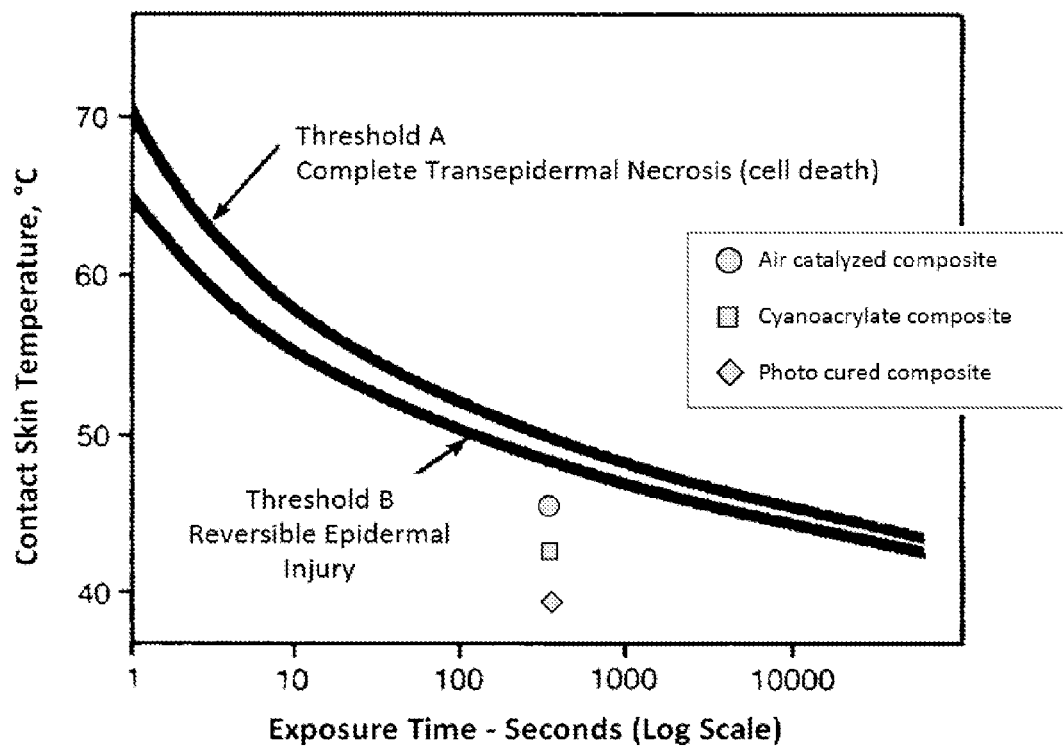
FIG. 41 is a graph of the thermesthesiometer maximum temperature measurement compared to the ASTM C 1055 burn chart.

Thermesthesiometer data for each of the replicates is plotted (see FIG. 39). FIG. 40 displays the average and standard error of the maximum temperature reached. The ASTM standard is established for steady state hot surfaces, but the temperature of the composites is continuously changing with time. The maximum temperatures reached by the composites are maintained for 1-2 seconds, and then the temperatures begin to drop. To evaluate the composites against the ASTM standard, worst case scenario was assumed. Rather than evaluating the maximum temperature for a few seconds, the maximum temperate was evaluated for the duration of the cure period, approximately 600 seconds. FIG. 41 shows that even when using the extended time period, all of the composites are in the safe region, below the epidermal injury curve.

Example 9

Preimpregnated Resin Distribution

Commercial prepregs have high viscosity resin to ensure even resin distribution regardless of the storage orientation.

Figure 42:
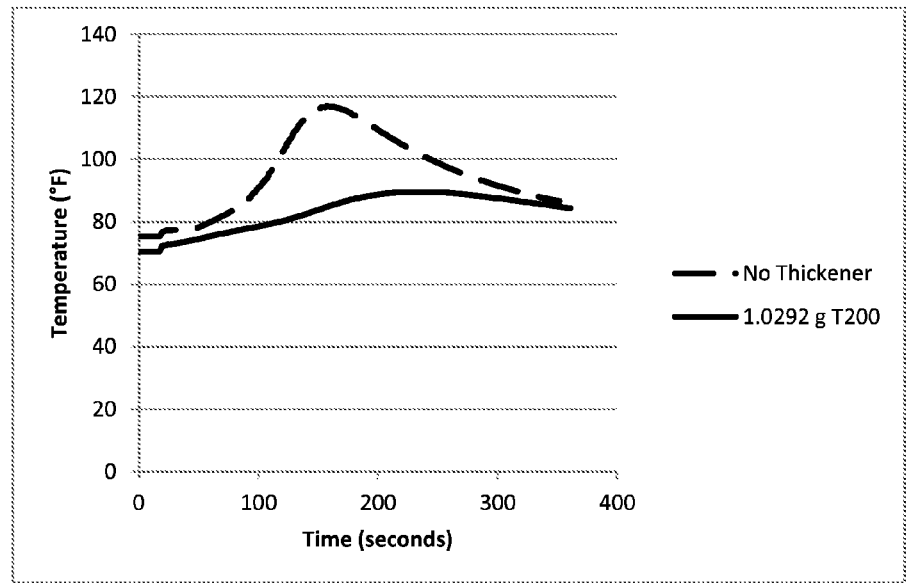
FIG. 42 is a graph of the temperature profiles during curing of air-catalyzed composite with and without Aqualon T200 thickener.
Figure 43:
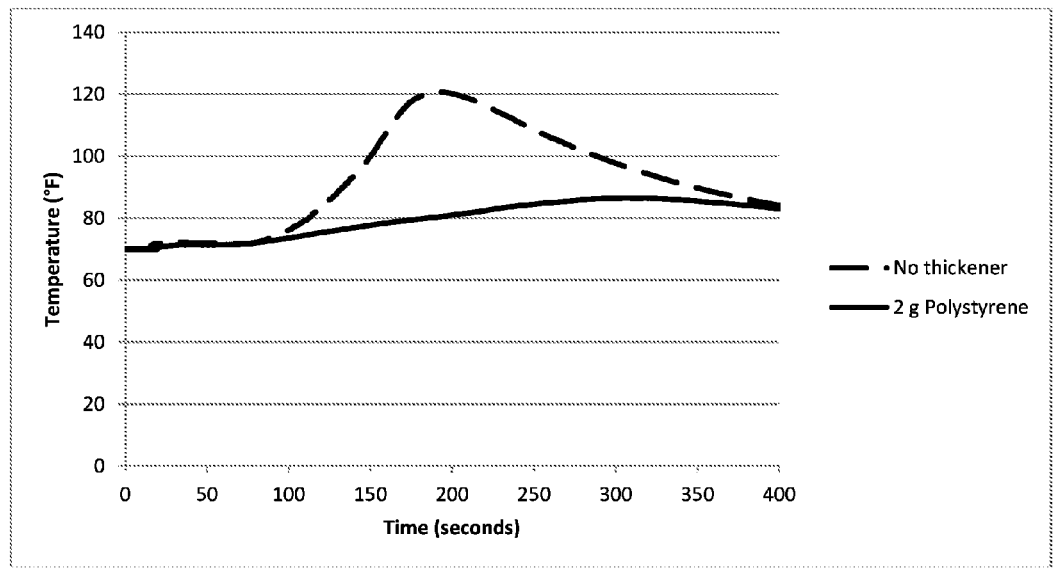
FIG. 43 is a graph of the temperature profiles during curing of air-catalyzed composite with and without polystyrene thickener.

Thickeners were investigated for the air-catalyzed resin to keep the resin in place and avoid pooling. In a preliminary screening, 1 gram of Aqualon T200, Aqualon T300, and Klucel M were each combined with 10 mL of EGD. The samples were stirred every 15 minutes. After 2 hours, Klucel M did not dissolve into the EGD, the Aqualon T300 increased the viscosity non-uniformly, and the Aqualon T200 increased the viscosity with slightly better uniformity. Polystyrene was also identified as an alternate thickening agent. The amounts and types of thickeners evaluated with 10 mL of EGD are listed in Table 21. From this preliminary screening, it was determined that Aqualon T200 and polystyrene should be tested with the air-catalyzed resin system on reinforcement. To achieve even resin distribution with minimal effort, the dry thickeners were applied to the reinforcement before impregnating the reinforcement with resin. With this method, the resin, in a low viscosity state, would be injected into the reinforcement package and easily wick to achieve even distribution throughout the reinforcement. Over time, the resin would increase in viscosity by dissolving the thickening agent on the reinforcement. The Aqualon T200 granules were placed onto the reinforcement and adhered using a hot press to melt the granules to the fabric in a uniform manner. The polystyrene was dissolved in toluene and then the solution was poured over the reinforcement. The toluene was allowed to evaporate, leaving the fabric coated with polystyrene. After coating the reinforcement with the thickeners, the reinforcements were transferred into a glove box and allowed to rest overnight in the low oxygen environment. The reinforcements were then impregnated with resin a manner similar to that described in sub-section 4b of Example 4. Thermal data during curing was recorded for both a specimen with thickener and without thickener. For the Aqualon T200 trial, the resin consisted of 0.0533 g CoAcAc, 14.4 mL EGD, 0.8 mL AA, and 0.8 mL TMA. Results are shown in FIG. 42. For the polystyrene trial, the resin consisted of 0.0045 g TEMPO, 0.0533 g CoAcAc, 14.4 mL EGD, 0.8 mL AA, and 0.8 mL TMA. Results are shown in FIG. 43. Both of these thickeners significantly retarded the cure rate of the air-catalyzed resin system. To avoid this reduction in cure time, an alternate solution was developed: vacuum sealing the prepreg package. Pulling a vacuum on the package applies enough pressure to the package contents to keep the resin in place. Trials were conducted with the package stored in the worst case orientation, hanging vertically, and the resin remained evenly distributed along the length of the 3 foot long reinforcement. This solution keeps the resin from moving and maintains the fast cure rate of the resin.

TABLE 21

Thickening Agents

| Thickeners | Amount |
|---|---|
| Aqualon T200 | 1.0 gram |
| Aqualon T300 | 1.0 gram |
| Klucel M | 1.0 gram |
| Polystyrene | 1.4 gram |
|  | 2.0 gram |

Example 10

Stabilizing the Air-Catalyzed Resin

If a composite is to be used in industry, it is important that it be shelf stable. In the case of the cyanoacrylate and light activated resin, the resins are available off the shelf and their shelf life is already established. This is not the case for the specially formulated autox resin, therefore various stabilizers were evaluated with the goal of achieving a 12 month shelf life. Preliminary testing of different amounts of stabilizers was discussed in Example 4 and summarized in Table 13. Based on results from that testing, an accelerated shelf life study was conducted using the amounts shown in Table 22. Each of the various amounts of stabilizers was combined with 14.4 mL EGD, 0.0533 g CoAcAc, 0.8 mL AA, and 0.8 mL TMA. The monomer, EGD, comes from the manufacturer with a stabilizer, MEHQ. To be effective, this stabilizer requires the presence of a small amount of oxygen. Unless noted otherwise, EGD was stripped of MEHQ.

As described in Example 4, the resin was prepared and distributed on the reinforcement in a glove box with a low oxygen environment. The prepreg package was sealed and then transferred out of the glove box into normal atmospheric conditions. To verify that the package had a good seal, specimens were checked to see if any had cured after one hour. After this check, the sealed specimens were transferred to an oven at 125° F. This warm environment accelerates the shelf life testing by four times the rate at room temperature, so one day in the oven simulates four days at room temperature.

Figure 44:
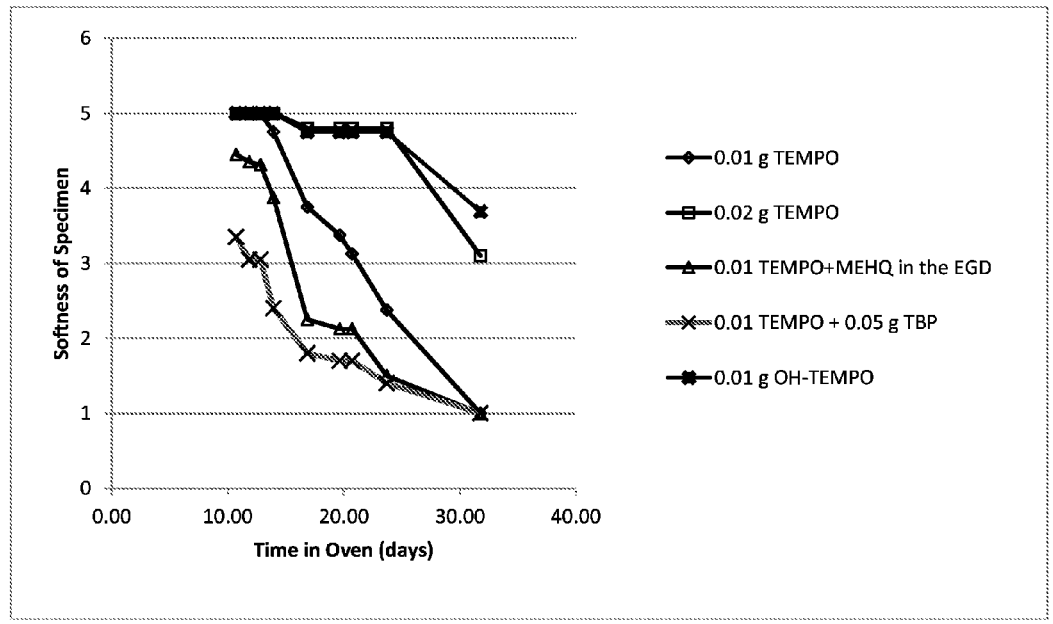
FIG. 44 is a graph of the hand evaluation of shelf life specimens held in 125° F. oven.
Figure 45:
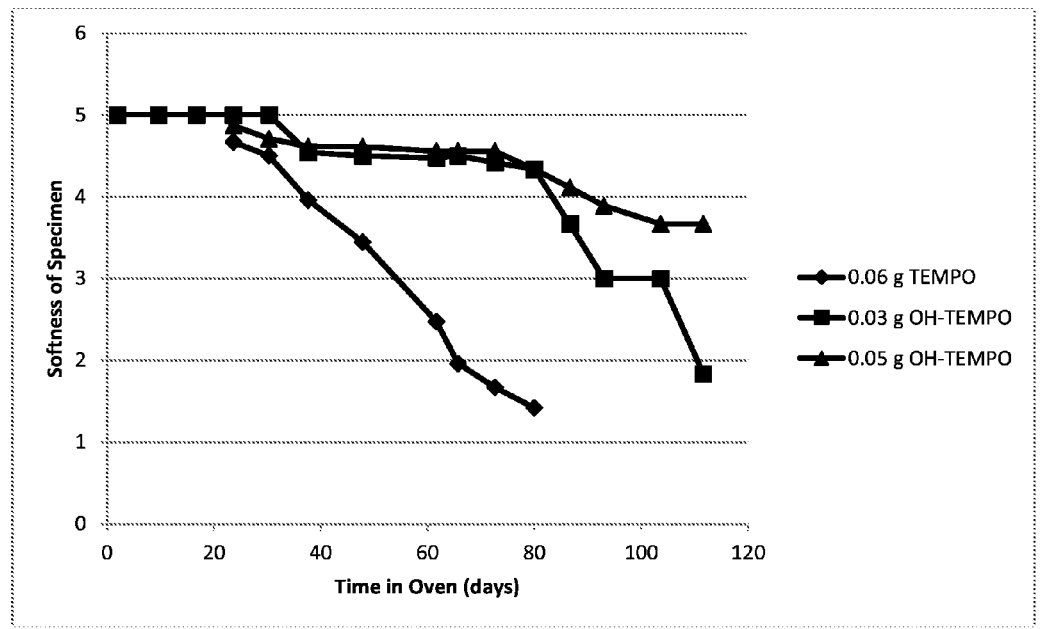
FIG. 45 is a graph of hand evaluation of shelf life specimens held in 125° F. oven using a higher levels of stabilizers.
Figure 46:
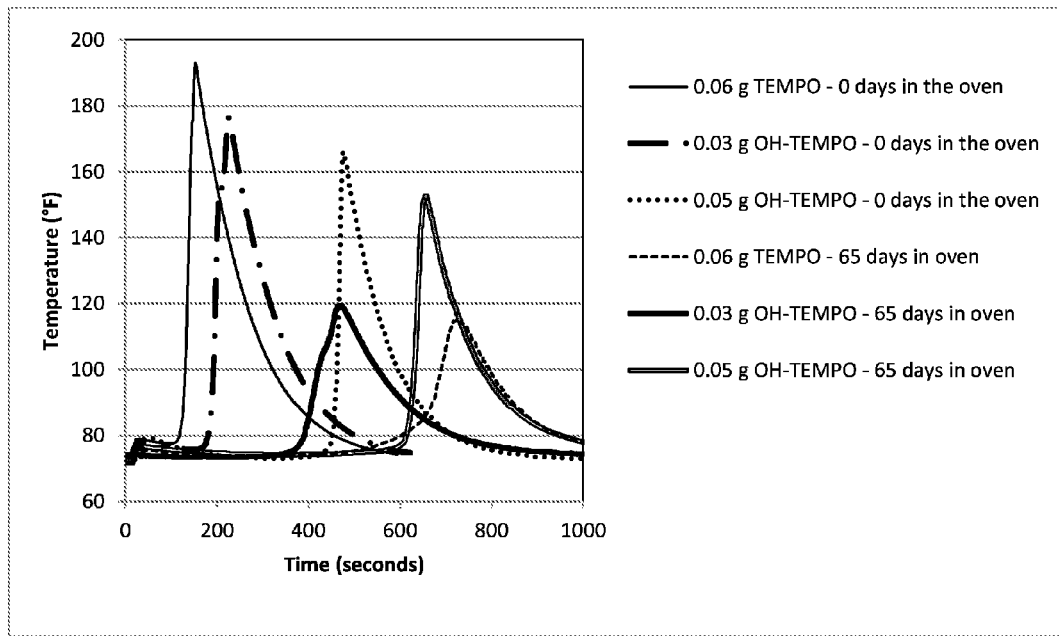
FIG. 46 is a graph of the temperature profiles during curing of air-catalyzed composite with different stabilizers.

Specimens were monitored on a weekly basis to see if there were signs of curing. Table 24 shows the scale used to gauge the specimens and FIG. 44 shows that the specimens slowly cured over time. Based on these results, TEMPO and OH-TEMPO were selected for further shelf life testing at the higher levels listed in Table 23. Specimens for further shelf life testing were made in the same manner and stored in a 125° F. oven. The specimens were evaluated by feel, as previously described, and reactivity. The reactivity was checked every three weeks by injecting 20 mL of oxygen and measuring the temperature as the specimen cured. Testing results are shown in FIG. 45 and FIG. 46.

During the course of testing, it was found that the TEMPO sublimes when in an open container. During the degassing process described in sub-section 4a and 4b of Example 4, powdered chemicals are left in open containers in the low oxygen environment. These chemicals are measured prior to being transferred into the low oxygen environment, and since there is not a scale in the glove box, there was no way to tell how the mass of TEMPO changed during the degassing process. Because of this, OH-TEMPO was selected as the stabilizer for the air-catalyzed resin. The required amount of OH-TEMPO is still being evaluated to optimize the balance between extending shelf life and maintaining fast curing.

TABLE 22

Stabilizer amounts for shelf life study

| Stabilizers | Amount |
|---|---|
| TEMPO | 0.0100 g |
|  | 0.0200 g |
|  | 0.0400 g |
|  | 0.0800 g |
| TEMPO[1] | 0.0100 g |
| TEMPO + TBP | 0.0100 g + 0.0500 g |
| OH-TEMPO | 0.0100 g |

[1]The monomer stabilizer, MEHQ, was not stripped.

TABLE 23

Stabilizer amounts for further shelf life study

| | |
|---|---|
| TEMPO | 0.0600 g |
| OH-TEMPO | 0.0300 g |
| | 0.0500 g |

TABLE 24

Scale to evaluate the shelf life specimens by hand

| Rating | Description |
|---|---|
| 5 | 0% cured - Very soft, moveable, and flexible |
| 4 | 30% cured - Some resistance to movement |
| 3 | 50% cured |
| 2 | 70% cured |
| 1 | 100% cured - Stiff and rigid |

Example 11

Encapsulating Films for the Air-Catalyzed Resin

Along with using chemical stabilizers to improve the shelf life of the air-catalyzed resin, the encapsulating film is equally important. Several different films and film combinations were tested to determine which renders the longest shelf life. Table 25 provides detailed information about the various encapsulating films, and Table 26 lists the films and film combinations tested. Two rounds of testing were completed. In both rounds, the resin was prepared and distributed on the reinforcement in a glove box with a low oxygen environment. The reinforcements were impregnated with a 40% resin weight content in a manner similar to that described in Example 4, sub-section 4b. The package, which contained the prepreg and was made from the encapsulating film(s), was sealed and then transferred out of the glove box into normal atmospheric conditions. Specimens were then put into a 125° F. oven, which accelerates the test to four times that of which it would be at room temperature, and monitored by a feel test described in Table 24.

Figure 47:
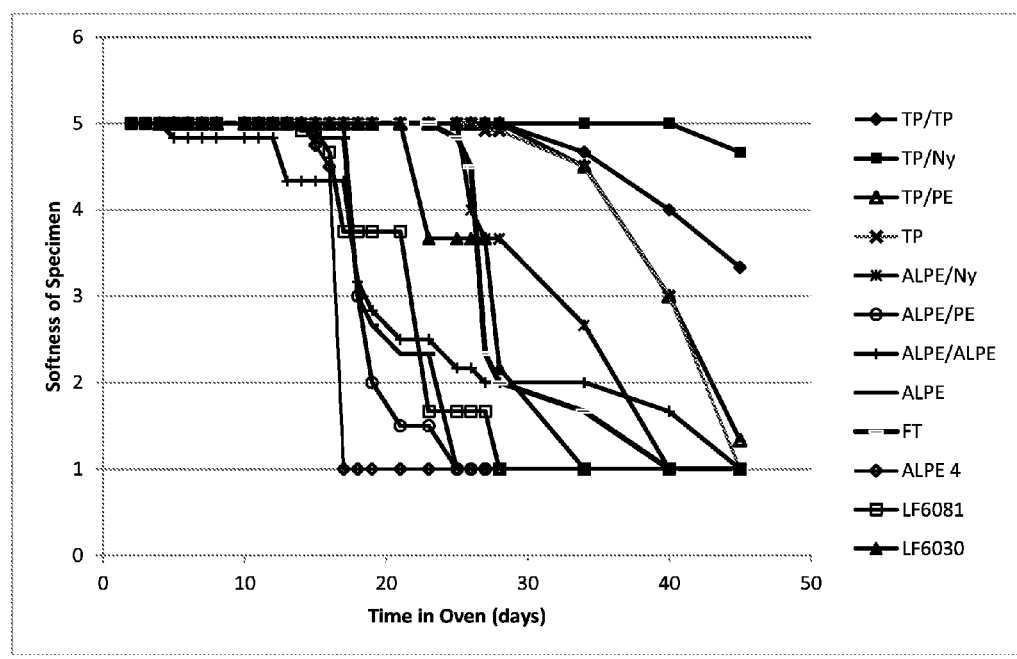
FIG. 47 is a graph of the hand evaluation of shelf life specimens held in 125° F. oven during round 1 testing with different encapsulating films.
Figure 48:
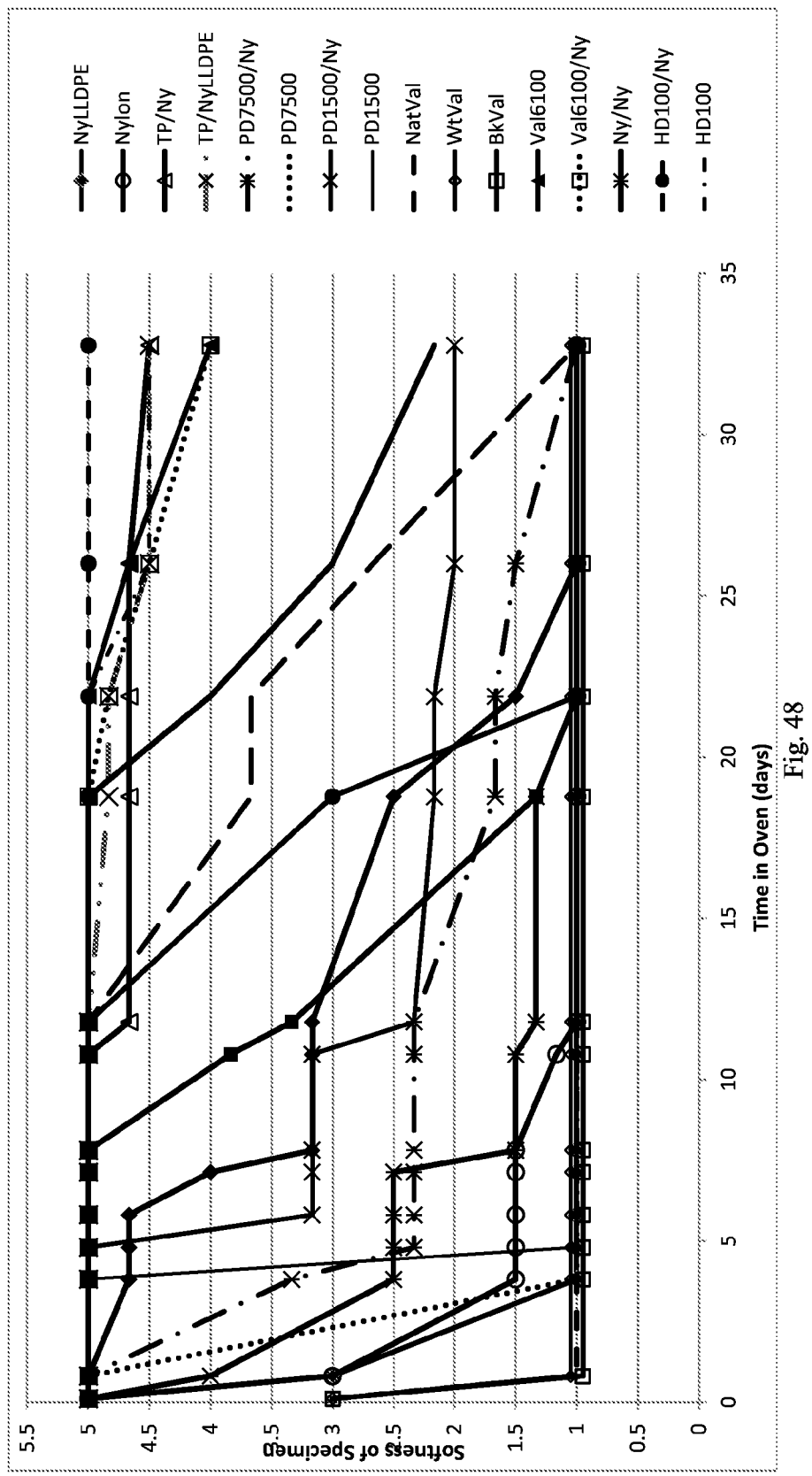
FIG. 48 is a graph of the hand evaluation of shelf life specimens held in 125° F. oven during round 2 testing with different encapsulating films.

In the first round, the resin consisted of 0.005 g OH-TEMPO, 0.0533 g CoAcAc, 14.4 mL EGD, 0.8 mL AA, 0.8 mL TMA. FIG. 47 shows the degradation of the specimens in different encapsulating films. From this, several films were eliminated. A second round of testing was then conducted in a similar manner to the first. The resin consisted of 0.0025 g OH-TEMPO, 0.0533 g CoAcAc, 14.4 mL EGD, 0.8 mL AA, 0.8 mL TMA. FIG. 48 shows how the softness of the specimen changed over time.

TABLE 25

Encapsulating film details

| | | | Composition of film layers | | | | | | Oxygen barrier |
|---|---|---|---|---|---|---|---|---|---|
| Bag Name | Supplier | Item No. | 1st layer Exterior Surface | 2nd layer | 3rd layer | 4th layer | 5th layer | 6th layer Interior Surface | (cc/100 sq. in./24 hrs) |
| TP | Ted Pella Inc. | 139-310 | 48 ga PET[1] | 12# PE[2] | 0.000285" Foil | 1.5 mil LLDEP[3] | — | — | 0.0006 |
| ALPE | Laminated Films & Packaging | LF4835W | 48 ga PET[1] | 12# White LDPE[4] | 0.00035" Foil | 2.5 mil LDPE[4] | — | — | 0.0005 |
| LF6030 | Laminated Films & Packaging | LF6030 | 60 ga Nylon | 0.0003" Foil | 0.002" PE[2] | — | — | — | 0.0005 |
| LF6081 | Laminated Films & Packaging | LF6081 | 48 ga chemically treated PET[1] | 12# White LDPE[4] | 0.000285" Foil | 12# PE[2] | 1.5 mil LLDPE[3] | — | 0.0006 |
| PAKDRY 7500 ("PD7500") | Sorbent Systems | P75C0507 | 60 ga BON[5] | 45 ga PET[1] | 0.00035" Foil | LLDPE[3] | 6.1 mil metallocene PE[2] | — | <0.0005 |
| PAKDRY 1500 ("PD1500") | Sorbent Systems | P15C0808FOZE | 48 ga metallized PET[1] | adhesive | 96 guage metallized PET[1] | 5.5 mil LLDPE[3] | — | — | <0.0005 |
| NatVal | Valeron Strength Films | VA030010 | 3 mil orieniented and cross-laminated HDPE[6] | — | — | — | — | — | — |
| WtVal | Valeron Strength Films | VA040030 | 4 mil oriented and cross-laminated HDPE[6] | — | — | — | — | — | — |
| BkVal | Valeron Strength Films | VA040110 | 4 mil oriented and cross-laminated HDPE[6] | — | — | — | — | — | — |
| Val6100 | Valeron Strength Films | Strength Pack 6100 VF0751270 | Natural Velaeron Film | Foil | PE[2] Sealant | — | — | — | <0.0003 |
| HD100 | Cepac Inc. | CadPak HD100 | BON[5] | PE[2] | Foil | PE[2] | Heavy Duty Green Coex[7] | — | 0.0005 |

TABLE 25-continued

Encapsulating film details

| Bag Name | Supplier | Item No. | Composition of film layers | | | | | | Oxygen barrier (cc/100 sq. in./24 hrs) |
|---|---|---|---|---|---|---|---|---|---|
| | | | 1st layer Exterior Surface | 2nd layer | 3rd layer | 4th layer | 5th layer | 6th layer Interior Surface | |
| HD200 | Cepac Inc. | CadPak HD200 | BON[5] | PE[2] | Valeron | PE[2] | Foil | Heavy Duty Coex[7] | 0.0005 |
| ESD | Cepac Inc. | CadPak ESD | MET-PET[8] | PE[2] | Foil | Sealant | — | — | 0.0005 |
| N | Cepac Inc. | CadPak N | Nylon | PE[2] | Foil | PE[2] | — | — | 0.0005 |
| PL | Cepac Inc. | CadPak PL | OPP[9] | PE[2] | Foil | PE[2] | — | — | 0.0005 |
| NyLLDPE | Sorbent Systems | SS0616N50 | 5 mil Nylon and LLDPE[3] combination | — | — | — | — | — | — |
| Nylon ("Ny") | Airtech | KM1300-003 | 3 mil | — | — | — | — | — | — |
| Polyethylene ("PE") | | | 6 mil | — | — | — | — | — | — |

[1]Polyethylene terephthalate (PET)
[2]Polyethylene (PE)
[3]Linear low-density polyethylene (LLDPE)
[4]Low-density polyethylene (LDPE)
[5]Biaxially oriented nylon (BON)
[6]High-density polyethylene (HDPE)
[7]Coextruded (Coex)
[8]Metalized polyethylene terephthalate (MET-PET)
[9]Oriented polypropylene (OPP)

TABLE 26

Encapsulating film configurations and abbreviations

| Configuration of encapsulating film(s) | Abbreviation |
|---|---|
| Ted Pella | TP |
| Ted Pella inside of Ted Pella | TP/TP |
| Nylon inside of Ted Pella | TP/Ny |
| Polyethylene inside of Ted Pella | TP/PE |
| NyLLDPE inside of Ted Pella | TP/NyLLDPE |
| LF4835W | ALPE |
| LF4835W inside of LF4835W | ALPE/ALPE |
| Nylon inside of LF4835W | ALPE/Ny |
| Polyethylene inside of LF4835W | ALPE/PE |
| LF6081 | LF6081 |
| LF6030 | LF6030 |
| NyLLDPE | NyLLDPE |
| Ny | Ny |
| Nylon inside of Nylon | Ny/Ny |
| PD7500 | PD7500 |
| Nylon inside of PD 7500 | PD7500/Ny |
| PD1500 | PD1500 |
| Nylon inside of PD1500 | PD1500/Ny |
| NatVal | NatVal |
| WtVal | WtVal |
| BkVal | BkVal |
| Val6100 | Val6100 |
| Nylon inside of Val6100 | Val6100/Ny |
| HD100 | HD100 |
| Nylon inside of HD100 | HD100/Nylon |
| Nylon inside of HD200 | HD200/Ny |
| Nylon inside of ESD | ESD/Ny |
| N | N |
| Nylon inside of N | N/Ny |
| Nylon inside of PL | PL/Ny |

Example 12

Comparison of Air-Cure Rapid Setting Splint and SAM Splint Full Scale Mechanical Properties Full scale specimens were fabricated and formed with a 2" radius along their full lengths to simulate their form when applied to an injured limb. These 36" long specimens were cut in half so that two 18" test specimens were harvested from each product. Each specimen was tested in four point bending with matched lower curve supports with a support span of 14" and a loading span of 3". A displacement rate of 0.25 in/min was used and load and deflection data were collected at 10 Hz. Maximum load and stiffness data for each specimen were reported. (Table 27) The air-catalyzed resin consisted of 0.037 g OH-TEMPO or TEMPO, 0.110 g CoAcAc, 27 mL EGD, 1.5 mL AA, 1.5 mL TMA. The mechanical properties of the rapid setting composite splint can be tailored by changing the reinforcement.

TABLE 27

Four-point bend test results for Air-cure resin

| Test Specimen | Average Max Load [lb] | Std Error | Average Stiffness [lb/in] | Std Error |
|---|---|---|---|---|
| SAM Splint | 10.60 | 0.41 | 71.30 | 6.29 |
| 4 Ply Air-cured fiberglass | 30.3 | 0.99 | 93.9 | 4.99 |
| 5 Ply Air-cured fiberglass | 34.1 | 2.79 | 71.6 | 9.53 |
| 6 Ply Air-cured fiberglass | 55.7 | 7.33 | 134.7 | 21.35 |

Example 13

Biomechanical Testing

The following is an overview of the biomechanical testing completed to compare splints made with the rapid-setting composites to other splint devices. Cantilever bend and axial-torsion tests were carried out with each splint specimen applied to a specially constructed analogue leg model. The legs used were custom ordered through Pacific Research Laboratories. Each leg was a medium-sized above-knee to foot model comprised of closed cell foam rubber, simulating soft tissue, with an aluminum mounting post protruding from the proximal humerus. The aluminum post, a bone analogue, continued through the foam model and terminated at six inches distal to the knee. The distal leg, having no post, was considered to have no viable bone and was dependent upon the applied splint for stabilization. The length of aluminum structure was also chosen such that the applied splints would have several inches of overlap with the structure so that there was some form of overlapping structural support along the length of the soft tissue leg. Each splint was formed per the manufacturer's instruction to fit the leg for testing and was secured using three hook and loop non-elastic straps. The straps were applied in the same location for each test (9.5", 13.5", and 18.5 inches from the proximal end of the soft tissue leg). The straps were applied in the same locations and with the same tension for each test. The leg and splint were rigidly mounted to a test fixture to ensure the stability and rigidity of the system.

Cantilever Bend Test

Figure 49:
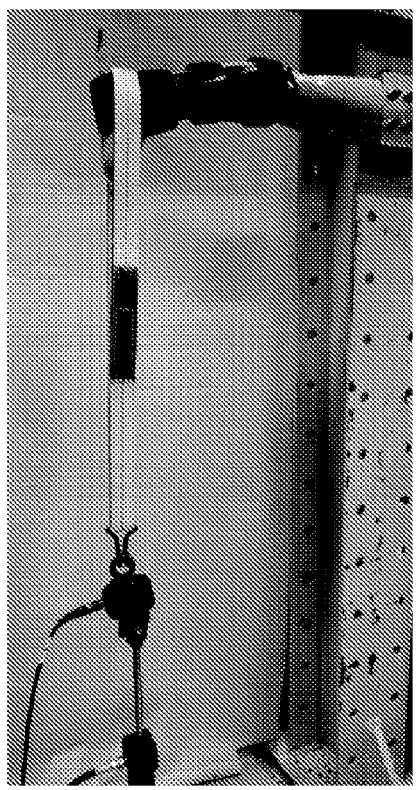
FIG. 49 is a photographic image of the cantilever bend test setup.

For the cantilever bend test, the analogue leg's aluminum post was horizontally mounted to a vertical beam and load was applied to the heel of the model in the posterior to anterior direction, with a maximum load of 40 pounds. This is shown in FIG. 49. Load, displacement, and time data were recorded for the duration of the test. A calibrated 1000 pound load cell was used to measure the applied load during the test, and a calibrated string potentiometer was used to measure displacement at the heel. A strap wrapped around the posterior of the heel and was attached to a single linear hydraulic actuator to apply load to the leg and splint. Stiffness values were calculated from the linear region of force-displacement curve for each test.

Six splint types were tested, with six specimens in each group. The SAM splint, produced by SAM Medical and the Faretec FastSet splints were used as comparative products. The other four splints were in-house prototypes, including the cyanoacrylate resin and carbon fiber splint (Cy/C), the cyanoacrylate resin and fiberglass (Cy/FG) splint, the photo-cure resin and fiberglass splint (UV/FG) splint, and the air catalyzed resin and fiberglass splint (AC/FG). The methods for construction of each type of splint are discussed in Example 2 (Cy/C and Cy/FG splints), Example 4 (AC/FG splint), and Example 5 (UV/FG splint). Table 28 details the constituent materials for each splint type tested. The results from the cantilever bend biomechanical test are displayed in Table 29.

TABLE 28

Splint Constituent Materials

|  | SAM | Faretec FastSet | Cy/C | Cy/FG | UV/FG | AC/FG |
| --- | --- | --- | --- | --- | --- | --- |
| Resin Type | NA | Unknown | Low viscosity cyanoacrylate | Low viscosity cyanoacrylate | Photo-cure resin | Aromatic tertiary amine air catalyzed resin[1] |
| Resin Volume | NA | Unknown | 45 ml | 80 ml | 55 ml | 84 ml |
| Reinforcement Type | Al | FG | C9 | FG8 | FG8 | FG15 |
| Number of Plies | NA | Unknown | 3 | 5 | 4 | 5 |
| Encapsulating Film | NA | Felt | Aluminized PE Film | Aluminized PE Film | Nylon & reflective film | Nylon & aluminized PE film |
| Binder | NA | Unknown | Hi-90 | Hi-90 | NA | NA |
| Accelerant | NA | Unknown | 3% DMT | 3% DMT | NA | NA |
| Catalyst | NA | Water | DMT | FG & DMT | Light | Oxygen |
| Distribution System | NA | NA | PVC tube | PVC tube | NA | NA |
| Phase Change Material | NA | NA | Parafilm & PE film | 1/16" PE film | NA | NA |
| Insulating Barrier | PE Foam | Felt | 1/8" PE Foam | 1/8" PE Foam | 1/16" PE Foam | 1/16" PE Foam |
| Splint Size (in) | 3 × 36" | 4 × 30" | 3 × 36" | 3 × 36" | 3 × 36" | 3 × 36" |

[1]Example 4 discusses the air catalyzed resin

TABLE 29

Cantilever Bend Test Results

| Splint Type | Stiffness (lb/in) | Standard Error |
| --- | --- | --- |
| SAM | 7.21 | 0.35 |
| Cy/C | 6.71 | 0.49 |
| Cy/FG | 8.85 | 0.34 |
| UV/FG | 10.87 | 0.66 |
| AC/FG | 10.27 | 0.58 |
| Faretec FastSet | 4.91 | 0.17 |

Axial-Torsion Test

Five different splint types were tested in combined torsion and compressive loading to compare the torsional stiffness of the leg-splint construct after each splint was applied to a custom soft tissue leg model. The splints tested include SAM splints (SAM), cyanoacrylate resin and carbon fiber splints (Cy/C), cyanoacrylate resin and fiberglass splints (Cy/FG), UV cure resin and fiberglass splints (UV/FG), and Faretec Fastset fiberglass splints. Six specimens were tested in each group. The constituent materials for each splint type can be seen in Table 28.

Figure 50:
FIG. 50 is a photographic image of the axial/torsion test setup.

A torsion test was designed to simulate the foot being rotated about the long axis of the tibia of the splinted injured leg. Each splint was applied to one of the previously mentioned analogue legs, which was then mounted in an MTS 809 axial-torsion load frame. See FIG. 50. A 550 pound/250 in-lb calibrated load cell was used to acquire axial force and torsion data for the test. A compressive axial preload of 10 lbs was applied to the leg, then the foot was rotated from its initial zero position to an internal rotation of 15 degrees and then back to its zero position at a rate of 30 deg/min. Axial force, displacement, torsion, rotation, and time data were acquired at 5 Hz during the duration of the test. The data was collected, analyzed, and the slope of the torque versus rotation curves were calculated to give the torsional stiffness of the leg/splint system. The results of the tests are shown in Table 30 below.

TABLE 30

Torsion Test Results

| Splint Type | Torsional Stiffness (lb/in/deg) | Standard Error |
|---|---|---|
| SAM | 1.27 | 0.070 |
| Cy/C | 1.56 | 0.067 |
| Cy/FG | 1.76 | 0.066 |
| UV/FG | 1.55 | 0.039 |
| Faretec FastSet | 2.13 | 0.119 |

What is claimed:

1. A fiber-reinforced composite article, the article comprising:
a multi-layer body convertible from a flexible state to a rigid state, the multi-layer body being configured to conform to an injured body part when in the flexible state and to immobilize the injured body part when in the rigid state, the multi-layer body comprising:
an insulating barrier;
an encapsulated fiber compartment;
a spacer; and
a light source configured to emit light energy;
wherein the encapsulated fiber compartment comprises a fiber reinforcement layer, photo-curable thermosetting resin, and an encapsulating film, the fiber reinforcement layer being impregnated with the photo-curable thermosetting resin and encapsulated by the encapsulating film, the photo-curable thermosetting resin being uncured when the multi-layer body is in the flexible state and being cured when the multi-layer body is in the rigid state, the photo-curable thermosetting resin being configured to begin a curing process when light energy emitted by the light source is incident on the encapsulated fiber compartment;
wherein the spacer is configured to diffuse light energy emitted by the light source, the spacer being positioned between the light source and the encapsulated fiber compartment such that light energy emitted by the light source passes through the spacer before being incident on the encapsulated fiber compartment;
wherein the insulating barrier forms a sleeve enclosing the encapsulated fiber compartment, the spacer, and the light source, the insulating barrier being configured to reduce the amount of heat transferred from the multi-layer body to the injured body part when the multi-layer body converts from the flexible state to the rigid state.

2. The fiber-reinforced composite article of claim 1, wherein the multi-layer body further comprises a reflector, the light source being positioned between the spacer and the reflector, the reflector being configured to reflect light energy emitted by the light source towards the encapsulated fiber compartment.

3. The fiber-reinforced composite article of claim 2, wherein the reflector is a first reflector and the multi-layer body further comprises a second reflector, the encapsulated fiber compartment being positioned between the second reflector and the spacer, the second reflector being configured to reflect light energy emitted by the light source towards the encapsulated fiber compartment.

4. The fiber-reinforced composite article of claim 1, wherein the article further comprises a power source, the power source being electrically connected to the light source.

5. The fiber-reinforced composite article of claim 4, wherein the power source is a battery.

6. The fiber-reinforced composite article of claim 1, wherein the light source is configured to emit light energy having a wavelength between about 350 nanometers to about 500 nanometers.

7. The fiber-reinforced composite article of claim 6, wherein the light source is configured to emit light energy having a wavelength between about 450 nanometers to about 495 nanometers.

8. The fiber-reinforced composite article of claim 1, wherein the fiber reinforcement layer comprises a plurality of fiber reinforcement plies.

9. The fiber-reinforced composite article of claim 8, wherein the plurality of fiber reinforcement layer is from two fiber reinforcement plies to four fiber reinforcement plies.

10. The fiber-reinforced composite article of claim 1, wherein the photo-curable thermosetting resin is configured such that the curing process occurs in less than about 10 minutes after being exposed to light energy emitted by the light source.

11. The fiber-reinforced composite article of claim 1, wherein the fiber reinforcement layer is selected from the group consisting of fiberglass, carbon fiber, polyaramid, and natural fibers.

12. The fiber-reinforced composite article of claim 1, wherein the article further comprises a plurality of straps, the straps being connected to the insulating barrier, the straps being configured to affix the fiber-reinforced composite article to the injured body part.

* * * * *